United States Patent

Kamireddy et al.

[11] Patent Number: 5,874,382
[45] Date of Patent: Feb. 23, 1999

[54] CYCLIC SULFONAMIDE HERBICIDES

[75] Inventors: Balreddy Kamireddy, Hockessin; William Mark Murray, Bear, both of Del.

[73] Assignee: E. I. du Pont de Nemours and Company, Wilmington, Del.

[21] Appl. No.: 12,862

[22] Filed: Jan. 23, 1998

Related U.S. Application Data

[62] Division of Ser. No. 737,649, Nov. 13, 1996, Pat. No. 5,750,471.

[51] Int. Cl.⁶ .......................... A01N 43/80; C07D 417/04
[52] U.S. Cl. .......................... 504/230; 504/246; 504/243; 504/248; 504/269; 504/263; 504/265; 504/222.8; 544/223; 544/312; 544/2; 544/5; 544/11; 544/6; 546/113; 546/117; 546/118; 546/114; 546/116; 546/119; 546/271.1; 546/198; 548/207; 548/144; 548/141
[58] Field of Search ..................................... 504/230, 243, 504/246, 248; 544/223, 312; 546/113, 117, 118, 114, 116, 119, 271.1, 198

[56] References Cited

U.S. PATENT DOCUMENTS 4,906,281   3/1990   Chang ......................................... 71/90

FOREIGN PATENT DOCUMENTS

| 0468924 | 7/1991 | European Pat. Off. . |
| 63-222167 | 9/1988 | Japan . |
| WO 87/03782 | 7/1987 | WIPO . |

OTHER PUBLICATIONS

Chemical Abstracts, vol. 110, No. 23, Jun. 5, 1989, Columbus, OH abstract No. 212837t, p. 756.

Primary Examiner—Johann Richter
Assistant Examiner—Laura R. Cross Lutz

[57] ABSTRACT

Compounds of Formula I and II, and their agriculturally-suitable salts, are disclosed which are useful for controlling undesired vegetation

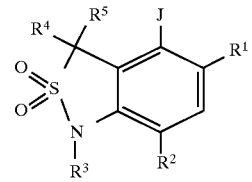

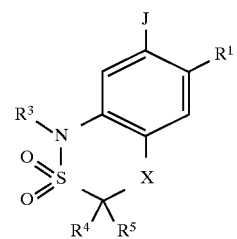

wherein
X is a direct bond; O; S; NH; $N(C_1-C_3$ alkyl); $N(C_1-C_3$ haloalkyl); or N(allyl);
$R^1$ is H; F; Cl; or Br;
$R^2$ is H; F; Cl; Br; $CF_3$; nitro; or cyano;
$R^4$ is H; $C_1-C_3$ alkyl; or halogen;
$R^5$ is H; $C_1-C_6$ alkyl; $C_1-C_6$ haloalkyl; halogen; $S(O)_2$ $(C_1-C_6$ alkyl); or $C(=O)R^8$; or
$R^4$ and $R^5$ are taken together along with the carbon to which they are attached to form a spiro-cyclopropane ring;
and $R^3$, $R^8$, and J are as defined in the disclosure.

Also disclosed are compositions containing the compounds of Formulae I and II and a method for controlling undesired vegetation which involves contacting the vegetation or its environment with an effective amount of a compound of Formula I or II.

9 Claims, No Drawings

CYCLIC SULFONAMIDE HERBICIDES

This is a division of application Ser. No. 08/737,649 filed Nov. 13, 1996, now U.S. Pat. No. 5,750,471.

BACKGROUND OF THE INVENTION

This invention relates to certain cyclic sulfonamides, their agriculturally-suitable salts and compositions, and methods of their use as general or selective preemergent or postemergent herbicides.

New compounds effective for controlling the growth of undesired vegetation are in constant demand. In the most common situation, such compounds are sought to selectively control the growth of weeds in useful crops such as cotton, rice, corn, wheat, citrus and soybeans, to name a few. Unchecked weed growth in such crops (including plantation crops) can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

U.S. Pat. No. 4,818,275 discloses herbicidal acyclic sulfonamides of the formula

[Structure depicted]

wherein, inter alia
- X and Y are Br; Cl; or F;
- R is alkyl; haloalkyl; or dialkylamino; and
- $R^1$ is H; Na; lower alkyl; or $SO_2R$.

JP 63[1988]-222167 discloses herbicidal cyclic amides and sulfonamides of the formula

[Structure depicted]

wherein
- X is H or halogen;
- Z is O or S;
- J is, inter alia, —CO— or —SO$_2$—;
- $L_1$ is —CO— or —$CR_4(R_5)$—;
- $R_4$ and $R_5$ are each independently, inter alia, H, $C_1$–$C_6$ alkyl, $C_1$–$C_6$ haloalkyl, or $CO_2R_a$;
- $R_1$ is, inter alia, H, $C_2$–$C_6$ alkoxyalkyl, $C_1$–$C_6$ alkyl, $C_1$–$C_6$ haloalkyl, $C_2$–$C_6$ alkenyl, $C_2$–$C_6$ haloalkenyl, $C_3$–$C_8$ cycloalkyl, —$COR_b$, —$CO_2R_b$, or —$CH_2CO_2R_b$;

W is, inter alia,

[Structure (W2) depicted]

- Q is N or CH;
- E is O or S;
- $R_{12}$ is H, $C_1$–$C_6$ alkyl, or $C_1$–$C_6$ haloalkyl when Q is N; or
- $R_{12}$ is H, $C_1$–$C_6$ alkyl, $C_1$–$C_6$ haloalkyl, or $C_4$ alkylene which combines with Q to form a 6-membered ring when Q is CH;
- $R_{13}$ is H, $C_1$–$C_6$ alkyl, or $C_1$–$C_6$ haloalkyl when Q is N; or
- $R_{13}$ is H, $C_1$–$C_6$ alkyl, $C_1$–$C_6$ haloalkyl, or $C_4$ alkylene which combines with Q to form a 6-membered ring when Q is CH; and
- m is 0 or 1.

The cyclic sulfonamides of the present invention are not disclosed in either of these references.

SUMMARY OF THE INVENTION

This invention includes compounds of Formulae I and II including all geometric and stereoisomers, agriculturally suitable salts thereof, agricultural compositions containing them and their use for controlling undesirable vegetation:

[Structure I depicted]

[Structure II depicted]

wherein
- X is a direct bond; O; S; NH; N($C_1$–$C_3$ alkyl); N($C_1$–$C_3$ haloalkyl); or N(allyl);
- $R^1$ is H; F; Cl; or Br;
- $R^2$ is H; F; Cl; Br; $CF_3$; nitro; or cyano;
- $R^3$ is H; $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_3$–$C_8$ alkoxyalkoxyalkyl; $C_3$–$C_8$ haloalkynyl; $C_3$–$C_8$ haloalkenyl; $C_1$–$C_8$ alkylsulfonyl; $C_1$–$C_8$ haloalkylsulfonyl; $C_3$–$C_8$ alkoxycarbonylalkyl; $S(O)_2NH(C_1$–$C_8$ alkyl); $C(O)R^6$; or benzyl optionally substituted on the phenyl ring with $R^7$;
- $R^4$ is H; $C_1$–$C_3$ alkyl; or halogen;
- $R^5$ is H; $C_1$–$C_6$ alkyl; $C_1$–$C_6$ haloalkyl; halogen; $S(O)_2(C_1$–$C_6$ alkyl); or $C(=O)R^8$; or
- $R^4$ and $R^5$ are taken together along with the carbon to which they are attached to form a spiro-cyclopropane ring;

$R^6$ is $C_1$–$C_6$ alkyl; $C_1$–$C_6$ haloalkyl; $C_1$–$C_6$ alkoxy; NH($C_1$–$C_6$ alkyl); phenyl optionally substituted with $R^7$; benzyl; or $C_2$–$C_8$ dialkylamnino;
$R^7$ is $C_1$–$C_6$ alkyl; 1–2 halogen; $C_1$–$C_6$ alkoxy; or $CF_3$;
$R^8$ is H; $C_1$–$C_6$ alkyl; $C_1$–$C_6$ alkoxy; or NH($C_1$–$C_6$ alkyl);
J is
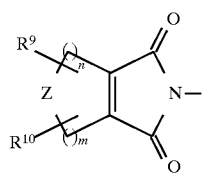  J-1
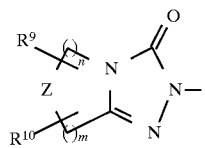  J-2
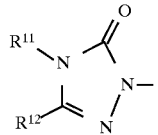  J-3
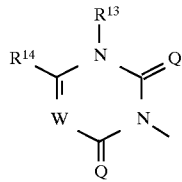  J-4
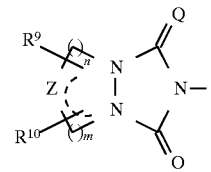  J-5
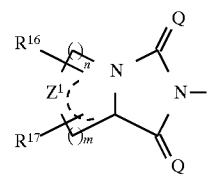  J-6
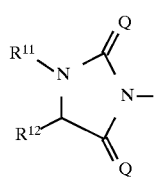  J-7
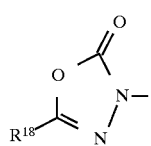  J-8
-continued
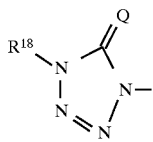  J-9
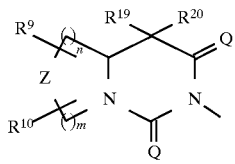  J-10
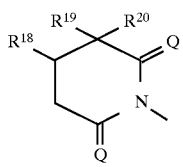  J-11
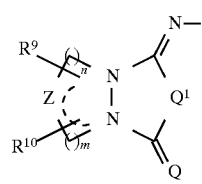  J-12
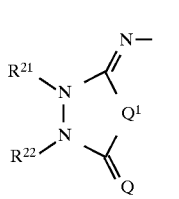  J-13
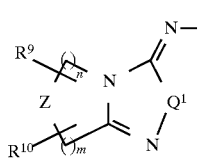  J-14
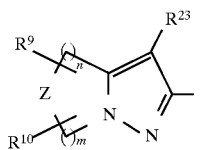  J-15
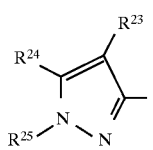  J-16
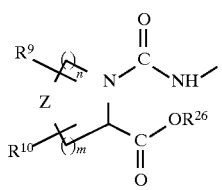  J-17

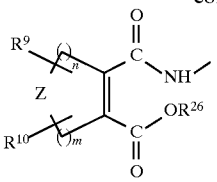

wherein the dashed line in J-5, J-6 and J-12 indicates that the left-hand ring contains only single bonds or one bond in the ring is a carbon-carbon double bond;

n and m are each independently 0; 1; 2; or 3; provided that m+n is 2 or 3;

Z is $CR^9R^{10}$; O; S; S(O); S(O)$_2$; N(C$_1$-C$_4$ alkyl; or

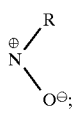

each $R^9$ is independently H; C$_1$-C$_3$ alkyl; halogen; hydroxy; C$_1$-C$_6$ alkoxy; C$_1$-C$_6$ haloalkyl; C$_1$-C$_6$ haloalkoxy; C$_2$-C$_6$ alkylcarbonyloxy; or C$_2$-C$_6$ haloalkylcarbonyloxy;

each $R^{10}$ is independently H; C$_1$-C$_3$ alkyl; hydroxy; or halogen;

$R^{11}$ and $R^{12}$ are each independently H; halogen; C$_1$-C$_6$ alkyl; C$_3$-C$_6$ alkenyl; or C$_1$-C$_6$ haloalkyl;

$R^{13}$ is H; C$_1$-C$_6$ alkyl; C$_1$-C$_6$ haloalkyl; C$_3$-C$_6$ alkenyl; C$_3$-C$_6$ haloalkenyl; C$_3$-C$_6$ alkynyl; C$_3$-C$_6$ haloalkynyl; HC(=O); (C$_1$-C$_4$ alkyl)C(=O); or NH$_2$;

$R^{14}$ is C$_1$-C$_6$ alkyl; C$_1$-C$_6$ alkylthio; C$_1$-C$_6$ haloalkyl; CF$_3$; or N(CH$_3$)$_2$;

W is N or $CR^{15}$;

$R^{15}$ is H; C$_1$-C$_6$ alkyl; halogen; or phenyl optionally substituted with C$_1$-C$_6$ alkyl, 1-2 halogen, C$_1$-C$_6$ alkoxy, or CF$_3$;

each Q is independently O or S;

$Q^1$ is O or S;

$Z^1$ is $CR^{16}R^{17}$; O; S; S(O); S(O)$_2$; N(C$_1$-C$_4$ alkyl; or

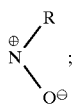

each $R^{16}$ is independently H; halogen; hydroxy; C$_1$-C$_6$ alkoxy; C$_1$-C$_6$ haloalkyl; C$_1$-C$_6$ haloalkoxy; C$_2$-C$_6$ alkylcarbonyloxy; or C$_2$-C$_6$ haloalkylcarbonyloxy;

each $R^{17}$ is independently H; hydroxy; or halogen; or when $R^{16}$ and $R^{17}$ are bonded to adjacent atoms they can be taken together with the carbons to which they are attached to form

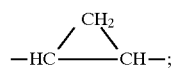

$R^{18}$ is C$_1$-C$_6$ alkyl; halogen; or C$_1$-C$_6$ haloalkyl;

$R^{19}$ and $R^{20}$ are each independently H; C$_1$-C$_6$ alkyl; or C$_1$-C$_6$ haloalkyl;

$R^{21}$ and $R^{22}$ are each independently C$_1$-C$_6$ alkyl; C$_1$-C$_6$ haloalkyl; C$_3$-C$_6$ alkenyl; C$_3$-C$_6$ haloalkenyl; C$_3$-C$_6$ alkynyl; or C$_3$-C$_6$ haloalkynyl;

$R^{23}$ is halogen or cyano;

$R^{24}$ is C$_1$-C$_6$ alkylsulfonyl; C$_1$-C$_6$ alkyl; C$_1$-C$_6$ haloalkyl; C$_3$-C$_6$ alkenyl; C$_3$-C$_6$ alkynyl; C$_1$-C$_6$ alkoxy; C$_1$-C$_6$ haloalkoxy; or halogen;

$R^{25}$ is C$_1$-C$_6$ alkyl; C$_1$-C$_6$ haloalkyl; C$_3$-C$_6$ alkenyl; or C$_3$-C$_6$ alkynyl; and $R^{26}$ is C$_1$-C$_6$ alkyl; C$_1$-C$_6$ haloalkyl; or phenyl optionally substituted with C$_1$-C$_6$ alkyl, 1-2 halogen, 1-2 nitro, C$_1$-C$_6$ alkoxy, or CF$_3$;

provided that when X is O or S in Formula II, then J is other than J-6 or J-7.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as 1-propenyl, 2-propenyl, and the different butenyl, pentenyl and hexenyl isomers. "Alkenyl" also includes polyenes such as 1,3-hexadienyl and 2,4,6-heptatrienyl. "Alkynyl" includes straight-chain or branched alkynes such as 1-propynyl, 3-propynyl and the different butynyl, pentynyl and hexynyl isomers. "Alkynyl" can also include moieties comprised of multiple triple bonds such as 2,7-octadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. "Alkoxyalkoxy" denotes alkoxy substitution on alkoxy. Examples of "alkoxyalkyl" include CH$_3$OCH$_2$, CH$_3$OCH$_2$CH$_2$, CH$_3$CH$_2$OCH$_2$, CH$_3$CH$_2$CH$_2$CH$_2$OCH$_2$ and CH$_3$CH$_2$OCH$_2$CH$_2$. "Alkylthio" includes branched or straight-chain alkylthio moieties such as methylthio, ethylthio, and the different propylthio, butylthio, pentylthio and hexylthio isomers. Examples of "alkylsulfonyl" include CH$_3$S(O)$_2$, CH$_3$CH$_2$S(O)$_2$, CH$_3$CH$_2$CH$_2$S(O)$_2$, (CH$_3$)$_2$CHS(O)$_2$ and the different butylsulfonyl, pentylsulfonyl and hexylsulfonyl isomers. "Dialkylamino" is defined analogously to the above examples. "Cycloalkyl" includes, for example, cyclopropyl, cyclobutyl, cyclopentyl, and cyclohexyl.

The term "halogen", either alone or in compound words such as "haloalkyl", includes fluorine, chlorine, bromine or iodine. The term "1-2 halogen" indicates that one or two of the available positions for that substituent may be halogen. Further, when used in compound words such as "haloalkyl", said alkyl may be partially or fully substituted with halogen atoms which may be the same or different. Examples of "haloalkyl" include F$_3$C, ClCH$_2$, CF$_3$CH$_2$ and CF$_3$CCl$_2$. The terms "haloalkenyl", "haloalkynyl" "haloalkoxy", and the like are defined analogously to the term "haloalkyl". Examples of "haloalkenyl" include (Cl)$_2$C=CHCH$_2$ and CF$_3$CH$_2$CH=CHCH$_2$. Examples of "haloalkynyl" include HC≡CCHCl, CF$_3$C≡C, CCl$_3$C≡C and FCH$_2$C≡CCH$_2$. Examples of "haloalkoxy" include CF$_3$O, CCl$_3$CH$_2$O, HCF$_2$CH$_2$CH$_2$O and CF$_3$CH$_2$O. Examples of "haloalkylsulfonyl" include CF$_3$SO$_2$, CCl$_3$SO$_2$, CF$_3$CH$_2$SO$_2$ and CF$_3$CF$_2$SO$_2$.

The total number of carbon atoms in a substituent group is indicated by the "C$_i$-C$_j$" prefix where i and j are numbers from 1 to 8. For example, C$_1$-C$_3$ alkylsulfonyl designates methylsulfonyl through propylsulfonyl; C$_2$ alkoxyalkoxy designates CH$_3$OCH$_2$O; C$_3$ alkoxyalkoxy designates, for example, CH$_3$CH(OCH$_3$)O, CH$_3$OCH$_2$CH$_2$O or CH$_3$CH$_2$OCH$_2$O; and C$_4$ alkoxyalkoxy designates the various isomers of an alkoxy group substituted with a second alkoxy group containing a total of four carbon atoms, examples including CH$_3$CH$_2$CH$_2$OCH$_2$O, and CH$_3$CH$_2$OCH$_2$CH$_2$O. Examples of "alkylcarbonyl" include C(O)CH$_3$, C(O)CH$_2$CH$_2$CH$_3$ and C(O)CH(CH$_3$)$_2$. Examples of "alkoxycarbonyl" include CH$_3$OC(=O), CH$_3$CH$_2$OC(=O), CH$_3$CH$_2$CH$_2$OC(=O), (CH$_3$)$_2$CHOC(=O) and the different butoxy-, pentoxy- or hexyloxycarbonyl isomers.

When a group contains a substituent which can be hydrogen, for example R$^1$ or R$^9$, then, when this substituent is taken as hydrogen, it is recognized that this is equivalent to said group being unsubstituted by that substituent.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate and/or to selectively prepare said stereoisomers. Accordingly, the present invention comprises mixtures, individual stereoisomers, and optically active mixtures of compounds of Formulae I and II as well as agriculturally suitable salts thereof.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group.

Preferred compounds, compositions containing them, and methods of their use for reasons of better activity and/or ease of synthesis are:

Preferred 1. Compounds of Formulae I and II above, and agriculturally-suitable salts thereof, wherein:

X is a direct bond or O;

R$^1$ is F or Cl;

R$^2$ is F; Cl; or Br;

R$^3$ is H; C$_1$–C$_6$ alkyl; C$_3$–C$_6$ cycloalkyl; C$_3$–C$_6$ alkenyl; C$_3$–C$_6$ alkynyl; C$_1$–C$_6$ haloalkyl; C$_2$–C$_6$ alkoxyalkyl; C$_3$–C$_6$ haloalkenyl; C$_1$–C$_6$ alkylsufonyl; C$_3$–C$_6$ alkoxycarbonylalkyl; C(O)R$^6$; or benzyl optionally substituted on the phenyl ring with R$^7$;

R$^4$ is H or halogen;

R$^5$ is H;

J is J-1; J-2; J-3; J-4; J-5; J-6; J-8; J-12; J-15; or J-16;

Z is CR$^9$R$^{10}$; O; S; or N(C$_1$–C$_4$ alkyl);

each R$^9$ is independently H; halogen; or C$_1$–C$_6$ haloalkoxy;

each R$^{10}$ is independently H or halogen;

each Q is O;

Q$^1$ is S;

Z$^1$ is CR$^{16}$R$^{17}$; O; S; or N(C$_1$–C$_4$ alkyl);

each R$^{16}$ is independently H; halogen; or haloalkoxy;

each R$^{17}$ is independently H or halogen; or when R$^{16}$ and R$^{17}$ are bonded to adjacent atoms they can be taken together with the carbons to which they are attached to form

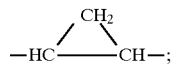

R$^{18}$ is t-butyl or CH$_2$CH$_2$CH$_2$F;

R$^{23}$ is Cl or cyano; and

R$^{24}$ is C$_1$–C$_4$ haloalkyl or C$_1$–C$_6$ haloalkoxy.

Preferred 2. Compounds of Preferred 1 wherein:

R$^2$ is F or Cl;

R$^3$ is C$_1$–C$_6$ alkyl; C$_3$–C$_6$ cycloalkyl; C$_3$–C$_6$ alkenyl; C$_3$–C$_6$ alkynyl; C$_3$–C$_6$ alkoxycarbonylalkyl; or benzyl optionally substituted on the phenyl ring with R$^7$;

J is J-1; J-2; J-3; J-4; J-5; J-6; J-8; or J-12;

Z is CR$^9$R$^{10}$ or O;

each R$^9$ is independently H or halogen;

R$^{11}$ is C$_1$–C$_4$ haloalkyl;

R$^{12}$ is C$_1$–C$_4$ alkyl;

R$^{13}$ is CH$_3$;

R$^{14}$ is CF$_3$;

W is CH;

Z$^1$ is CR$^{16}$R$^{17}$ or O;

each R$^{16}$ is independently H or halogen;

each R$^{17}$ is independently H or halogen; or when R$^{16}$ and R$^{17}$ are bonded to adjacent atoms they can be taken together with the carbons to which they are attached to form

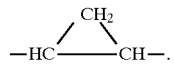

Preferred 3. Compounds of Preferred 2 wherein:

R$^2$ is Cl;

R$^3$ is C$_1$–C$_6$ alkyl; C$_3$–C$_6$ alkenyl; or C$_3$–C$_6$ alkynyl;

J is J-1; J-2; J-3; J-4; J-6; or J-12;

Z is CR$^9$R$^{10}$;

R$^9$ is independently H or F;

R$^{10}$ is independently H or F;

R$^{11}$ is CF$_2$H;

R$^{12}$ is CH$_3$;

Z$^1$ is CR$^{16}$R$^{17}$;

R$^{16}$ is independently H or F; and

R$^{17}$ is independently H or F.

Most preferred are compounds of Preferred 1 selected from the group:

3-[7-chloro-5-fluoro-1,3-dihydro-1-[(4-methoxyphenyl)methyl]-2,1-benzisothiazol-4-yl]-1-methyl-6-(trifluoromethyl)-2,4(1H,3H)-pyrimidinedione S,S-dioxide;

3-(7-chloro-5-fluoro-1,3-dihydro-2,1-benzisothiazol-4-yl)-1-methyl-6-(trifluoromethyl)-2,4(1H,3H)-pyrimidinedione S,S-dioxide;

3-(7-chloro-1-ethyl-5-fluoro-1,3-dihydro-2,1-benzisothiazol-4-yl)-1-methyl-6-(trifluoromethyl)-2,4(1H,3H)-pyrimidinedione S,S-dioxide; and 3-[(7-chloro-1-ethyl-5-fluoro-1,3-dihydro-2,1-benzisothiazol-4-yl)imino]tetrahydro-1H,3H-[1,3,4]thiadiazolo[3,4-α]pyridazin-1-one S,S-dioxide.

The invention further comprises anilines of Formula 1 and 2 wherein R$^1$, R$^2$, R$^3$, R$^4$, R$^5$ and X are as defined for compounds of Formula I and II above. The anilines are intermediates in the preparation of compounds of Formula I and II.

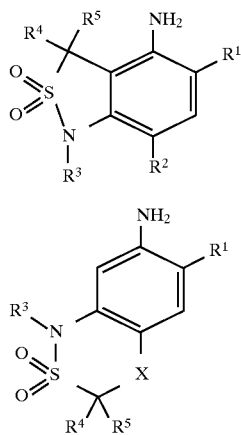

DETAILS OF THE INVENTION

The compounds of Formulae I and II can be prepared by one or more of the following methods, or variations obvious to one skilled in the art, as described below in Schemes 1–21. The definitions of Z, $Z^1$, Q, $Q^1$, X, W, n, m, and $R^1$ through $R^{26}$ in the compounds of Formulae 1–46 below are as defined above in the Summary of the Invention. Compounds of Formulae Ia-Ir are various subsets of the compounds of Formula I, and all substituents for Formulae Ia-Ir are as defined above for Formula I.

Compounds of Formulae I and II are prepared from the corresponding anilines of Formulae 1 and 2, respectively, as represented in Scheme 1.

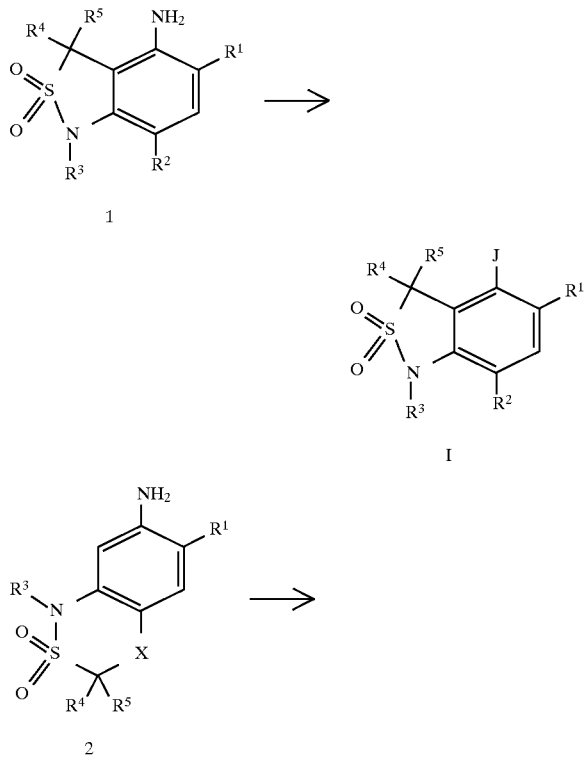

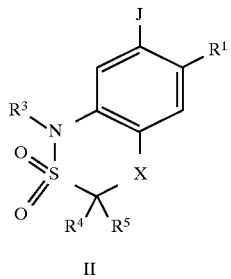

Synthesis of Anilines of Formulae 1 and 2

Anilines of Formulae 1 and 2 wherein X is a direct bond (Formula 2a) are prepared by the method illustrated in Scheme 2. The nitro aniline of Formula 3 is treated with a sulfonyl chloride in the presence of a base such as pyridine, N,N-dimethylaminopyridine (DMAP), or triethylamine at −20° to 25° C. to obtain the sulfonamide of Formula 4. For compounds wherein $R^3$ is other than H, the sulfonamide nitrogen can be alkylated or acylated to give the $R^3$-substituted compound of Formula 5. The alkylation is performed using an alkyl halide or alkyl sulfonate in the presence of a base such as potassium carbonate, sodium methoxide, potassium t-butoxide (t-BuOK), or sodium hydride in an anhydrous solvent such as dimethylformamide (DMF), tetrahydrofaran, or acetonitrile at ambient temperature to 80° C. Acylations to form the $R^3$=C(O)$R^6$ compounds are accomplished by condensing the sulfonamide of Formula 4 with the appropriate acylating agent, for example an acyl chloride, isocyanate or carbamoyl chloride.

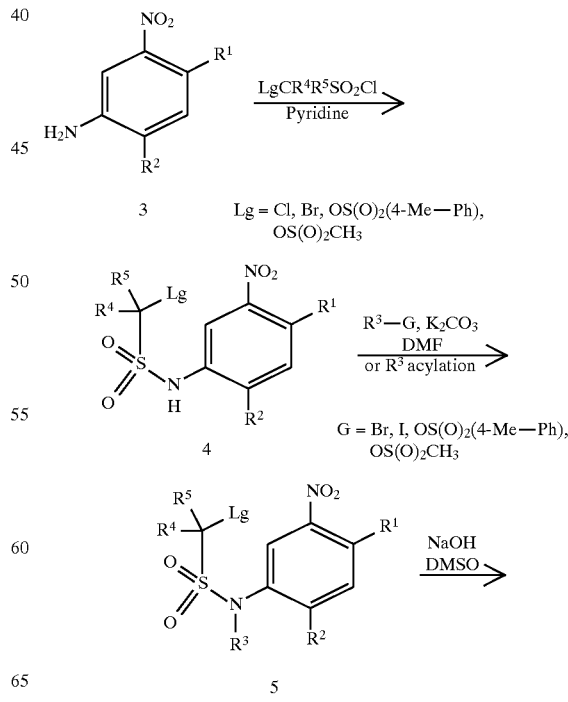

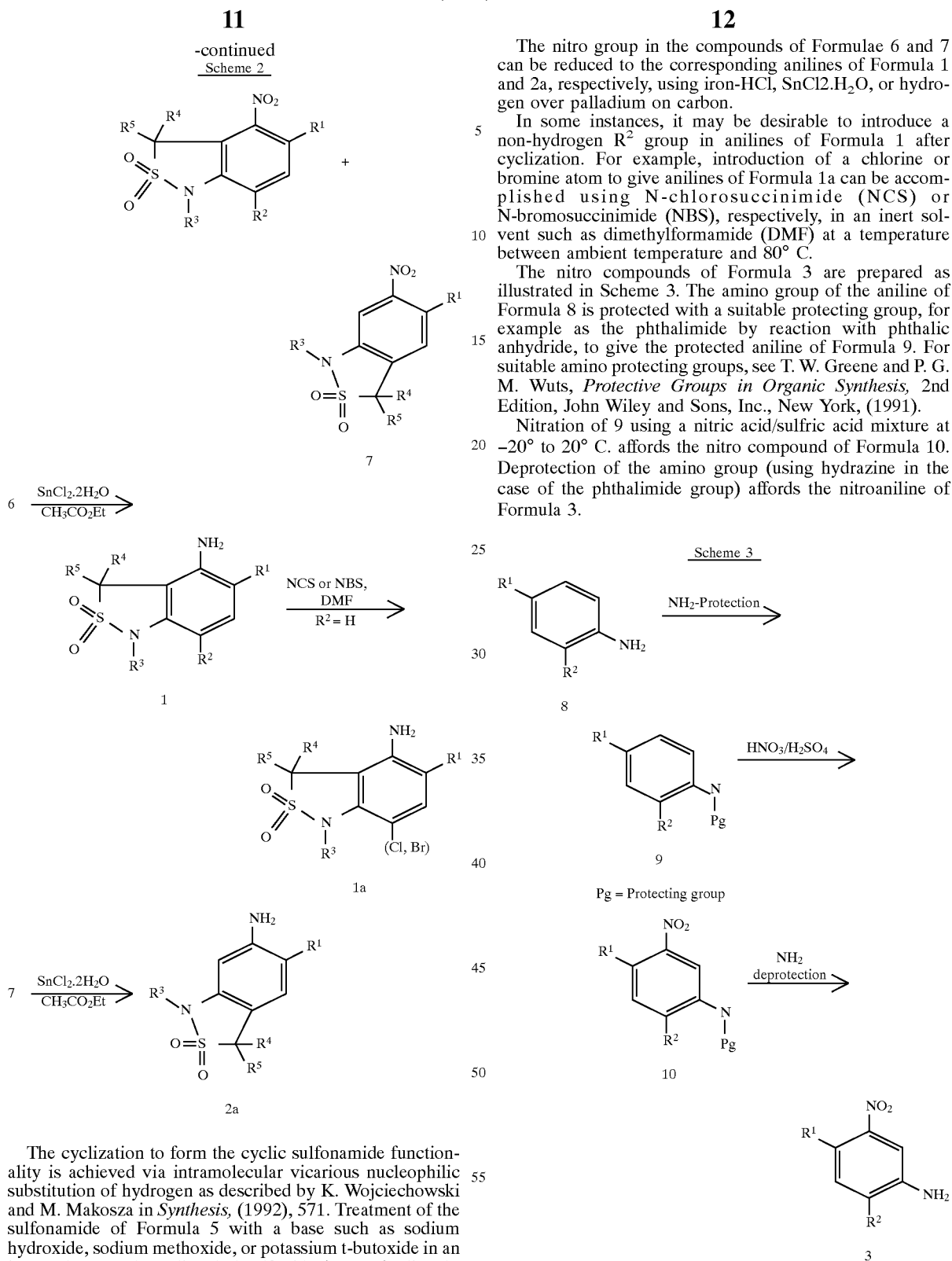

The nitro group in the compounds of Formulae 6 and 7 can be reduced to the corresponding anilines of Formula 1 and 2a, respectively, using iron-HCl, $SnCl_2 \cdot H_2O$, or hydrogen over palladium on carbon.

In some instances, it may be desirable to introduce a non-hydrogen $R^2$ group in anilines of Formula 1 after cyclization. For example, introduction of a chlorine or bromine atom to give anilines of Formula 1a can be accomplished using N-chlorosuccinimide (NCS) or N-bromosuccinimide (NBS), respectively, in an inert solvent such as dimethylformamide (DMF) at a temperature between ambient temperature and 80° C.

The nitro compounds of Formula 3 are prepared as illustrated in Scheme 3. The amino group of the aniline of Formula 8 is protected with a suitable protecting group, for example as the phthalimide by reaction with phthalic anhydride, to give the protected aniline of Formula 9. For suitable amino protecting groups, see T. W. Greene and P. G. M. Wuts, *Protective Groups in Organic Synthesis*, 2nd Edition, John Wiley and Sons, Inc., New York, (1991).

Nitration of 9 using a nitric acid/sulfric acid mixture at −20° to 20° C. affords the nitro compound of Formula 10. Deprotection of the amino group (using hydrazine in the case of the phthalimide group) affords the nitroaniline of Formula 3.

The cyclization to form the cyclic sulfonamide functionality is achieved via intramolecular vicarious nucleophilic substitution of hydrogen as described by K. Wojciechowski and M. Makosza in *Synthesis,* (1992), 571. Treatment of the sulfonamide of Formula 5 with a base such as sodium hydroxide, sodium methoxide, or potassium t-butoxide in an inert solvent such as dimethyl sulfoxide ($Me_2SO$), dimethylformamide or tetrahydrofuran at a temperature between −60° C. and ambient temperature affords the cyclic sulfonamides of Formulae 6 and 7. The ratio of products depends on the nature of $R^2$, and the base and solvent used in the cyclization. If $R^2$ is other than hydrogen, only compounds of Formula 6 are obtained. When $R^2$ is hydrogen and a mixture of products is obtained, the isomers can be separated by chromatography or crystallization techniques.

The anilines of Formula 8 are known or can be prepared by well-known methods (see March, J., *Advanced Organic Chemistry,* (1992), 4th Ed., John Wiley and Sons, Inc., pp 591, 1103–1105).

Anilines of Formulae 1 and 2a can also be prepared by introduction of the nitro group further along in the synthetic pathway as illustrated in Scheme 4.

Scheme 4

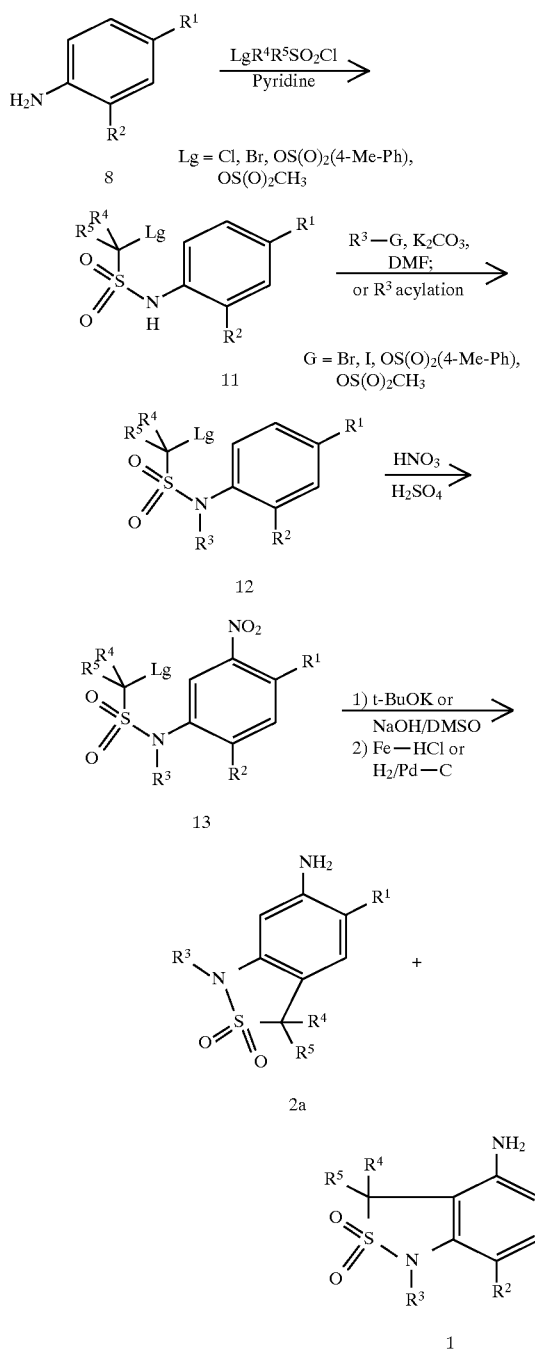

Scheme 5

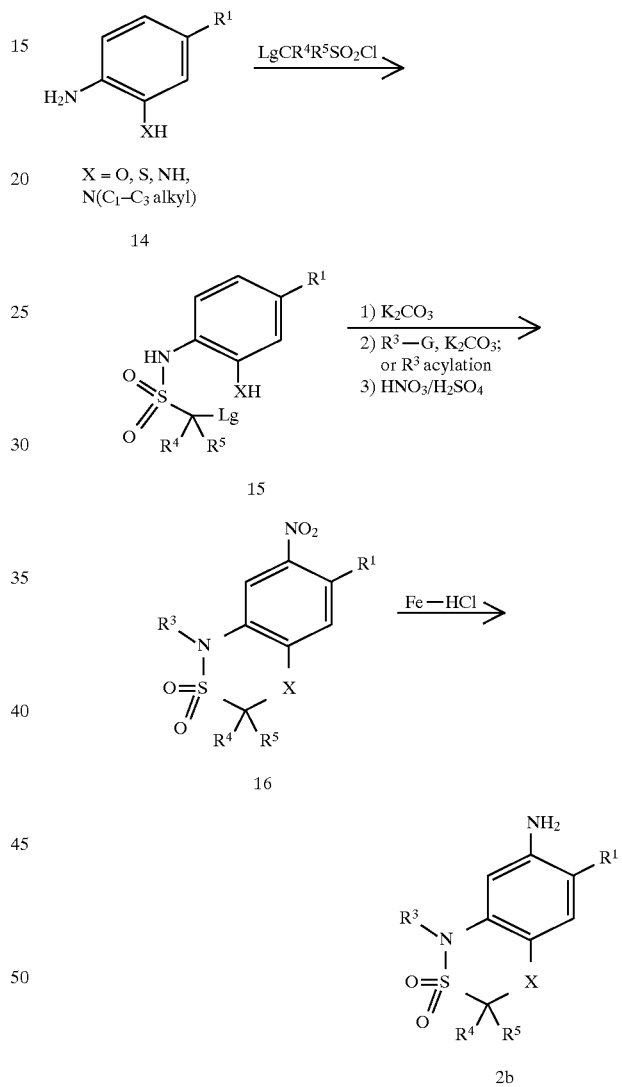

The aniline of Formula 8 is contacted with a sulfonyl chloride as described above to give the sulfonamide of Formula 11. N-Acylation with an acyl chloride or the like, or N-alkylation with an $R^3$-halide or -sulfonate in the presence of a base, as described above provides the N-substituted sulfonamide of Formula 12. Nitration to form the nitro compound of Formula 13 can be achieved using a nitric acid/sulfuric acid mixture at −20° to 20° C. Vicarious intramolecular nucleophilic substitution followed by reduction of the nitro group using the conditions described previously affords the anilines of Formulae 1 and 2a.

Anilines of Formula 2 wherein X is other than a direct bond (Formula 2b) can be prepared starting from the corresponding amino phenol (X=O), amino thiophenol (X=S), or diamine (X=NH or $N(C_1-C_3$ alkyl)) of Formula 14 as illustrated in Scheme 5. Using conditions described above, the aniline is treated with a sulfonyl chloride to give the sulfonamide of Formula 15. Subsequent treatment with a base, for example potassium carbonate, induces cyclization. Nitration with nitric and sulfuric acid affords the corresponding nitro compound of Formula 16. N-Alkylation or N-acylation to introduce $R^3$ followed by reduction of the nitro group using the reaction conditions described above gives the aniline of Formula 2b.

A similar but alternative method for the preparation of anilines of Formula 2b is outlined in Scheme 6. Starting with the nitro compound of Formula 17, the phenol (X=O), thiol (X=S), or amino (X=NH or $N(C_1-C_3$ alkyl)) group is protected with a suitable protecting group (see T. W. Greene and P. G. M. Wuts, *Protective Groups in Organic Synthesis*, 2nd Edition, John Wiley and Sons, Inc., New York, (1991)). For example, a benzyl (Bn) group is a particularly suitable protecting group and is introduced by treatment with benzyl bromide (BnBr) in the presence of $K_2CO_3$. Reduction of the nitro group, for example with iron and HCl as described above, affords the aniline of Formula 18. Condensation with a sulfonyl chloride followed by N-alkylation or N-acylation affords the N-substituted sulfonamide of Formula 19.

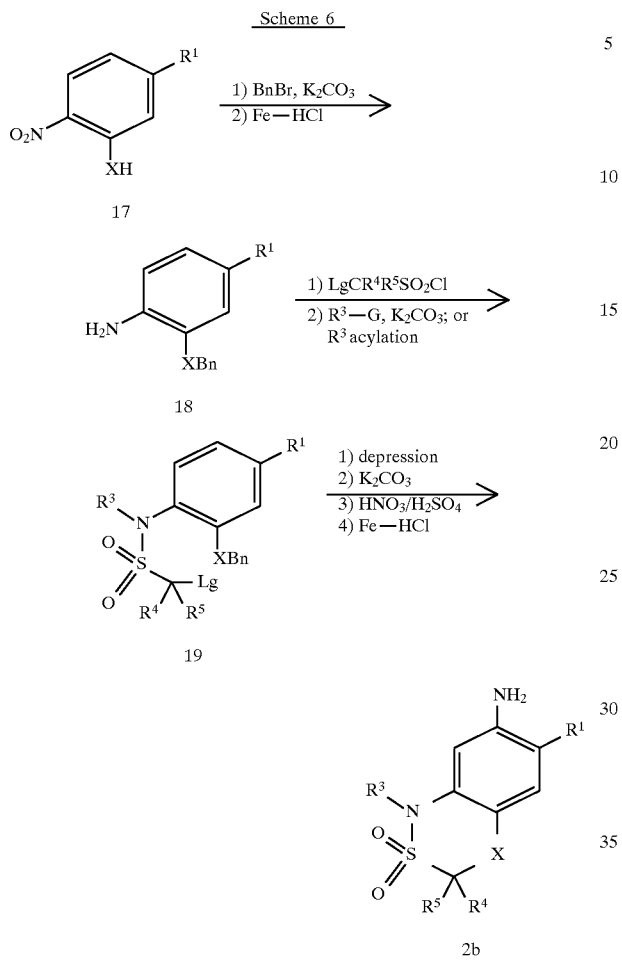

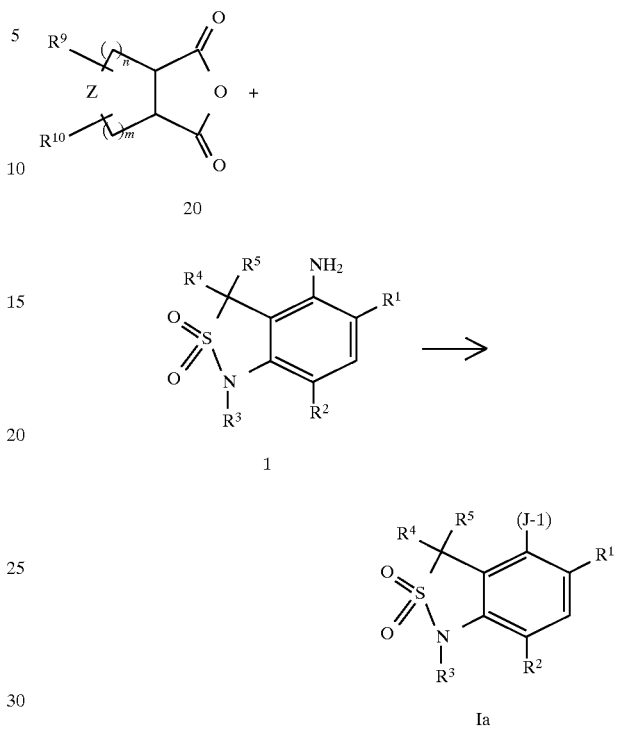

Removal of the protecting group under the appropriate conditions (for example, by treatment with hydrogen over palladium on carbon in the case of an OBn group) and treatment with base induces cyclization to form the cyclic sulfonamide. Nitration and reduction as described above affords the aniline of Formula 2b.

Converting Anilines of Formulae 1 and 2 to Compounds of Formulae I and II

The anilines prepared by the methods outlined in Schemes 1–6 are used in the condensation with J group derivatives to form compounds of Formulae I and II. In some instances, the anilines are used directly in the condensation reactions. In other instances and depending on the nature of the J-group, the $NH_2$ of the aniline is first converted to another functional group prior to condensation. For example, the aniline may be converted first to a hydrazine, an isocyanate or an aryl iodide. These methods are described in more detail below.

Direct Coupling with the Anilines

In some instances where the aniline is used directly, the compounds of Formulae I and II are prepared by condensation of the aniline with an anhydride precursor to the J group. For example, as illustrated in Scheme 7, the anhydride of Formula 20 is condensed with the aniline of Formula 1 to give compounds of Formula Ia wherein J=J-1. This method is disclosed in EP-A-170,191.

The anhydride of Formula 20 can be prepared by methods disclosed in EP 493,721, and WO 91/06216. Compounds of Formulae I and II wherein J=J-11 and J-18 can be prepared using similar methodology. The aniline is condensed with the appropriate J-group anhydride, diester, or other bis-electrophile to form the compound of Formula I or II. The synthesis of the J-11 precursor and the condensation reaction is described in EP 454,444 and EP 415,642. The J-18 group anhydride and the aniline condensation reaction are described in U.S. Pat. No. 4,003,926.

The sulfonamides of Formulae I and II wherein J=J-10 are also prepared directly from the anilines of Formula 1 and 2, respectively. The J-10 group precursor and the aniline condensation reaction are described in WO 94/03459.

Hydrazines

For some compounds of Formulae I and II, the appropriate aniline is first converted to the corresponding hydrazine, and then the hydrazine is condensed with the J-group derivative, or precursor thereof, to form the desired material. The conversion of an aniline of Formula 1 to a hydrazine of Formula 21 is illustrated in Scheme 8. Subsequent condensation of the hydrazine with the iminoether precursor to J-2 followed by cyclization with phosgene forms the cyclic sulfonamide of Formula Ib. The preparation of the iminoether J-2 precursor and the condensation procedure is described in U.S. Pat. No. 4,315,767.

Scheme 8

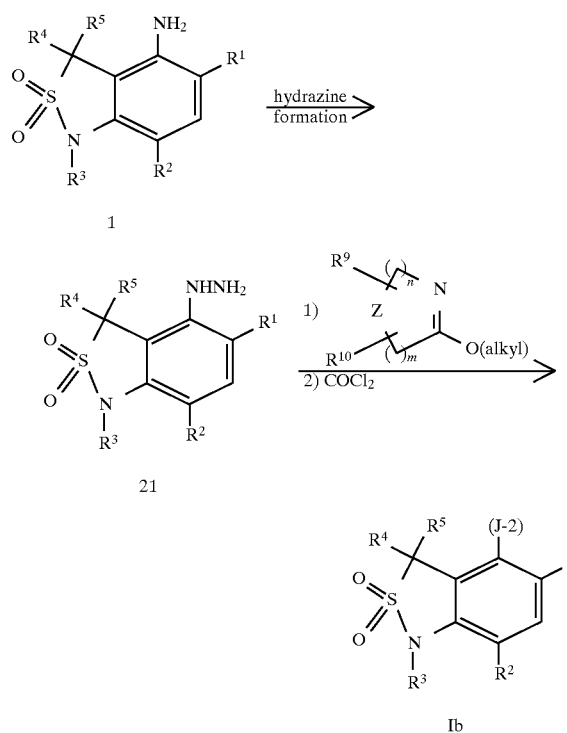

Anilines can be converted to the hydrazines by diazotization and then reduction as is well-known in the literature (for example, see U.S. Pat. No. 4,695,312).

Compounds of Formulae I and II wherein J=J-3 and J-8 are also prepared by first converting the aniline to the appropriate hydrazine, and then condensation with the appropriate J-group precursor. Methods for the preparation of the J-3 precursor and the condensation are described in U.S. Pat. No. 5,215,958, WO 90/02120, and U.S. Pat. No. 4,818,275. Methods for the preparation of the J-8 precursor and the condensation with a hydrazine are described in WO 92/12139 and U.S. Pat. No. 4,560,752.

For some compounds of Formulae I and II wherein J=J-2 and Z is $CR^9R^{10}$, the synthesis is carried out as illustrated below in Schemes 9–17. The retrosynthetic analysis for the synthesis of the J-2 group is shown below (Scheme 9). The formation of ring A can be accomplished by intramolecular cyclization between the nitrogen in ring B and the terminal double bond of the triazolinone with the cyclic sulfonamide group already in place.

Scheme 9

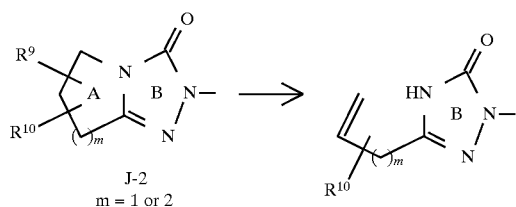

The synthesis of the triazolinone ring B is known in the art and can be prepared by methods such as those described in U.S. Pat. No. 4,818,275 and U.S. Pat. No. 4,818,276.

Acidic condensation of α-ketoacids of Formula 22 and a substituted phenyl hydrazine such as that of Formula 23 gives hydrazones of Formula 24. This reaction is performed under acidic conditions using hydrochloric acid in an organic solvent such as ethyl or methyl alcohol at a temperature between room temperature and about 100° C. Schmidt rearrangement of the acid of Formula 24 with diphenylphosphoryl azide between about 0° C. and about 100° C. followed by a ring cyclization gives the triazolinones as shown below (Scheme 10). The same conditions can be used to form the precursors to compounds of Formula II except the substituted phenyl hydrazine would contain the other cyclic sulfonamide functionality.

Scheme 10

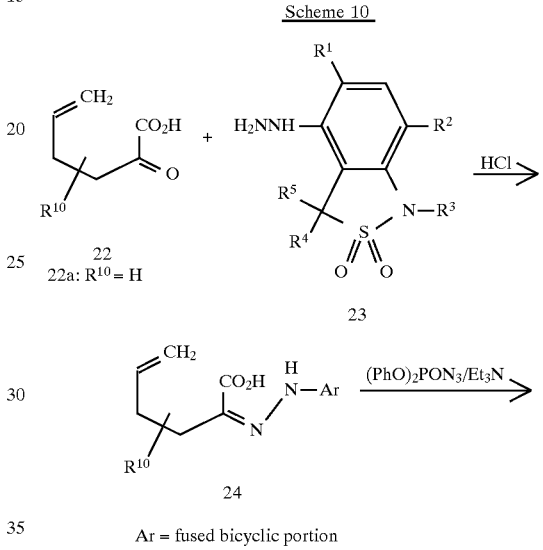

Ar = fused bicyclic portion of Formula 23

For the synthesis of the triazolinones wherein $R^{10}$ is H, 2-oxo-5-hexenoic acid of Formula 22a can be used as the starting material. 2-Oxo-5-hexenoic acid can be made by hydrolysis of the corresponding methyl ester with base, preferably one equivalent of potassium hydroxide in an aqueous alcohol solvent. The ester of 2-oxo-5-hexenoic acid is made from methyl pyruvate as described in *J. Org. Chem.*, (1983), 48, 158.

Treatment of the triazolinone with MCPBA (m-chloroperoxybenzoic acid) in an inert solvent such as dichloromethane at a temperature between about 0° C. and about 100° C., preferably at room temperature, gives an epoxide of Formula 25 (Scheme 11). Intramolecular cyclization of the epoxide using a base such as potassium carbonate in an inert solvent such as acetonitrile or acetone gives the 6-membered ring product of Formula Ic. Fluorination of the alcohol of Formula Ic with DAST (diethylaminosulfur trifluoride) at a temperature between about −78° C. and about 100° C. in an inert solvent such as dichloromethane gives the fluorinated product of Formula Id.

Scheme 11

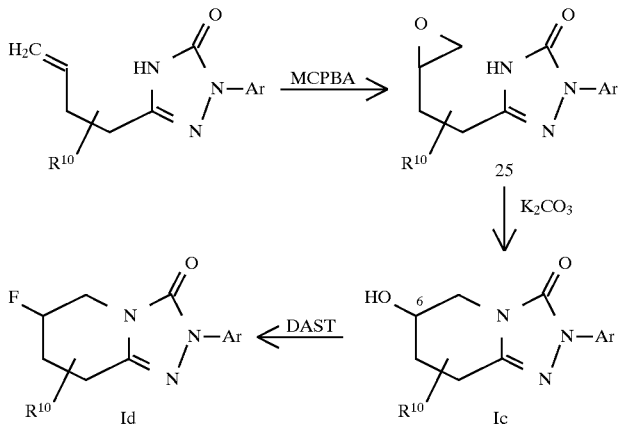

The alcohol of Formula Ic can also be prepared by hydroxybromination of the olefin in the starting triazolinone using N-bromosuccinimide (NBS) and water or N-bromoacetamide and water followed by cyclization of the resulting bromohydrin of Formula 26 using potassium carbonate in an inert solvent such as acetonitrile or acetone (Scheme 12).

Scheme 12

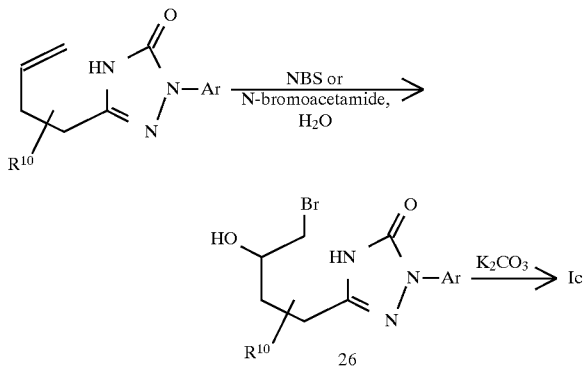

Compounds of Formula Ic can also be converted to the chloro-, bromo-, and iodo-$R^9$ substituted triazolinones of Formula I wherein J=J-2 using methods known to those skilled in the art. For example, the hydroxy group in compounds of Formula Ic can be acylated by known methods to prepare the alkylcarbonyloxy and haloalkylcarbonyloxy derivatives. In addition, the hydroxy or halo group can be converted by known methods to afford the $R^9$=alkoxy and haloalkoxy derivatives (March, J., Advanced Organic Chemistry, (1992), 4th Ed., John Wiley and Sons, Inc., pp 386–389). In fact all the $R^9$=OH or halogen compounds in Schemes 13–17 can be functionalized as is known in the art to prepare the other $R^9$ substituted compounds.

Compounds of Formulae Ie and If can be prepared as illustrated in Scheme 13. Oxidative cleavage of the olefin of the triazolinone using sodium periodate and a catalytic amount of osmium tetroxide in an inert solvent mixture such as tetrahydrofuran (THF) and water, or using ozone in dichloromethane followed by reductive workup using dimethyl sulfide (DMS), affords the aldehyde of Formula 27. Intramolecular cyclization of the aldehyde under basic conditions using potassium carbonate or sodium hydride gives the 5-membered ring alcohol of Formula Ie. Treatment of the alcohol of Formula Ie with DAST in an inert solvent such as dichloromethane at a temperature between about −80° C. and about 60° C. produces the fluoride of Formula If. The fluoride If can also be made by direct cyclization and fluorination using DAST at a temperature range between about −100° C. and about 60° C.

Scheme 13

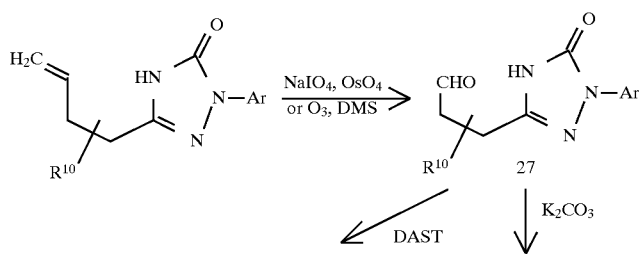

-continued
Scheme 13

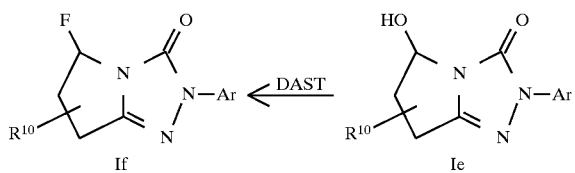

Hydroboration of the olefin of the triazolinone with 9-borabicyclo[3.3.1]nonane (9-BBN) gives the alcohol of Formula 28 after oxidative workup (Scheme 14). Oxidation of alcohol 28 with oxidizing agents such as PDC (pyridinium dichromate) produces the hemiaminal of Formula Ig presumably via the aldehyde intermediate of Formula 29. The fluoro compound of Formula Ih can be made by the treatment of the hemiaminal with DAST.

Scheme 14

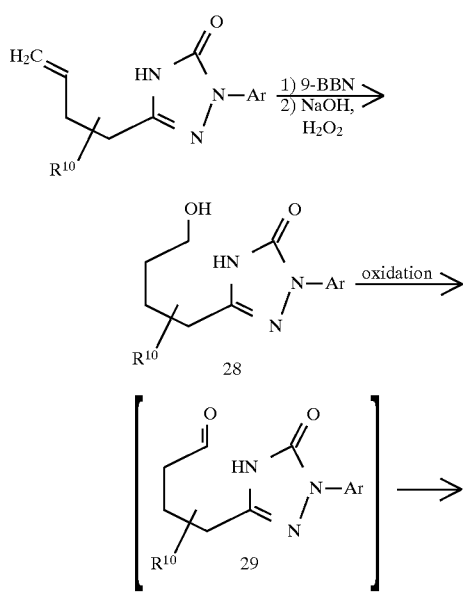

-continued
Scheme 14

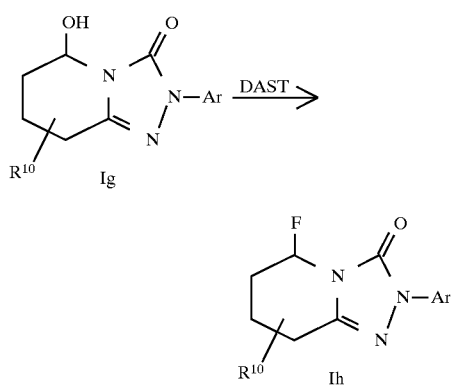

Triazolinones of Formula 30 can be made from 2-oxo-4-pentenoic acids and the substituted phenyl hydrazines by methods known to those skilled in the art and the methods taught herein (Scheme 10). The epoxide of Formula 31 can be prepared from the olefin of Formula 30 using an oxidant such as MCPBA. Intramolecular cyclization of the epoxide with a base such as potassium carbonate affords the alcohol of Formula Ii. The fluoro compound of Formula Ij can be made from the alcohol using DAST at a temperature between about −70° C. and about room temperature in an inert solvent such as dichloromethane.

Scheme 15

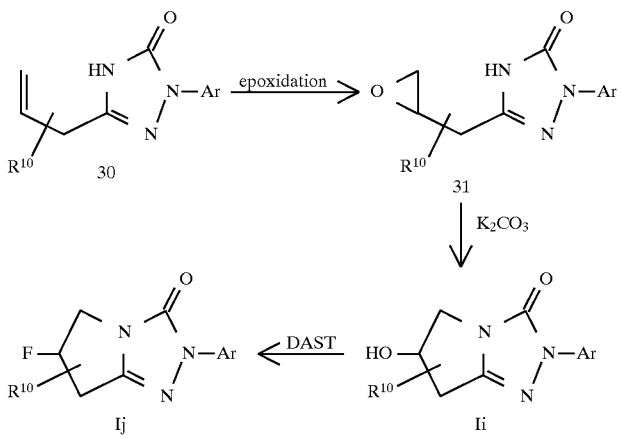

Compounds of Formula Im can be prepared from the unsubstituted compounds of Formula 32 as illustrated in Scheme 16. Treatment of the bicyclic triazolinone of Formula 32 with N-bromosuccinimide (NBS) under allylic bromination conditions affords the mono-bromo derivative of Formula Ik.

Hydrolysis of the bromide in hot aqueous dimethyl sulfoxide ($Me_2SO$) affords the alcohol of Formula Il. The fluoro compound of Formula Im can be prepared by treatment of the alcohol with diethylaminosulfur trifluoride (DAST) as described above.

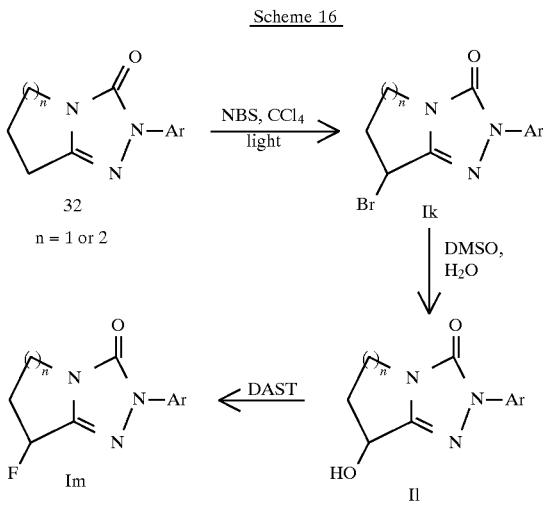

Scheme 16

Compounds of Formula In can be prepared as illustrated in Scheme 17. Allylic oxidation of the terminal alkene of the triazolinone with t-butyl hydroperoxide and catalytic selenium (IV) oxide in an inert solvent such as dichloromethane produces the allylic alcohol of Formula 33. Protection of the secondary alcohol as the t-butyldimethylsilyl (TBS) ether is accomplished using t-butylchlorodimethylsilane and a base, preferably triethylamine and catalytic 4-(dimethylamino) pyridine. The terminal olefin is converted to the primary alcohol to afford compounds of Formula 34 using 9-BBN followed by treatment with sodium perborate. Ring cyclization is accomplished using the Martin sulflirane dehydrating agent $[C_6H_5(CF_3)_2O]_2S(C_6H_5)_2$. Removal of the TBS group and liberation of the alcohol can be accomplished using tetrabutylammonium fluoride. The alcohol can be converted to the corresponding fluoro compound using DAST, or to other $R^9$ substituted compounds as described above.

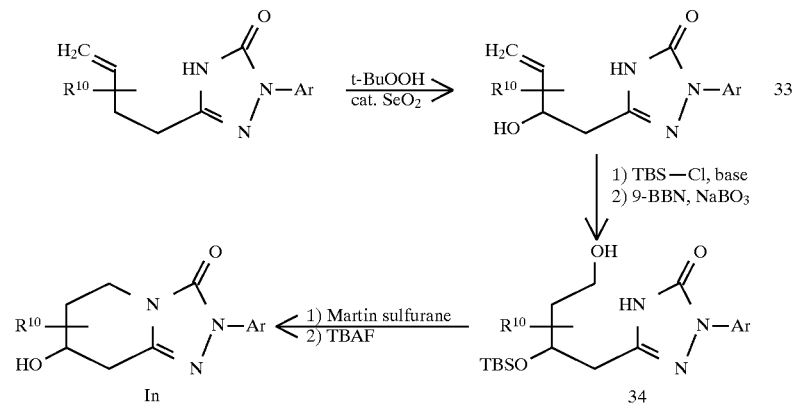

Scheme 17

For some compounds of Formulae I and II wherein J=J-2 and $R^{10}$ is other than hydrogen, the $R^{10}$ substituent is more conveniently introduced after cyclization to form the bicyclic triazolinone. This is especially the case when $R^9$ and $R^{10}$ are attached to the same carbon atom.

Isocyanates

In some instances, the appropriate aniline is first converted to the corresponding isocyanate, and then the isocyanate is condensed with the J-group derivative, or precursor thereof, to form compounds of Formulae I and II. In Scheme 18, the conversion of aniline of Formula 1 to isocyanate of Formula 35 is illustrated. Subsequent condensation of the isocyanate with the aminoester of Formula 36 forms the cyclic sulfonamide of Formula Io. The preparation of some aminoester precursors to J-6 and the condensation procedure is described in U.S. Pat. No. 4,179,276.

Scheme 18

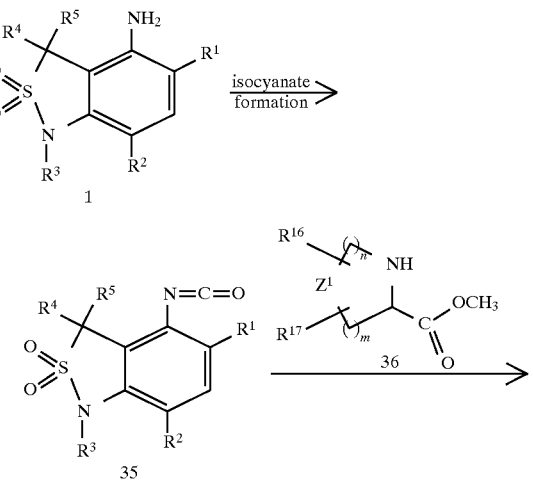

-continued
Scheme 18

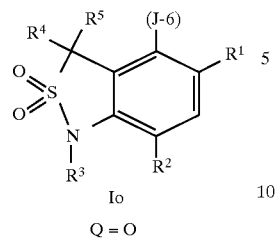

Compounds of Formulae I and II wherein J=J-4, J-5, J-7, J-9, J-11, J-12, J-13, J-14 and J-17 are also prepared by first converting the aniline to the appropriate isocyanate, and then condensation with the appropriate J-group precursor. Methods for the preparation of the J-4 precursor and the condensation are described in WO 92/11244, EP 476,697, ZA 91/00466, JP 77,874, and U.S. Pat. No. 3,902,887. The synthesis of the J-5 precursor and the condensation with isocyanates is described in WO 92/13453 JP 363,278, EP 230,874, and JP 2.000,985. Methods for the preparation of the J-7 precursor and the condensation with isocyanates are described in EP 484,776. Methods for the preparation of the J-9 precursor and the condensation with isocyanates are described in U.S. Pat. No. 5,035,740. Methods for the preparation of the J-17 precursor and its condensation with isocyanates are described in EP 493,323. The synthesis of the J-14 precursor and the condensation with isocyanates is described in *J. Pesticide Sci.,* (1993), 18, 309. In a similar vein, the imino compounds of Formulae I and II wherein J=J-12 and J-13 can be prepared from the corresponding isocyanates of the anilines. The condensation procedure and J-group precursor preparation for compounds containing J-12 and J-13 are disclosed in EP 457,151, JP 4,145,087, EP 480,871 and DE 3,927,388.

One skilled in the art will recognize that when Q or $Q^1$ is S in the desired product, the appropriate isothiocyanate is used instead of the isocyanate in the synthesis.

For some compounds of Formulae I and II wherein J=J-4, J-5, J-6, J-7, J-9, J-14 and J-17, the coupling can also be accomplished starting with the aniline rather than the isocyanate. For example, the synthesis of compounds of Formula Ip (compounds of Formula I wherein $R^{16}$ and $R^{17}$ are taken together to form a cyclopropane ring) is illustrated in Scheme 19.

Scheme 19

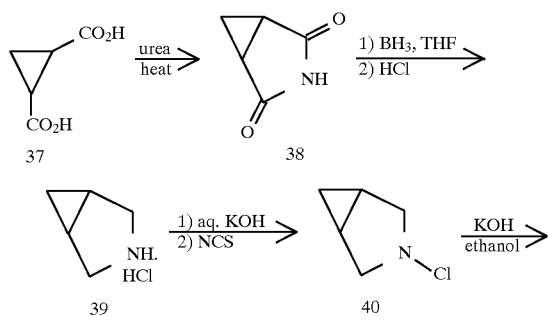

-continued
Scheme 19

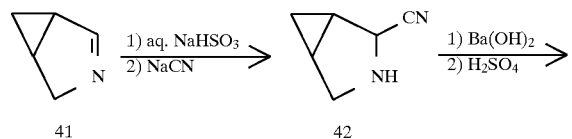

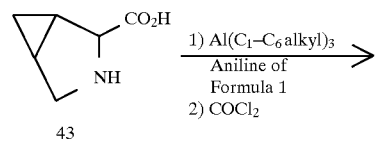

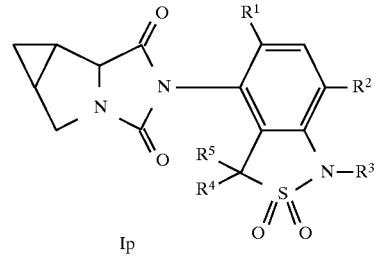

Treatment of cyclopropane dicarboxylic acid of Formula 37 with urea and heating to 175°–185° C. affords the dicarboximide of Formula 38 as described by G. C. Crockett et al. in *Synth. Commun.* (1981), 11, 447–454. The diester of the diacid of Formula 37 is prepared by the method described by L. L. McCoy in *J. Am. Chem. Soc.,* (1958), 80, 65–68. The diacid can be obtained by saponification of the diester using well-known methods. Reduction of the dicarboximide of Formula 38 with borane in an inert solvent, such as tetrahydrofuran (THF), followed by work-up with aqueous hydrochloric acid affords the azabicyclo[3.1.0] hexane hydrochloride of Formula 39. The reduction is preferably conducted with heating, for example in THF at reflux, as described by H. C. Brown and P. Heim in *J. Org. Chem.,* (1973), 38, 912–916.

The amine hydrochloride of Formula 39 is converted via a five step sequence to the α-aminoacid of Formula 43 as illustrated. Purification of the intermediates is not necessary. Neutralization of the amine hydrochloride with a base, such as concentrated aqueous potassium hydroxide, liberates the free amine. Dissolution of the amine in an inert solvent, such as diethyl ether, and treatment with a solution of N-chlorosuccininide (NCS) in an inert solvent such as ether, produces the chloramine of Formula 40. The solution of the chloramine is then treated with ethanolic potassium hydroxide to effect dehydrochlorination and give the imine of Formula 41. Once again, the imine is not purified but treated directly first with aqueous sodium bisulfite, and then with solid sodium cyanide to afford the arninonitrile of Formula 42. The reaction mixture is poured into water and extracted with a water-immiscible solvent such as ether. The organic layers are dried and evaporated under reduced pressure to afford the aminonitrile. No additional purification is necessary. The aminonitrile can be converted to the aminoacid of Formula 43 by hydrolysis with aqueous barium hydroxide followed by neutralization with sulfuric acid. A mixture of epimers at the carboxylic acid centers is obtained, and the individual diastereomers can be separated by chromatography.

The acid of Formula 43 is reacted with the aniline of Formula and a trialkylaluminum reagent (e.g., trimethylaluminum), in a non-coordinating solvent such as an aromatic hydrocarbon (e.g., benzene and toluene) or halogenated hydrocarbon (e.g., methylene chloride, chloroform, carbon tetrachloride, and dichlorobutane) to obtain the amide. Generally, the reaction requires 0.1 to 48 hours at a temperature of 0° C. to 25° C. to proceed to completion. The amides are isolated by extraction into an organic solvent, aqueous wash, and removal of the solvent under reduced pressure. Purification can be accomplished by chromatography or recrystallization. The condensation with the amine can also be performed starting with the ester of the acid of Formula 43.

The tricyclic imide of Formula Ip can be prepared from the α-arninoamide by condensation with phosgene or a phosgene equivalent. Treatment of the α-aminoamide with phosgene is preferably carried out in the presence of a tertiary-amine base such as triethylamine, pyridine, or N,N-diisopropylethylamine, in an inert solvent such as dichloromethane or 1-chlorobutane. The phosgene can be added as a gas or as a solution in an inert solvent such as toluene. Suitable temperatures range from about 0° C. to the reflux temperature of the solvent. 1,1'-Carbonyldiimidazole, diphosgene (ClC(=O)OCCl$_3$) and triphosgene (Cl$_3$COC(=O)OCCl$_3$) can also be used in a similar manner.

The tricyclic imide of Formula Ip can be isolated by extraction into an organic solvent, aqueous wash, and removal of the solvent under reduced pressure. Additional purification can be accomplished by chromatography or recrystallization.

Aryl Iodides

For the preparation of compounds of Formulae I and II wherein J=J-15 and J-16, the appropriate aniline is first converted to the aryl alkyne as illustrated in Scheme 20. The aniline of Formula 1 is converted to the aryl iodide of Formula 44 via diazotization followed by treatment with a metal iodide salt. The aryl iodide is linked by a palladium coupling reaction to give the trimethylsilyl (TMS) alkyne. Hydrolysis of the TMS group with base affords the terminal alkyne of Formula 45. In the case of J-16, a [3+2] cycloaddition using a sydnone as the dipole and the alkyne as the dipolarophile affords the bicyclic pyrazole compounds. Introduction of the R$^{23}$ group affords the cyclic sulfonamides of Formula Iq. For example, treatment with N-chlorosuccinimide affords the R$^{23}$=Cl compound. These methods are described in WO 93/15074.

Scheme 20

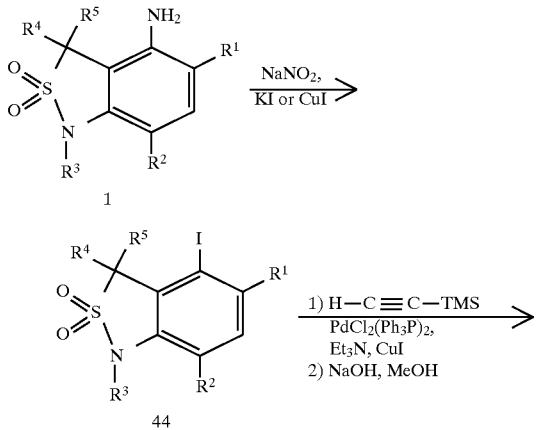

Scheme 20 -continued

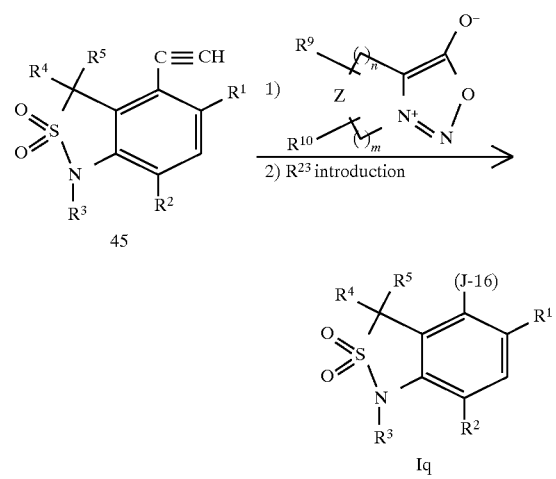

Methods for the similar preparation of compounds of Formulae I and II wherein J=J-15 are described in JP 4,059,706, WO 92/06962, and JP 3,163,063.

For compounds of Formulae I and II wherein J=J-5, the coupling can also be accomplished starting with the aniline rather than the isocyanate. For example, the synthesis of compounds of Formula Ir is illustrated in Scheme 21. Treatment of a diester of Formula 46 with an aniline of Formula 1 in the presence of a trialkylaluminum reagent (e.g., trimethylaluminum) in a non-coordinating solvent such as an aromatic hydrocarbon (e.g., benzene, toluene) or a halogenated hydrocarbon (e.g., methylene chloride, chloroform, carbon tetrachloride and dichlorobutane) affords a compound of Formula Ir.

Scheme 21

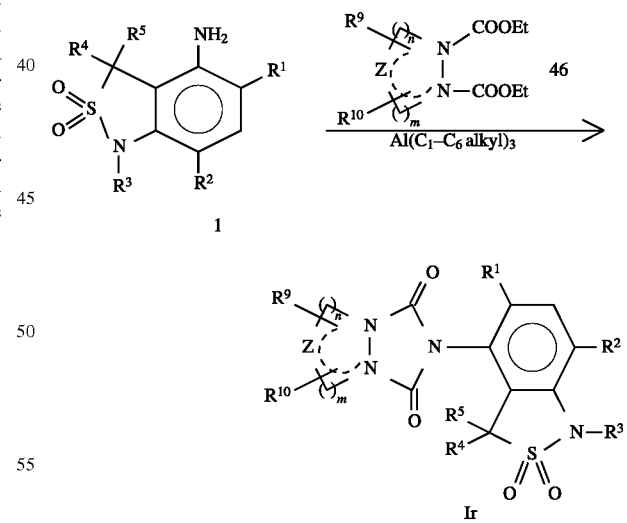

It is recognized that some reagents and reaction conditions described above for preparing compounds of Formulae I and II may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M.

*Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formulae I and II.

One skilled in the art will also recognize that compounds of Formulae I and II and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight unless otherwise indicated. Parts for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, br s=broad singlet.

EXAMPLE 1

Step A

1-Chloro-N-(4-fluoro-3-nitrophenyl) methanesulfonamide

To a solution of 4-fluoro-3-nitroaniline (23.4 g, 0.15 mol) in anhydrous pyridine (120 mL) was added dropwise a solution of chloromethylsulfonyl chloride (22.35 g, 0.15 mol) at 0° C. under a nitrogen atmosphere. The mixture was then stirred at 0°–5° C. for 4 h and then the mixture was poured onto ice (1500 g) containing concentrated aqueous hydrochloric acid (300 mL). The mixture was filtered, and the residue was dissolved in methylene chloride (1200 mL). After drying (MgSO$_4$) and concentration under reduced pressure, the crude product was dissolved in 1-chlorobutane:ether 9:1 v/v and passed through silica gel. The eluent was concentrated under reduced pressure to give the title compound of Step A.

Step B

1-Chloro-N-ethyl-N-(4-fluoro-3-nitrophenyl) methanesulfonamide

A solution of 1-chloro-N-(4-fluoro-3-nitrophenyl) methanesulfonamide (5.93 g, 22.1 mmol), iodoethane (3.79 g, 24.3 mmol), tetrabutylammonium bromide (0.712 g, 2.21 mmol), and anhydrous K$_2$CO$_3$ (8.85 g, 64 mmol) in anhydrous dimethylformamide (40 mL) was stirred at room temperature. When the starting material had disappeared based on thin layer chromatography on silica (6 h), the reaction mixture was poured into water (200 mL) and extracted with CH$_2$Cl$_2$ (500 mL). The organic extract was washed with water (two times with 50 mL), dried (MgSO$_4$), and the solvent was removed under reduced pressure. The residue was purified by flash chromatography (silica gel, 1-chlorobutane and diethyl ether 100:1 v/v eluent) to give 4.68 g of the title compound of Step B as a solid melting at 80°–83° C. $^1$H NMR (Me$_2$SO-d$_6$, 400 MHz): δ 8.17 (dd,1H, J=6.75 and 2.7 Hz), 7.85 (dd,1H, J=9.4 and 3 Hz), 7.69 (dd,1H, J=11 and 9 Hz), 5.25 (s,2H), 3.83 (q,2H), 1.04 (t,3H).

Step C

1-Ethyl-5-fluoro-1,3-dihydro-4-nitro-2,1-benzisothiazole2,2-dioxide and 1-Ethyl-6-fluoro-1,3-dihydro-5-nitro-2,1-benzisothiazole 2,2-dioxide 1-Chloro-N-ethyl-N-(4-fluoro-3-nitrophenyl) methanesulfonamide (2.0 g, 6.74 mmol) in dimethyl sulfoxide (Me$_2$SO-d$_6$, 10 mL) was added dropwise to a vigorously stirred suspension of powdered NaOH (4.0 g) in Me$_2$SO-d$_6$ (30 mL) while maintaining the temperature at 25°–27° C. after completion of the addition, the mixture was stirred at 25°–27° C. for an additional 30 min. After completion of the reaction based on thin layer chromatography on silica gel, the reaction mixture was poured into ice (400 g) and concentrated aqueous hydrochloric acid (60 mL). The precipitate was extracted into CH$_2$Cl$_2$ (300 mL), dried (MgSO$_4$), and subjected to flash chromatography on silica gel using ethyl acetate:hexane 1:4 v/v. Two products were isolated. The first compound to elute was 1-ethyl-6-fluoro-1,3-dihydro-5-nitro-2,1-benzisothiazole 2,2-dioxide (Compound A, 120 mg). The second compound to elute was 1-ethyl-5-fluoro-1,3-dihydro-4-nitro-2,1-benzisothiazole 2,2-dioxide (Compound B, 976 mg). Compound A: $^1$H NMR (CDCl$_3$, 300 MHz): δ 7.33 (dd,1H, J=10.51 and 9.75 Hz), 6.96 (dd,1H, J=9.0 and 3.38 Hz), 4.63 (s,2H), 3.76 (q,2H), 1.41 (t,3H). Compound B: m.p. 97°–100° C.; $^1$H NMR (CDCl$_3$, 300 MHz): δ 7.37 (d,1H, J=6.10 Hz), 7.27 (d,1H, J=10.9 Hz), 4.39 (s,2H), 3.74 (q,2H), 1.44 (t,3H).

Step D:

1-Ethyl-5-fluoro-1,3-dihydro-2,1-benzisothiazol-4-amine 2,2-dioxide

A mixture of 1-ethyl-5-fluoro-1,3-dihydro-4-nitro-2,1-benzisothiazole 2,2-dioxide (1.0 g, 3.8 mmol) and SnCl$_2$.H$_2$O (4.34 g, 19.2 mmol) in ethyl acetate (50 mL) was heated at reflux for 3 h. After completion of the reaction based on thin layer chromatography, the mixture was diluted with ethyl acetate (100 mL) and solid Na$_2$CO$_3$ (12.5 g) was added. The resulting mixture was vigorously stirred for 12 h and then filtered through a pad of diatomaceous earth (Celite®). The filtrate was then evaporated under reduced pressure, and the residue was subjected to flash chromatography (silica gel, chlorobutane:ether 1:10 v/v) to give 650 mg of the title compound of Step D. $^1$H NMR (CDCl$_3$, 400 MHz): δ 6.94 (m,1H), 6.08 (m,1H), 4.10 (s,2H), 3.80 (br s,2H), 3.62 (q,2H), 1.36 (t,3H).

Step E:

2-(1-Ethyl-5-fluoro-1,3-dihydro-2,1-benzisothiazole-4-yl)-4,5,6,7-tetrahydro-1H-isoindole-1,3(2H)-dione S,S-dioxide A mixture of 1-ethyl-5-fluoro-1,3-dihydro-2,1-benzisothiazol-4-amine 2,2-dioxide (506 mg, 2.2 mmol), and 3,4,5,6-tetrahydrophthalic anhydride (335 mg, 2.2 mmol) in acetic acid (10 mL) was heated at reflux for 2 days. Progress of the reaction was monitored by thin layer chromatography. After completion of the reaction, the solvent was removed under reduced pressure and the product was purified by flash chromatography (silica gel, 1-chlorobutane:ether 4:1 v/v) to give 550 mg of the title compound of Step E, a compound of the invention, as a solid melting at 189°–190° C. $^1$H NMR (CDCl$_3$, 400 MHz): δ 7.18 (dd,1H), 6.72 (dd,1H), 4.20 (s,2H), 3.68 (q,2H), 2.42 (br s,4H), 1.78 (br s,4H), 1.38 (t,3H).

EXAMPLE 2

2-(7-Chloro-1-ethyl-5-fluoro-1,3-dihydro-2,1-benzisothiazol-4-yl)-4,5,6,7-tetrahydro-1H-isoindole-1,3(2H)-dione S,S-dioxide A mixture of 2-(1-ethyl-5-fluoro-1,3-dihydro-2,1-benzisothiazole-4-yl)-4,5,6,7-tetrahydro-1H-isoindole-1,3(2H)-dione S,S-dioxide (250 mg, 0.686 mmol) and N-chlorosuccinimide (96 mg, 0.72 mmol) in dimethylformamide (3 mL) was heated at 80° C. for 4 h under a nitrogen atmosphere. After completion of the reaction based on thin layer chromatography, the mixture was poured into ether (25 mL) and water (5 mL). The organic phase was separated, dried (MgSO$_4$) and evaporated under reduced pressure. The residue was then purified by flash chromatography (silica gel, 1-chlorobutane:ether 19:1 v/v as eluent) to give 121 mg of the title compound of Example 2, a compound of the invention, as a solid melting at 190°–192° C. $^1$H NMR (CDCl$_3$, 400 MHz): δ 7.26 (dd,1H), 4.18 (s,2H), 3.96 (q,2H), 2.45 (m,4H), 1.84 (m,4H), 1.28 (t,3H).

EXAMPLE 3

Step A

1-Ethyl-6-fluoro-1,3-dihydro-2,1-benzisothiazol-5-amine 2,2-dioxide

1-Ethyl-6-fluoro-1,3-dihydro-5-nitro-2,1-benzisothiazole 2,2-dioxide (Compound B from Example 1, Step C, 1.0 g), was suspended in tetrahydrofuran (20 mL) with 10% palladium on carbon (100 mg). The suspension was placed in Parr® shaker and treated with 50 psi (3.45×10$^5$ Pa) of hydrogen overnight. The catalyst was then filtered off through diatomaceous earth (Celite®), and the filtrate was evaporated under reduced pressure to give the title compound of Step A as a brown solid (0.510 mg). $^1$H NMR (CDCl$_3$): δ 6.92 (dd,1H), 6.04 (dd,1H), 4.08 (s,2H), 3.80 (br s,2H), 3.64 (q,2H), 1.32 (t,3H).

Step B

2-(1-Ethyl-5-fluoro-1,3-dihydro-2,1-benzisothiazol-6-yl)-4,5,6,7-tetrahydro-1H-isoindole-1,3(2H)-dione S,S-dioxide 1-Ethyl-6-fluoro-1,3-dihydro-2,1-benzisothiazol-5-amine 2,2-dioxide (123 mg) and 3,4,5,6-tetrahydrophthalic anhydride (64 mg) were condensed using the procedure described in Example 1, Step E to give 64 mg of the title compound of Step B, a compound of the invention. $^1$H NMR (CDCl$_3$): δ 7.08 (d,1H), 6.62 (d,2H), 4.32 (s,2H), 3.64 (q,2H), 2.42 (m,4H), 1.82 (m,4H), 1.38 (t,3H).

EXAMPLE 4

Step A

7-Chloro-1-ethyl-5-fluoro-1,3-dihydro-4-isocyanato-2,1-benzisothiazole 2,2-dioxide To a mixture of 7-chloro-1-ethyl-5-fluoro-1,3-dihydro-2,1-benzisothiazol-4-amine-2,2-dioxide (1.30 g, 4.91 mmol), diphosgene (1.17 g, 1.2 eq) in p-dioxane (20 mL), triethylamine (0.6 g, 1.2 eq) was added and the resulting reaction mixture was heated at reflux for overnight. The precipitated triethylamine hydrochloride was filtered off and the solvents were removed in vacuo and dried to give the title compound of Step A as a brown semisolid. $^1$H NMR (CDCl$_3$, 400 MHz): δ 7.21 (d,1H, J=9.5 Hz), 4.28 (s,2H), 3.94 (q,2H), 1.22 (t,3H, J=7.5 Hz).

Step B

3-(7-Chloro-1-ethyl-5-fluoro-1,3-dihydro-2,1-benzisothiazole-4-yl)-6-(trifluoromethyl)-2.4(1H, 3H)-pyrimidinedione S,S-dioxide A solution of ethyl 3-amino-4,4,4-trifluorocrotonate (0.899 g, 4.91 mmol) in DMF (3 mL) was added to sodium hydride (60% suspension in oil, 0.118 g, 4.91 mmol) in DMF (8.5 mL) at −10 to −5° C. The reaction mixture was stirred at −10 to −5° C. for 30 min and was then cooled to −78° C. To the resulting solution was added a solution of the title compound of Step A in toluene (14 mL). The reaction mixture was stirred for an additional 2 h at −78° C., overnight at room temperature, and was then poured into HCl/ice mixture and extracted with ethyl acetate (20 mL). The organic phase was separated, washed with water (10 mL), dried (MgSO$_4$), filtered and the solvent was removed on the rotary evaporator. The title compound of Step B, a compound of the invention, was isolated by flash chromatography as a brown solid (1.18 g, m.p. >230° C., R$_f$ 0.25 (silica gel) 1:1 1-chlorobutane and ether). $^1$H NMR (Me$_2$SO-d$_6$, 400 MHz): δ 12.92 (broad, 1H, NH), 7.83 (d,1H, 10.0 Hz), 6.46 (s,1H), 4.76 (d,1H, J=16.5 Hz), 4.58 (d,1H, J=16.5 Hz), 3.81 (q,2H), 1.17 (t,3H, J=7.0 Hz).

EXAMPLE 5

3-(7-Chloro-1-ethyl-5-fluoro-1,3-dihydro-2,1-benzisothiazol-4-yl)-1-methyl-6-(trifluoromethyl)-2,4(1H,3H)-pyrimidinedione S,S-dioxide A mixture of the title compound of Step B in Example 4 (0.33 g, 077 mmol), dimethyl sulfate (0.102 g, 1.05 eq) in acetone (10 mL) was heated at reflux in the presence of potassium carbonate (0.213 g) for 3 h. After completion of the reaction (TLC), the reaction mixture was cooled, the insolubles were filtered off and the solvent was removed on a rotary evaporator. The title compound of Example 5, a compound of the invention, was purified by flash chromatography to give a colorless solid melting at 147°–149° C. (R$_f$ 0.55, 1:1 1-chlorobutane and ether). $^1$H NMR (benzene-d$_6$, 400 MHz): δ 6.55 (d,1H, J=9.5 Hz), 5.86 (s,1H), 3.19–3.60 (m,4H), 2.77 (d,1H, J=1.5 Hz), 0.963 (t,3H). IR (KBr) 1636, 1691.

EXAMPLE 6

3-(7-Chloro-1-ethyl-5-fluoro-1,3-dihydro-2,1-benzisothiazol-4-yl)-1-ethyl-6-(trifluoromethyl)-2,4 (1H,3H)-pyrimidinedione S,S-dioxide A mixture of the title compound of Step B in Example 4 (0.3 g, 0.70 mmol), ethyl iodide (0.13 g, 0.84 mmol), K$_2$CO$_3$ (0.12 g, 0.88 mmol) in acetone (10 mL) was heated at reflux for 40 h. The reaction mixture was cooled, the insolubles were filtered off, the solvent was removed in vacuo and the title compound of Example 6, a compound of the invention, was purified by flash chromatography to give a solid melting at 177°–178° C. $^1$H NMR: δ 7.24 (d,1H), 6.32 (s,1H), 4.08 (s,2H), 4.04 (m,4H), 1.26 (m,6H).

EXAMPLE 7

Step A

7-Chloro-1-ethyl-5-fluoro-1,3-dihydro-4-isothiocyanato-2,1-benzisothiazole 2,2-dioxide To a solution of 7-chloro-1-ethyl-5-fluoro-1,3-dihydro-2,1-benzisothiazol-4-amine 2,2-dioxide (0.5 g, 1.88 mmol) and triethylamine (0.6 mL) in anhydrous tetrahydrofuran (THF, 10 mL), thiophosgene (0.238 g, 1.1 eq) in THF (2 mL) was added dropwise at room temperature under a nitrogen atmosphere. The resulting reaction mixture was heated at reflux for 2 days. The solvents were removed in vacuo to give the title compound of Step A which was used in Step B.

Step B

3-[(7-Chloro-1-ethyl-5-fluoro-1,3-dihydro-2,1-benzisothiazol-4-yl)imino]tetrahydro-1H,3H-[1,3,4]thiadiazolo[3,4-α]pyridazin-1-one S,S-dioxide A mixture of the title compound of Step A (0.57 g, 1.88 mmol), 1,2,3,6-tetrahydropyridazine (0.675 g, 1.97 mmol)

and K₂CO₃ (1.3 g, 5 eq) in anhydrous THF was stirred at room temperature for 1 h. After completion of the reaction, the solvent was removed and the adduct was purified by flash chromatography. ¹H NMR (CDCl₃, 300 MHz): δ 9.28 (br s,1H),7.08 (d,1H), 4.21 (s,2H),3.86 (m,3H),3.56 (m,1H), 3.04 (m,2H ), 1.82 (m,4H), 1.26 (t,3H).

To a solution of this adduct (0.342 g, 0.87 mmol) in anhydrous toluene (5 mL) was added a solution of phosgene (0.098 g) in toluene (3 mL) dropwise under a nitrogen atmosphere and the resulting reaction mixture was stirred at room temperature for 12 h. After completion of the reaction (TLC), the solvent was removed under reduced pressure and the title compound of Step B, a compound of the invention, was purified by flash chromatography to give a solid melting at 143°–146° C. ¹H NMR (CDCl₃, 300 MHz): δ 7.03 (d,1H, 10.8 Hz), 4.16 (s,2H), 3.90 (dd,2H), 3.47 (m,4H), 1.93 (m,4H), 1.20 (t,3H).

EXAMPLE 8

2-(7-Chloro-1-ethyl-5-fluoro-1,3-dihydro-2,1-benzisothiazol-4-yl)tetrahydroimidazo [1,5α] pyridine-1,3(2H,5H)-dione S,S-dioxide To a solution of pipecolinic acid (0.205 g, 1.59 mmol) in KOH (93 mg, 1.66 mmol), H₂O (5 mL) was added the title compound of Step A in Example 4 (0.44 g, 1.5 mmol) in acetone (2.5 mL). The resulting reaction mixture was stirred at room temperature for 20 h. The solvents were then removed and acidified with 3N HCl to pH 1 to obtain a brown precipitate. The mixture was extracted with ethyl acetate (50 mL) and the organic phase was separated. The organic phase was dried (MgSO₄) and the solvent was removed to give a brown solid. This solid was dissolved in ethanol (10 mL) and 3N HCl (10 mL) and heated at reflux for 12 h. The solvents were then removed in vacuo and the residue was extracted with ethyl acetate. The extracts were dried (MgSO₄) and concentrated to give a brown solid. The title compound of Example 8, a compound of the invention, was isolated by flash chromatography using ethyl acetate: hexane (3:7) as eluent giving a solid melting at 168°–169° C. ¹H NMR (CDCl₃, 400 MHz): δ 7.28 (d,1H, J=9.5 Hz), 4.17–4.36 (m,3H), 3.94 (m,3H), 2.93 (m,1H), 2.32 (m,1H), 2.09 (m,1H), 1.83 (m,1H), 1.40–1.55 (m,3H), 1.28 (t,3H).

EXAMPLE 9

2-(7-Chloro-1-ethyl-5-fluoro-1,3-dihydro-2,1-benzisothiazol-4-yl)tetrahydro-1H-imidazo-[5,1-c][1,4]oxazine-1,3(2H)-dione S,S-dioxide Using similar reaction conditions as described in Example 8, the title compound of Step A in Example 4 (0.44 g, 1.5 mmol) and morpholine carboxylic acid (0.218 g, 1.66 mmol) gave 0.24 g of the title compound of Example 9, a compound of the invention, as a solid melting at 200°–202° C. ¹H NMR (CDCl₃, 400 MHz): δ 7.27 (d,1H, J=9.5 Hz), 4.36 (m,2H), 4.25 (d,1H), 4.17 (m,1H), 4.03 (m,2H),3.96 (m,2H) , 3.23–3.53 (m,3H), 1.28 (t,3H).

EXAMPLE 10

2-(7-Chloro-1-ethyl-5-fluoro-1,3-dihydro-2,1-benzisothiazol-4-yl)-5,8-dihydro-1H-[1,2,4]triazolo [1,2-α]pyridazine-1,3(2H)-dione S,S-dioxide A solution of trimethylaluminum (0.68 mL 2M in hexane, 1.36 mmol) was added dropwise to 7-chloro-1-ethyl-5-fluoro-1,3-dihydro-2,1-benzisothiazol-4-amine 2,2-dioxide (0.3 g, 1.13 mmol) in toluene (5 mL) at room temperature under a nitrogen atmosphere and the resulting reaction mixture was stirred for 10 min. A solution of diethyl 3,6-dihydro-1,2-pyridazinedicarboxylate (0.313 g, 1.36 mmol) in toluene (2 mL) was then added at room temperature and the reaction mixture was heated at reflux for 12 h. After the reaction was complete, the reaction mixture was poured into a solution of ethyl acetate (40 mL) containing 1N HCl (10 mL) and stirred for 10 min. The organic phase was separated, dried, and the solvent was removed on a rotary evaporator and followed by flash chromatography to afford the title compound of Example 10, a compound of the invention, as a semisolid. ¹H NMR (CDCl₃, 300 MHz): δ 7.30 (d,1H, J=9.6 Hz), 5.99 (s,2H), 4.31 (s,2H), 4.21 (s,4H), 3.93 (dd,2H), 1.28 (t,3H).

EXAMPLE 11

2-(7-Chloro-1-ethyl-5-fluoro-1,3-dihydro-2,1-benzisothiazol-4-yl)tetrahydro-1H-[1,2,4]triazolo[1,2-α]pyridazine-1,3(2H)-dione S,S-dioxide Using similar reaction conditions as described in Example 10,7-chloro-1-ethyl-5-fluoro-1,3-dihydro-2,1-benzisothiazol-4-amine 2,2-dioxide (0.46 g, 1.13 mmol) and diethyl hexahydropyridazine-1,2-dicarboxylate (0.314 g, 1.36 mmol) gave the title compound of Example 11, a compound of the invention, as a solid melting at 87°–90° C. ¹H NMR (CDCl₃,400 MHz):δ7.29 (d,1H), 4.22 (s,2H), 3.95 (q,2H), 3.65 (m,4H), 1.89 (m,4H), 1.28 (t,3H).

EXAMPLE 12

Step A

7-Chloro-1-ethyl-5-fluoro-4-hydrazino-1,3-dihydro-2,1-benzisothiazole 2,2-dioxide To a suspension of 7-chloro-1-ethyl-5-fluoro-1,3-dihydro-2,1-benzisothiazol-4-amine 2,2-dioxide (0.5 g, 1.89 mmol) in water (3.1 mL) and H₂SO₄ (1.65 mL) at 0° C. was added NaNO₂ (0.13 g, 1.89 mmol) in water (0.5 mL). The reaction mixture was stirred at 0° C. for 1 h. A solution of SnCL₂.H₂O (0.85 g, 3.78 mmol) in conc. HCl (3.1 mL) was then added dropwise and the reaction mixture was stirred at room temperature for 12 h. Then 50% aqueous NaOH solution was added until the reaction mixture reached pH 13. The reaction mixture was extracted with ethyl acetate (200 mL) and the organic layer was washed with brine (3×50 mL) and dried (MgSO₄). The solvent was removed and the title compound of Step A was isolated by flash chromatography. ¹H NMR (CDCl₃, 300 MHz): δ 7.04 (d,1H), 5.62 (br s,1H), 4.62 (s,2H), 3.86 (m,2H), 1.26 (t,3H).

Step B

A mixture of the title compound of Step A (0.5 g, 1.79 mmol), aqueous HCl (10%, 0.1 mL), ethanol (0.2 mL) and sodium pyruvate (0.21 g, 1.87 mmol) was heated at 40° C. for 1 h. The reaction mixture was then cooled and diluted with water (2 mL) to give a brown solid which was filtered (0.5 g) and used in Step C.

Step C 1-(7-Chloro-1-ethyl-5-fluoro-1,3-dihydro-2,1-benzisothiazol-4-yl)-2,4-dihydro-5-methyl-3H-1,2,4-triazol-3-one S,S-dioxide A mixture of the Step B compound (0.78 g, 2.23 mmol), diphenylphosphoryl azide (0.62 g, 2.25 mmol) and triethylamine (0.24 g, 2.32 mmol) in anhydrous toluene (11 mL) was heated at reflux for 5 h. After completion of the reaction (TLC), the reaction mixture was cooled, diluted with ethyl acetate (50 mL) and washed with brine (10 mL). The organic phase was dried (MgSO$_4$) and the solvent was evaporated. The resulting residue was purified by flash chromatography to give the title compound of Step C as a solid melting at 195°–197° C. $^1$H NMR (Me$_2$SO-d$_6$, 400 MHz): δ 11.92 (br s,1H), 7.79 (d,1H, J=10.25 Hz), 4.71 (s,2H), 3.78 (dd,2H), 2.15 (s,3H), 1.15 (t,3H).

Step D 2-(7-Chloro-1-ethyl-5-fluoro-1,3-dihydro-2,1-benzisothiazol-4-yl)-4-(difluoromethyl)-2,4-dihydro-5-methyl-3H- 1,2,4-triazol-3-one S,S-dioxide To a mixture of the title compound of Step C (0.348 g, 1 mmol), tetrabutylammonium bromide (TBAB, 0.25 g), NaOH (0.257 g, 6.43 mmol) in cyclohexane (10 mL) was added Freon® 22 (chlorodifluoromethane, 0.3 mL, 2.98 mmol) and the reaction mixture was heated at 60° C. for 2 h under a Freon® 22 filled balloon. After the reaction was complete, the reaction mixture was cooled and the solvent was removed. The title compound of Step D, a compound of the invention, was isolated by flash chromatography as a semisolid. $^1$H NMR (CDCl$_3$, 300 MHz): δ 7.32 (d,1H), 7.02 (t,1H), 4.26 (s,2H), 3.96 (q,2H), 2.49 (s,3H), 1.26 (t,3H).

EXAMPLE 13

Step A

1-Chloro-N-(4-fluoro-3-nitrophenyl)-N-[(4-methoxphenyl)methyl]methanesulfonamide A solution of the title compound of Step A in Example 1 (3 g, 11.16 mmol), 4-methoxbenzyl chloride (2.1 g, 13.4 mmol), tetrabutylammonium bromide (0.36 g, 1.1 mmol) and anhydrous K$_2$CO$_3$ (4.5 g, 13.8 mmol) in anhydrous dimethylformamide (20 mL) was stirred at room temperature for 6 h. When the starting material had been consumed based on TLC (silica gel), the reaction mixture was poured into water (100 mL) and extracted with ethyl acetate (250 mL). The organic extract was washed with brine (100 mL), dried (MgSO$_4$), and the solvent was removed. Flash chromatography of the residue afforded 2.5 g of the title compound of Step A as an oil. $^1$H NMR (CDCl$_3$, 300 MHz): δ 8.01 (dd,1H, J=6.57 and 2.82 Hz), 7.48 (m,1H), 7.21 (dd,1H, J=10.13, 9.01 Hz), 6.80–7.12 (m,4H), 4.93 (s,2H), 4.57 (s,2H), 3.77 (s,3H).

Step B

5-Fluoro-1,3-dihydro-1-[(4-methoxphenyl)methyl]-4-nitro-2,1-benzisothiazole 2,2-dioxide and 5-fluoro-1,3-dihydro-1-[(4-methoxphenyl)methyl]-6-nitro-2,1-benzisothiazole 2,2-dioxide The title compound of Step A (1.66 g, 4.26 mmol) in dimethyl sulfoxide (Me$_2$SO, 8 mL) was added dropwise to a vigorously stirred suspension of powdered NaOH (3.32 g) in Me$_2$SO (15 mL) while maintaining the temperature at 25°–27° C. After completion of the addition, the reaction mixture was stirred at 25°–27° C. for an additional 45 min. The reaction mixture was then poured into a mixture of ice (600 g) and conc. HCl (40 mL) and extracted with ethyl acetate (300 mL). The organic extract was dried (MgSO$_4$) and the solvent was removed. Flash chromatography of the resulting residue afforded two products. The first compound to elute was 5-fluoro-1,3-dihydro-1-[(4-methoxphenyl)methyl]-6-nitro-2,1-benzisothiazole 2,2-dioxide (Compound A). The second compound to elute was 5-fluoro-1,3-dihydro-1-[(4-methoxyphenyl)methyl]-4-nitro-2,1-benzisothiazole 2,2-dioxide (Compound B). Compound A: $^1$H NMR (CDCl$_3$, 400 MHz): δ 7.26 (m,3H), 6.88 (m,3H), 4.68 (s,2H), 4.46 (s,2H), 3.82 (s,3H). Compound B: $^1$H NMR (CDCl$_3$, 400 MHz): δ 7.30 (d,2H), 7.16 (t,1H, J=10 Hz), 6.90 (d,2H), 6.74 (dd,1H, J=9.0, 3.5 Hz), 4.73 (d,2H, J=4.5 Hz), 3.80 (s,3H).

Step C

5-Fluoro-1,3-dihydro-1-[(4-methoxphenyl)methyl]-2,1-benzisothiazol-4-amine 2,2-dioxide A mixture of 5-fluoro-1,3-dihydro-1-[(4-methoxyphenyl)methyl]-4-nitro-2,1-benzisothiazole 2,2-dioxide (1.54 g, 4.37 mmol) and SnCl$_2$.H$_2$O (4.93 g, 21.9 mmol) in ethyl acetate (200 mL) was heated at reflux for 3 h. Then the reaction mixture was cooled, diluted with ethyl acetate (200 mL) and solid Na$_2$CO$_3$ (15 g) was added. The resulting mixture was vigorously stirred for 12 h and filtered through a pad of diatomaceous earth (Celite®). The filtrate was concentrated and the residue was subjected to flash chromatography to give 1.35 g of the title compound of Step C as brown solid melting at 154°–157° C. $^1$H NMR (CDCl$_3$, 400 MHz): δ 7.33 (d,2H), 6.87 (d,2H), 6.82 (dd,1H, J=11.3 and 8.75 Hz), 5.91 (dd,1H, J=8.5 and 3.5 Hz), 4.65 (s,2H), 4.22 (s,2H), 3.79 (s,3H), 3.75 (br s,2H).

Step D

7-Chloro-5-fluoro-1,3-dihydro-1-[(4-methoxphenyl)methyl]-2,1-benzisothiazol-4-amine 2,2-dioxide A mixture of the title compound of Step C (0.387 g, 1.2 mmol) and N-chlorosuccinimide (0.168 g, 1.26 mmol) in dimethylformamide (6 mL) was heated at 80° C. for 4 h. After completion of the reaction, the mixture was poured into a mixture of ether (25 mL) and water (10 mL). The organic phase was separated, dried (MgSO$_4$) and the solvent was removed on a rotary evaporator. Flash chromatography of the resulting residue afforded 0.4 g of the title compound of Step D. $^1$H NMR (CDCl$_3$, 400 MHz): δ 7.23 (d,2H), 7.03 (d,1H), 6.74 (d,2H), 4.93 (s,2H), 3.84 (s,2H), 3.75 (s,3H).

Step E

2-[7-Chloro-5-fluoro-1,3-dihydro-1-[(4-methoxyphenyl)methyl]-2,1-benzisothiazol-4-yl]4,5,6,7-tetrahydro-1 H-isoindole-1,3(2H)-dione S,S-dioxide and 2-(7-chloro-5-fluoro-1,3-dihydro-2,1-benzisothiazol-4-yl)-4,5,6,7-tetrahydro-1H-isoindole-1,3(2H)-dione S,S-dioxide A mixture of the title compound of Step D (0.43 g, 1.2 mmol) and 3,4,5,6-tetrahydrophthalic anhydride (0.183 g, 1.2 mmol) in acetic acid (10 mL) was heated at reflux for 36 h. The solvent was then removed under reduced pressure and flash chromatography using 1-chlorobutane:ether (9:1) as eluent gave two compounds. 2-[7-Chloro-5-fluoro-1,3-dihydro-1-[(4-methoxyphenyl)methyl]-2,1-benzisothiazol-4-yl)-4,5,6,7-tetrahydro-1H-isoindole-1,3 (2H)-dione S,S-dioxide, a compound of the invention, was eluted first as a solid melting at 171°–174° C. $^1$H NMR (CDCl$_3$, 300 MHz): δ 7.22–7.27 (m,3H), 6.80 (dd,2H, J=8.63 and 2.06 Hz), 4.98 (s,2H), 3.99 (s,2H), 3.77 (s,3H), 2.41 (m,4H), 1.81 (m,4H). 2-(7-Chloro-5-fluoro-1,3-dihydro-2,1-benzisothiazol-4-yl)-4,5,6,7-tetrahydro-1H-isoindole-1,3(2H)-dione S,S-dioxide, a compound of the invention, was eluted second as a solid melting at 75°–79° C. $^1$H NMR (CDCl$_3$, 300 MHz): δ 7.21 (d,1H, 9.38 Hz), 7.13 (br s,1H), 4.38 (s,2H), 2.44 (m,4H), 1.84 (m,4H).

EXAMPLE 14

2-(1-Acetyl-7-chloro-5-fluoro-1,3-dihydro-2,1-benzisothiazol-4-yl)-4,5,6,7-tetrahydro- 1H-isoindole-1,3(2H)-dione S,S-dioxide To a solution of 2-(7-chloro-5-fluoro-1,3-dihydro-2,1-benzisothiazol-4-yl)-4,5,6,7-tetrahydro-1H-isoindole-1,3-

(2H)-dione S,S-dioxide (0.208 g, 0.56 mmol) and Et₃N (0.5 mL) in anhydrous tetrahydrofuran (5 mL) was added acetyl chloride (50 mg, 0.044 mmol) dropwise at 0° C. The reaction mixture was then stirred at room temperature for 4 h. After the reaction was complete (TLC), the solvent was removed and the title compound of Example 14, a compound of the invention, was isolated by flash chromatography as a solid melting at 205°–208° C. ¹H NMR (CDCl₃, 300 MHz): δ 7.37 (d,1H, J=9.57 Hz), 4.38 (s,2H), 2.59 (s,3H), 2.44 (m,4H) and 1.84 (m,4H).

EXAMPLE 15

Step A

7-Chloro-5-fluoro-1,3-dihydro-4-isocyanato-1-[(4-methoxphenyl)methyl]-2,1-benzisothiazol 2,2-dioxide Following the procedures described in Step A in Example 4 using the title compound of Step D in Example 13 (0.68 g, 2 mmol), diphosgene (2.2 mmol) and triethylamine (3 mmol) afforded the title compound of Step A.

Step B

3-[7-Chloro-5-fluoro-1,3-dihydro-1-[(4-methoxyphenyl)methyl-]2,1 -benzisothiazol-4-yl]-6-(trifluoromethyl)-2,4(1H,3H)-i pyrimidinedione S,S-dioxide A solution of ethyl 3-amino-4,4,4-trifluorocrotonate (0.627 g, 3.42 mmol) in DMF (5 mL) was added to sodium hydride (137 mg, 60% suspension in oil) at –10° to –5° C. The reaction mixture was stirred initially at –10° to –5° C. for 30 min, and then cooled to –78° C. The reaction mixture was stirred for 2 h and warmed to room temperature with continued stirring for 12 h. The reaction mixture was then poured into ice cold aqueous HCl (10 mL of conc. HCl and 18 g of ice) and extracted with ethyl acetate (25 mL). The organic extract was dried (MgSO₄) and concentrated. The title compound of Step B, a compound of the invention, was isolated by flash chromatography as a solid melting at >230° C. ¹H NMR (Me₂SO-d₆, 400 MHz): δ 12.75 (br s,1H), 7.80 (d,1H), 7.27 (d,2H), 6.88 (d,2H), 6.45 (s,1H), 4.89 (s,2H), 486 (d,1H), 4.54 (d,1H), 3.72 (s,3H).

EXAMPLE 16

3-[7-Chloro-5-fluoro-1,3-dihydro-1-[(4-methoxphenyl)methyl]-2,1-benzisothiazol-4-yl]-1-methyl-6-(trifluoromethyl)-2,4(1H3H)-pyrimidinedione S,S-dioxide A mixture of the title compound of Step B in Example 15 (0.948 g, 1.82 mmol), dimethyl sulfate (0.24 g, 1.91 mmol) and K₂CO₃ (0.504 g, 3.65 mmol) in acetone (10 mL) was heated at reflux for 3 h. After the reaction was complete (TLC), the reaction mixture was cooled, insolubles were filtered off and the filtrate was concentrated on a rotary evaporator to give a solid. The title compound of Example 16, a compound of the invention, was isolated by flash chromatography as a solid melting at 180°–182° C. ¹H NMR (CDCl₃, 300 MHz): δ 7.27 (m,3H), 6.81 (m,2H), 6.31 (s,1H), 4.98 (s,2H), 3.94 (d,2H), 3.77 (s,3H), 3.54 (s,3H).

EXAMPLE 17

3-(7-Chloro-5-fluoro-1,3-dihydro-2,1-benzisothiazol-4-yl)-1-methyl-6-(trifluoromethyl)-2,4(1H,3H)-pyrimidinedione S,S-dioxide To a solution of the title compound of Example 16 (0.12 g, 0.225 mmol) in ethyl acetate (3 mL) was added conc. H₂SO₄ (3 mL) at –10° C. The reaction mixture was stirred at 0° C. for 1 h. After the reaction was complete (TLC), the reaction mixture was poured into a mixture of ice (60 g) and ethyl acetate (400 mL). The organic phase was separated, washed with water (2×50 mL), dried (MgSO₄) and concentrated. The title compound of Example 17, a compound of the invention, was isolated by flash chromatography as a solid melting at >230° C. ¹H NMR (Me₂SO-d₆, 400 MHz): δ 11.18 (bs,1H), 7.68 (d,1H), 6.62 (s,1H), 4.58 (q,2H), 3.42 (s,3H).

EXAMPLE 18

1-Acetyl-7-chloro-4-[3,6-dihydro-3-methyl-2,6-dioxo-4-(trifluoromethyl)-1(2H)-pyrimidinyl]-5-fluoro-1,3-dihydro-2,1-benzisothiazole 2,2-dioxide To a solution of the title compound of Example 17 (0.1 g, 0.253 mmol), triethylamine (38.5 mg, 0.38 mmol) and pyridine (0.1 g) in tetrahydrofuran (4 mL) was added acetyl chloride (0.022 mL, 0.304 mmol) and the reaction mixture was stirred initially at 0° C. and then at room temperature for 1 h. After the reaction was complete, the solvents were removed and the title compound of Example 18, a compound of the invention, was isolated by flash chromatography as a colorless solid melting at 213°–215° C. ¹H NMR (CDCl₃, 300 MHz): δ 7.40 (d,1H), 6.37 (s,1H), 4.33 (s,2H), 3.57 (s,3H), 2.59 (s,3H).

EXAMPLE 19

Step A

4-Fluoro-1-nitro-2-(phenylmethoxy) benzene

A mixture of 5-fluoro-2-nitrophenol (28 g, 0.178 mol), benzyl bromide (33.53 g, 0.195 mol) and K₂CO₃ (30.8 g, 0.223 mol) in anhydrous DMF (150 mL) was stirred at room temperature for 12 h. After the reaction was complete, the reaction mixture was poured into a mixture of ether (1000 mL) and water (200 mL). The organic phase was separated, washed with water (3×100 mL), dried (MgSO₄) and concentrated to give the title compound of Step A (40.5 g).

Step B

4-Fluoro-2-(phenylmethoxy)benzenamine

To a mixture of iron powder (90.36 g, 1.62 mol) and acetic acid (10%, 400 mL) at 80° C. was added a solution of the title compound of Step A (40 g, 0.162 mol) in ethyl acetate (200 mL) dropwise with vigorous stirring. The reaction mixture was stirred further at 76° C. for 1 h. After the reaction was complete, the hot reaction mixture was filtered through Celite® (200 g) and the filter cake was washed with ethyl acetate (1000 mL). The filtrate was washed with water (3×200 mL), sodium bicarbonate solution (5%, 3×200 mL), dried (MgSO₄) and concentrated to give the crude product. The product was purified by flash chromatography to give 24.76 g of the title compound of Step B. ¹H NMR (CDCl₃, 400 MHz): δ 7.41 (m,5H), 6.60 (m,3H), 5.04 (s,2H).

Step C

1-Chloro-N-(4-fluoro-2-hydroxphenyl)methanesulfonamide

To a mixture of the title compound of Step B (13 g, 59.8 mmol) in pyridine (60 mL) at 0° C. was added chloromethylsulfonyl chloride (8.92 g, 59.8 mmol) dropwise at 0° C. under a nitrogen atmosphere. The reaction mixture was then stirred at 0° C. for 1.5 h and at room temperature for 6 h. After the reaction was complete (TLC), the reaction mixture was poured into ethyl acetate (750 mL) containing dilute HCl (10%, 150 mL). The organic phase was separated, washed successively with water (2×100 mL), dilute HCl (2×100 mL) and water (2×100 mL). After drying (MgSO$_4$), the organic layer was concentrated under reduced pressure to give 10.8 g of a solid melting at 87°–90° C. A suspension of this solid (10.5 g, 31.8 mmol) and Pd-C (10%, 1.0 g) in THF (60 mL) was hydrogenated using a Parr-shaker at 40 psi for 6 h. After the reaction was complete, the catalyst was filtered and the filtrate was concentrated to give 7.6 g of the title compound of Step C as a solid melting at 141°–143° C. $^1$H NMR (CDCl$_3$, 300 MHz): δ 7.28 (dd,1H), 6.6 (dd,1H), 6.64 (m,1H), 4.52 (s,2H).

Step D

6-Fluoro-1H-4,2,1-benzoxathiazine 2,2-dioxide

A mixture of the title compound of Step C (0.985 g, 4.11 mmol) and K$_2$CO$_3$ (0.625 g, 4.52 mmol) in DMF (5 mL) was heated at 100° C. for 4 h. After the starting material had been consumed (TLC), the reaction mixture was poured into an ethyl acetate (50 mL) and water (10 mL) mixture. The organic phase was washed with water (2×10 mL), dried (MgSO$_4$), and concentrated. The product was purified by flash chromatography to give 0.42 g of the title compound of Step D as yellow solid. $^1$H NMR (CDCl$_3$, 300 MHz): δ 6.8 (m,3H), 6.2 (s,1H, NH), 4.95 (s,2H). IR (CDCl$_3$) 3347, 1506, 1148 cm$^{-1}$.

Step E

6-Fluoro-1-(phenylmethyl)-1H-4,2,1-benzoxathiazine 2,2-dioxide

A mixture of the title compound of Step D (0.5 g, 2.46 mmol), K$_2$CO$_3$ (1.02 g, 7.38 mmol), benzyl bromide (0.463 g, 2.71 mmol) and TBAB (79 mg) in DMF (5 mL) was stirred at room temperature for 48 h. After the reaction was complete, the reaction mixture was poured into an H$_2$O/ethyl acetate mixture (10/100 mL). The organic phase was separated, dried and concentrated to give the title compound of Step E as a brown solid (0.76 g). $^1$H NMR (CDCl$_3$, 300 MHz): δ 7.32 (m,6H, aromatic) 6.72 (d,1H, 11 Hz), 6.34 (d,1H, 8 Hz), 4.82 (s,2H), 4.69 (s,2H).

Step F

6-Fluoro-7-nitro-1-(phenylmethyl)-1H-4,2,1-benzoxathiazine 2,2-dioxide and 6-Fluoro-7-nitro-1-[(4-nitrophenyl)methyl]-1H-4,2,1-benzoxathiazine 2,2-dioxide To a solution of the title compound of Step E (0.76 g, 2.46 mmol) in acetic acid (20 mL) and H$_2$SO$_4$ (80%, 11.4 mL) was added nitric acid (2.9 mL, 70% HNO$_3$+0.3 mL H$_2$O) at 0° C. and resulting reaction mixture was stirred initially at 0° C. for 1 h and then at room temperature for 1.5 h. After the reaction was complete, the mixture was poured into ice water (50 mL) and extracted with ethyl acetate (100 mL). The organic extract was washed with water (2×10 mL), dried and concentrated. The two resulting products were separated by flash chromatography. The first compound eluted was 6-fluoro-7-nitro-1-(phenylmethyl)-1H-4,2,1-benzoxathiazine 2,2-dioxide (0.29 g) as a solid melting at 128°–130° C. $^1$H NMR (CDCl$_3$, 400 MHz): δ 7.80 (d,1H, J=7 Hz), 7.30–7.39 (m,5H), 6.93 (d,1H, J=10.5 Hz), 4.99 (s,2H), 4.88 (s,2H). The second compound eluted was 6-fluoro-7-nitro-1-[(4-nitrophenyl)methyl]-1H-4,2,1-benzoxathiazine 2,2-dioxide (0.296 gm) as a solid melting at 119°–122° C.

Step G

6-Fluoro-1-(phenylmethyl)-1H-4,2,1-benzoxathiazine-7-amine 2,2-dioxide

A mixture of 6-fluoro-7-nitro-1-(phenylmethyl)-1H-4,2,1-benzoxathiazine 2,2-dioxide (1.96 g, 5.79 mmol) and SnCl$_2$.2H$_2$O (6.55 g, 29 mmol) in ethyl acetate (40 mL) was heated at reflux for 3 h. After the reaction was complete, ethyl acetate (400 mL) and then Na$_2$CO$_3$ (18.5 g) were added, and the mixture was stirred for 12 h. The resulting mixture was filtered and the filtrate was concentrated under reduced pressure to give 1.20 g of the title compound of Step G.

Step H

2-[6-Fluoro-1-(phenylmethyl)-1H-4,2,1-benzoxathiazin-7-yl]-4,5,6,7-tetrahydro-1H-isoindole-1,3(2H)-dione S,S-dioxide A mixture of the title compound of Step G (1.2 g, 3.89 mmol), 3,4,5,6-tetrahydrophthalic anhydride (0.59 g) and acetic acid (6 mL) was heated at reflux for 48 h. After the reaction was complete, the reaction mixture was poured into an ethyl acetate (100 mL) and water (20 mL) mixture. The organic layer was separated, dried, and concentrated. Flash chromatography of the residue afforded 1.17 g of the title compound of Step H, a compound of the invention, as a colorless solid melting at 150°–152° C. $^1$H NMR (CDCl$_3$, 300 MHz): δ 7.33 (m,5H), 6.89 (m,2H), 4.92 (s,2H), 4.79 (s,2H), 2.41 (m,4H), 1.81 (m,4H).

By the procedures described herein, the following compounds of Tables 1–19 can be prepared. The following abbreviations are used: Ph=phenyl, c=cyclo, t=tertiary, Me=methyl. All allyl groups are the normal isomers unless indicated otherwise.

TABLE 1

Compounds of Formula I wherein $R^1$ = F, $R^2$ = Cl, $R^4$ = $R^5$ = H, J = J − 1, Z = CH$_2$, $R^9$ = $R^{10}$ = H, n = 1, m = 2,

| $R^3$ | $R^3$ | $R^3$ | $R^3$ | $R^3$ |
|---|---|---|---|---|
| H | c-propyl | CH$_3$OCH$_2$ | PhCH$_2$OC(=O) | CH$_3$OCH$_2$CH$_2$OCH$_2$ |
| CH$_3$ | c-hexyl | CH$_3$OCH$_2$CH$_2$ | (4-MeO-Ph)CH$_2$ | Cl$_3$CCH$_2$OC(=O) |
| ethyl | FCH$_2$CH$_2$CH$_2$ | CH$_3$S(O)$_2$ | PhCH$_2$ | ClCH$_2$CH$_2$CH$_2$ |
| propyl | CHF$_2$ | CH$_3$C(=O) | propargyl | (CH$_3$)$_3$COC(=O) |
| octyl | allyl | CH$_3$NHC(=O) | CH$_3$NHS(O)$_2$ | CH$_2$=CHCH$_2$CH$_2$CH$_2$ |

Compounds of Formula II wherein $R^1$ = F, $R^4$ = $R^5$ = H, J = J − 1, Z = CH$_2$, $R^9$ = $R^{10}$ = H, n = 1, m = 2, X = direct bond,

| $R^3$ | $R^3$ | $R^3$ | $R^3$ | $R^3$ |
|---|---|---|---|---|
| H | c-propyl | CH$_3$OCH$_2$ | PhCH$_2$OC(=O) | CH$_3$OCH$_2$CH$_2$OCH$_2$ |
| CH$_3$ | c-hexyl | CH$_3$OCH$_2$CH$_2$ | (4-MeO-Ph)CH$_2$ | Cl$_3$CCH$_2$OC(=O) |

TABLE 1-continued

| | | | | |
|---|---|---|---|---|
| ethyl | FCH$_2$CH$_2$CH$_2$ | CH$_3$S(O)$_2$ | PhCH$_2$ | ClCH$_2$CH$_2$CH$_2$ |
| propyl | CHF$_2$ | CH$_3$C(=O) | propargyl | (CH$_3$)$_3$COC(=O) |
| octyl | allyl | CH$_3$NHC(=O) | CH$_3$NHS(O)$_2$ | CH$_2$=CHCH$_2$CH$_2$CH$_2$ |

X = O,

| R$^3$ | R$^3$ | R$^3$ | R$^3$ | R$^3$ |
|---|---|---|---|---|
| H | c-propyl | CH$_3$OCH$_2$ | PhCH$_2$OC(=O) | CH$_3$OCH$_2$CH$_2$OCH$_2$ |
| CH$_3$ | c-hexyl | CH$_3$OCH$_2$CH$_2$ | (4-MeO-Ph)CH$_2$ | Cl$_3$CCH$_2$OC(=O) |
| ethyl | FCH$_2$CH$_2$CH$_2$ | CH$_3$S(O)$_2$ | PhCH$_2$ | ClCH$_2$CH$_2$CH$_2$ |
| propyl | CHF$_2$ | CH$_3$C(=O) | propargyl | (CH$_3$)$_3$COC(=O) |
| octyl | allyl | CH$_3$NHC(=O) | CH$_3$NHS(O)$_2$ | CH$_2$=CHCH$_2$CH$_2$CH$_2$ |

X = S,

| R$^3$ | R$^3$ | R$^3$ | R$^3$ | R$^3$ |
|---|---|---|---|---|
| H | c-propyl | CH$_3$OCH$_2$ | PhCH$_2$OC(=O) | CH$_3$OCH$_2$CH$_2$OCH$_2$ |
| CH$_3$ | c-hexyl | CH$_3$OCH$_2$CH$_2$ | (4-MeO-Ph)CH$_2$ | Cl$_3$CCH$_2$OC(=O) |
| ethyl | FCH$_2$CH$_2$CH$_2$ | CH$_3$S(O)$_2$ | PhCH$_2$ | ClCH$_2$CH$_2$CH$_2$ |
| propyl | CHF$_2$ | CH$_3$C(=O) | propargyl | (CH$_3$)$_3$COC(=O) |
| octyl | allyl | CH$_3$NHC(=O) | CH$_3$NHS(O)$_2$ | CH$_2$=CHCH$_2$CH$_2$CH$_2$ |

X = NH,

| R$^3$ | R$^3$ | R$^3$ | R$^3$ | R$^3$ |
|---|---|---|---|---|
| H | c-propyl | CH$_3$OCH$_2$ | PhCH$_2$OC(=O) | CH$_3$OCH$_2$CH$_2$OCH$_2$ |
| CH$_3$ | c-hexyl | CH$_3$OCH$_2$CH$_2$ | (4-MeO-Ph)CH$_2$ | Cl$_3$CCH$_2$OC(=O) |
| ethyl | FCH$_2$CH$_2$CH$_2$ | CH$_3$S(O)$_2$ | PhCH$_2$ | ClCH$_2$CH$_2$CH$_2$ |
| propyl | CHF$_2$ | CH$_3$C(=O) | propargyl | (CH$_3$)$_3$COC(=O) |
| octyl | allyl | CH$_3$NHC(=O) | CH$_3$NHS(O)$_2$ | CH$_2$=CHCH$_2$CH$_2$CH$_2$ |

X = NCH$_3$,

| R$^3$ | R$^3$ | R$^3$ | R$^3$ | R$^3$ |
|---|---|---|---|---|
| H | c-propyl | CH$_3$OCH$_2$ | PhCH$_2$OC(=O) | CH$_3$OCH$_2$CH$_2$OCH$_2$ |
| CH$_3$ | c-hexyl | CH$_3$OCH$_2$CH$_2$ | (4-MeO-Ph)CH$_2$ | Cl$_3$CCH$_2$OC(=O) |
| ethyl | FCH$_2$CH$_2$CH$_2$ | CH$_3$S(O)$_2$ | PhCH$_2$ | ClCH$_2$CH$_2$CH$_2$ |
| propyl | CHF$_2$ | CH$_3$C(=O) | propargyl | (CH$_3$)$_3$COC(=O) |
| octyl | allyl | CH$_3$NHC(=O) | CH$_3$NHS(O)$_2$ | CH$_2$=CHCH$_2$CH$_2$CH$_2$ |

TABLE 2

Compounds of Formula I wherein R$^1$ = F, R$^2$ = Cl, R$^4$ = R$^5$ = H, J = J - 2, R$^9$ = R$^{10}$ = H, Z = CH$_2$, m = 1, n = 2,

| R$^3$ | R$^3$ | R$^3$ | R$^3$ | R$^3$ |
|---|---|---|---|---|
| H | c-propyl | CH$_3$OCH$_2$ | PhCH$_2$OC(=O) | CH$_3$OCH$_2$CH$_2$OCH$_2$ |
| CH$_3$ | c-hexyl | CH$_3$OCH$_2$CH$_2$ | (4-MeO-Ph)CH$_2$ | Cl$_3$CCH$_2$OC(=O) |
| ethyl | FCH$_2$CH$_2$CH$_2$ | CH$_3$S(O)$_2$ | PhCH$_2$ | ClCH$_2$CH$_2$CH$_2$ |
| propyl | CHF$_2$ | CH$_3$C(=O) | propargyl | (CH$_3$)$_3$COC(=O) |
| octyl | allyl | CH$_3$NHC(=O) | CH$_3$NHS(O)$_2$ | CH$_2$=CHCH$_2$CH$_2$CH$_2$ |

Z = CHF, n = 1, m = 1,

| R$^3$ | R$^3$ | R$^3$ | R$^3$ | R$^3$ |
|---|---|---|---|---|
| H | c-propyl | CH$_3$OCH$_2$ | PhCH$_2$OC(=O) | CH$_3$OCH$_2$CH$_2$OCH$_2$ |
| CH$_3$ | c-hexyl | CH$_3$OCH$_2$CH$_2$ | (4-MeO-Ph)CH$_2$ | Cl$_3$CCH$_2$OC(=O) |
| ethyl | FCH$_2$CH$_2$CH$_2$ | CH$_3$S(O)$_2$ | PhCH$_2$ | ClCH$_2$CH$_2$CH$_2$ |
| propyl | CHF$_2$ | CH$_3$C(=O) | propargyl | (CH$_3$)$_3$COC(=O) |
| octyl | allyl | CH$_3$NHC(=O) | CH$_3$NHS(O)$_2$ | CH$_2$=CHCH$_2$CH$_2$CH$_2$ |

Z = O, n = 2, m = 1,

| R$^3$ | R$^3$ | R$^3$ | R$^3$ | R$^3$ |
|---|---|---|---|---|
| H | c-propyl | CH$_3$OCH$_2$ | PhCH$_2$OC(=O) | CH$_3$OCH$_2$CH$_2$OCH$_2$ |
| CH$_3$ | c-hexyl | CH$_3$OCH$_2$CH$_2$ | (4-MeO-Ph)CH$_2$ | Cl$_3$CCH$_2$OC(=O) |
| ethyl | FCH$_2$CH$_2$CH$_2$ | CH$_3$S(O)$_2$ | PhCH$_2$ | ClCH$_2$CH$_2$CH$_2$ |
| propyl | CHF$_2$ | CH$_3$C(=O) | propargyl | (CH$_3$)$_3$COC(=O) |
| octyl | allyl | CH$_3$NHC(=O) | CH$_3$NHS(O)$_2$ | CH$_2$=CHCH$_2$CH$_2$CH$_2$ |

TABLE 2-continued

Compounds of Formula II wherein $R^1$ = F, $R^4$ = $R^5$ = H, J = J – 2, Z = $CH_2$, $R^9$ = $R^{10}$ = H, n = 1, m = 2, Z = $CH_2$, X = direct bond.

| $R^3$ | $R^3$ | $R^3$ | $R^3$ | $R^3$ |
|---|---|---|---|---|
| H | c-propyl | $CH_3OCH_2$ | $PhCH_2OC(=O)$ | $CH_3OCH_2CH_2OCH_2$ |
| $CH_3$ | c-hexyl | $CH_3OCH_2CH_2$ | (4-MeO-Ph)$CH_2$ | $Cl_3CCH_2OC(=O)$ |
| ethyl | $FCH_2CH_2CH_2$ | $CH_3S(O)_2$ | $PhCH_2$ | $ClCH_2CH_2CH_2$ |
| propyl | $CHF_2$ | $CH_3C(=O)$ | propargyl | $(CH_3)_3COC(=O)$ |
| octyl | allyl | $CH_3NHC(=O)$ | $CH_3NHS(O)_2$ | $CH_2=CHCH_2CH_2CH_2$ |

X = O,

| $R^3$ | $R^3$ | $R^3$ | $R^3$ | $R^3$ |
|---|---|---|---|---|
| H | c-propyl | $CH_3OCH_2$ | $PhCH_2OC(=O)$ | $CH_3OCH_2CH_2OCH_2$ |
| $CH_3$ | c-hexyl | $CH_3OCH_2CH_2$ | (4-MeO-Ph)$CH_2$ | $Cl_3CCH_2OC(=O)$ |
| ethyl | $FCH_2CH_2CH_2$ | $CH_3S(O)_2$ | $PhCH_2$ | $ClCH_2CH_2CH_2$ |
| propyl | $CHF_2$ | $CH_3C(=O)$ | propargyl | $(CH_3)_3COC(=O)$ |
| octyl | allyl | $CH_3NHC(=O)$ | $CH_3NHS(O)_2$ | $CH_2=CHCH_2CH_2CH_2$ |

X = S,

| $R^3$ | $R^3$ | $R^3$ | $R^3$ | $R^3$ |
|---|---|---|---|---|
| H | c-propyl | $CH_3OCH_2$ | $PhCH_2OC(=O)$ | $CH_3OCH_2CH_2OCH_2$ |
| $CH_3$ | c-hexyl | $CH_3OCH_2CH_2$ | (4-MeO-Ph)$CH_2$ | $Cl_3CCH_2OC(=O)$ |
| ethyl | $FCH_2CH_2CH_2$ | $CH_3S(O)_2$ | $PhCH_2$ | $ClCH_2CH_2CH_2$ |
| propyl | $CHF_2$ | $CH_3C(=O)$ | propargyl | $(CH_3)_3COC(=O)$ |
| octyl | allyl | $CH_3NHC(=O)$ | $CH_3NHS(O)_2$ | $CH_2=CHCH_2CH_2CH_2$ |

X = NH,

| $R^3$ | $R^3$ | $R^3$ | $R^3$ | $R^3$ |
|---|---|---|---|---|
| H | c-propyl | $CH_3OCH_2$ | $PhCH_2OC(=O)$ | $CH_3OCH_2CH_2OCH_2$ |
| $CH_3$ | c-hexyl | $CH_3OCH_2CH_2$ | (4-MeO-Ph)$CH_2$ | $Cl_3CCH_2OC(=O)$ |
| ethyl | $FCH_2CH_2CH_2$ | $CH_3S(O)_2$ | $PhCH_2$ | $ClCH_2CH_2CH_2$ |
| propyl | $CHF_2$ | $CH_3C(=O)$ | propargyl | $(CH_3)_3COC(=O)$ |
| octyl | allyl | $CH_3NHC(=O)$ | $CH_3NHS(O)_2$ | $CH_2=CHCH_2CH_2CH_2$ |

X = $NCH_3$,

| $R^3$ | $R^3$ | $R^3$ | $R^3$ | $R^3$ |
|---|---|---|---|---|
| H | c-propyl | $CH_3OCH_2$ | $PhCH_2OC(=O)$ | $CH_3OCH_2CH_2OCH_2$ |
| $CH_3$ | c-hexyl | $CH_3OCH_2CH_2$ | (4-MeO-Ph)$CH_2$ | $Cl_3CCH_2OC(=O)$ |
| ethyl | $FCH_2CH_2CH_2$ | $CH_3S(O)_2$ | $PhCH_2$ | $ClCH_2CH_2CH_2$ |
| propyl | $CHF_2$ | $CH_3C(=O)$ | propargyl | $(CH_3)_3COC(=O)$ |
| octyl | allyl | $CH_3NHC(=O)$ | $CH_3NHS(O)_2$ | $CH_2=CHCH_2CH_2CH_2$ |

TABLE 3

Compounds of Formula I wherein J = J – 3, $R^1$ = F, $R^2$ = Cl, $R^4$ = $R^5$ = H, $R^{11}$ = $CF_2H$, $R^{12}$ = $CH_3$.

| $R^3$ | $R^3$ | $R^3$ | $R^3$ | $R^3$ |
|---|---|---|---|---|
| H | c-propyl | $CH_3OCH_2$ | $PhCH_2OC(=O)$ | $CH_3OCH_2CH_2OCH_2$ |
| $CH_3$ | c-hexyl | $CH_3OCH_2CH_2$ | (4-MeO-Ph)$CH_2$ | $Cl_3CCH_2OC(=O)$ |
| ethyl | $FCH_2CH_2CH_2$ | $CH_3S(O)_2$ | $PhCH_2$ | $ClCH_2CH_2CH_2$ |
| propyl | $CHF_2$ | $CH_3C(=O)$ | propargyl | $(CH_3)_3COC(=O)$ |
| octyl | allyl | $CH_3NHC(=O)$ | $CH_3NHS(O)_2$ | $CH_2=CHCH_2CH_2CH_2$ |

Compounds of Formula II wherein J = J – 3, $R^1$ = F, $R^4$ = $R^5$ = H, $R^{11}$ = $CF_2H$, $R^{12}$ = $CH_3$, X = Direct Bond.

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

TABLE 3-continued

X=O,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

TABLE 4

Compounds of Formula I wherein $J = J - 4$, $R^1 = F$, $R^2 = Cl$, $R^4 = R^5 = H$, $Q = O$, $R^{13} = CH_3$, $W = CH$, $R^{14} = CF_3$,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

$W = N$, $R^{14} = N(CH_3)_2$,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

Compounds of Formula II wherein $J = J - 4$, $R^1 = F$, $R^4 = R^5 = H$, $Q = O$, $R^{13} = CH_3$, $X$ = Direct Bond, $W = CH$, $R^{14} = CF_3$,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

$X = O$, $W = N$, $R^{14} = (CH_3)_2$,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

TABLE 5

Compounds of Formula I wherein $J = J - 5$, $R^1 = F$, $R^2 = Cl$, $R^4 = R^5 = H$, $Q = O$, $R^9 = R^{10} = H$, $Z = CH_2$, only single bonds in left-hand ring, $n = m = 1$,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

$m = 2$, $n = 1$,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

Compounds of Formula II wherein $J = J - 5$, $R^1 = F$, $R^4 = R^5 = H$, $Q = O$, $R^9 = R^{10} = H$, $Z = CH_2$, only single bonds in left-hand ring.

TABLE 5-continued

X = Direct Bond, n = m = 1,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

X = O, m = 2, n = 1,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

TABLE 6

Compounds of Formula I wherein J = J-6, $R^1$ = F, $R^2$ = Cl, $R^4$ = $R^5$ = H, Q = O, $R^{16}$ = $R^{17}$ = H, only single bonds in left-hand ring,

| $R^3$ | $R^3$ | $R^3$ | $R^3$ | $R^3$ |
|---|---|---|---|---|

$Z^1$ = $CH_2$, n = m = 1,

| H | c-hexyl | $CH_3OCH_2$ | $PhCH_2OC(=O)$ | $CH_3NHC(=O)$ |
|---|---|---|---|---|
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

$Z^1$ = CHF, n = m = 1,

| H | c-hexyl | $CH_3OCH_2$ | $PhCH_2OC(=O)$ | $CH_3NHC(=O)$ |
|---|---|---|---|---|
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

$Z^1$ = $CF_2$, $Z^1$ = $CF_2$, n = m = 1,

| H | c-hexyl | $CH_3OCH_2$ | $PhCH_2OC(=O)$ | $CH_3NHC(=O)$ |
|---|---|---|---|---|
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

$Z^1$ = O, n = 2, m = 1

| H | c-hexyl | $CH_3OCH_2$ | $PhCH_2OC(=O)$ | $CH_3NHC(=O)$ |
|---|---|---|---|---|
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

Compounds of Formula II wherein J = J − 6, $R^1$ = F, $R^4$ = $R^5$ = H, Q = O, $R^{16}$ = $R^{17}$ = H, n = m = 1, only single bonds in left-hand ring,

| $R^3$ | $R^3$ | $R^3$ | $R^3$ | $R^3$ |
|---|---|---|---|---|

X = Direct Bond, $Z^1$ = $CH_2$,

| H | c-hexyl | $CH_3OCH_2$ | $PhCH_2OC(=O)$ | $CH_3NHC(=O)$ |
|---|---|---|---|---|
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

X = $NCH_3$, $Z^1$ = $CH_2$,

| H | c-hexyl | $CH_3OCH_2$ | $PhCH_2OC(=O)$ | $CH_3NHC(=O)$ |
|---|---|---|---|---|
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

X = Direct Bond, $Z^1$ = CHF,

| H | c-hexyl | $CH_3OCH_2$ | $PhCH_2OC(=O)$ | $CH_3NHC(=O)$ |
|---|---|---|---|---|
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

TABLE 6-continued $X = NCH_3, Z^1 = CHF,$

| | | | | |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2$ |

TABLE 7

Compounds of Formula I wherein J = J – 7, $R^1$ = F, $R^2$ = Cl, $R^4$ = $R^5$ = H, Q = O, $R^{12}$ = H,

| $R^3$ | $R^{11}$ | $R^3$ | $R^{11}$ | $R^3$ | $R^{11}$ |
|---|---|---|---|---|---|
| H | H | $FCH_2CH_2CH_2$ | $CH_3$ | $CHF_2$ | $CH_3$ |
| $CH_3$ | H | $CH_3OCH_2CH_2$ | $CH_3$ | allyl | H |
| ethyl | $CH_3$ | $CH_3S(O)_2$ | $FCH_2CH_2CH_2$ | propargyl | $FCH_2CH_2CH_2$ |
| ethyl | $FCH_2CH_2CH_2$ | $CH_3C(=O)$ | $FCH_2CH_2CH_2$ | $PhCH_2$ | $CH_3$ |

Compounds of Formula II wherein J = J – 7, $R^1$ = F, $R^4$ = $R^5$ = H, Q = O, $R^{12}$ = H,

| $R^3$ | $R^{11}$ | $R^3$ | $R^{11}$ | $R^3$ | $R^{11}$ |
|---|---|---|---|---|---|

X = Direct Bond,

| | | | | | |
|---|---|---|---|---|---|
| H | H | $FCH_2CH_2CH_2$ | $CH_3$ | $CHF_2$ | $CH_3$ |
| $CH_3$ | H | $CH_3OCH_2CH_2$ | $CH_3$ | allyl | H |
| ethyl | $CH_3$ | $CH_3S(O)_2$ | $FCH_2CH_2CH_2$ | propargyl | $FCH_2CH_2CH_2$ |
| ethyl | $FCH_2CH_2CH_2$ | $CH_3C(=O)$ | $FCH_2CH_2CH_2$ | $PhCH_2$ | $CH_3$ |

$X = NCH_3,$

| | | | | | |
|---|---|---|---|---|---|
| H | H | $FCH_2CH_2CH_2$ | $CH_3$ | $CHF_2$ | $CH_3$ |
| $CH_3$ | H | $CH_3OCH_2CH_2$ | $CH_3$ | allyl | H |
| ethyl | $CH_3$ | $CH_3S(O)_2$ | $FCH_2CH_2CH^2$ | propargyl | $FCH_2CH_2CH_2$ |
| ethyl | $FCH_2CH_2CH_2$ | $CH_3C(=O)$ | $FCH_2CH_2CH_2$ | $PhCH_2$ | $CH_3$ |

TABLE 8

Compounds of Formula I wherein J = J – 8, $R^1$ = F, $R^2$ = Cl, $R^4$ = $R^5$ = H, $R^{18}$ = t-butyl,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2$ |

Compounds of Formula II wherein J = J – 8, $R^1$ = F, $R^4$ = $R^5$ = H, $R^{18}$ = t-butyl, X = O,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2$ |

TABLE 9

Compounds of Formula I wherein J = J – 9, $R^1$ = F, $R^2$ = Cl, $R^4$ = $R^5$ = H, Q = O, $R^{18}$ = $CH_2CH_2CH_2F$,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2$ |

TABLE 9-continued

Compounds of Formula II wherein J = J – 9, $R^1$ = F, $R^4$ = $R^5$ = H, Q = O, $R^{18}$ = $CH_2CH_2CH_2F$, X = O,

| $R^3$ | $R^3$ | $R^3$ | $R^3$ | $R^3$ |
|---|---|---|---|---|
| H | c-hexyl | $CH_3OCH_2$ | $PhCH_2OC(=O)$ | $CH_3NHC(=O)$ |
| $CH_3$ | $FCH_2CH_2CH_2$ | $CH_3OCH_2CH_2$ | $PhCH_2$ | $ClCH_2CH_2CH_2$ |
| ethyl | $CHF_2$ | $CH_3S(O)_2$ | propargyl | $(CH_3)_3COC(=O)$ |
| octyl | allyl | $CH_3C(=O)$ | $CH_3NHS(O)_2$ | $CH_2=CHCH_2CH_2CH_2$ |

TABLE 10

Compounds of Formula I wherein J = J – 10, $R^1$ = F, $R^2$ = Cl, $R^4$ = $R^5$ = H, Q = O, $R^9$ = $R^{10}$ = H, Z = $CH_2$, m = n = 1, $R^{19}$ = $R^{20}$ = H,

| $R^3$ | $R^3$ | $R^3$ | $R^3$ | $R^3$ |
|---|---|---|---|---|
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

Compounds of Formula II wherein J = J – 10, $R^1$ = F, $R^4$ = $R^5$ = H, Q = O, $R^9$ = $R^{10}$ = H, Z = $CH_2$, m = n = 1, $R^{19}$ = $R^{20}$ = H, X = O,

| $R^3$ | $R^3$ | $R^3$ | $R^3$ | $R^3$ |
|---|---|---|---|---|
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

TABLE 11

Compounds of Formula I wherein J = J – 12, $R^1$ = F, $R^2$ = Cl, $R^4$ = $R^5$ = H, Q = O, $Q^1$ = S, $R^9$ = $R^{10}$ = H, Z = $CH_2$, m = n = 1, only single bonds in left-hand ring,

| $R^3$ | $R^3$ | $R^3$ | $R^3$ | $R^3$ |
|---|---|---|---|---|
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

Compounds of Formula II wherein J = J – 12, $R^1$ = F, $R^4$ = $R^5$ = H, Q = O, $Q^1$ = S, $R^9$ = $R^{10}$ = H, X = O, m = n = 1, only single bonds in left-hand ring,

| $R^3$ | $R^3$ | $R^3$ | $R^3$ | $R^3$ |
|---|---|---|---|---|
| Z = $CH_2$, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |
| Z = CHF, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

TABLE 12

Compounds of Formula I wherein J = J – 14, $R^1$ = F, $R^2$ = Cl, $R^4$ = $R^5$ = H, $Q^1$ = S, $R^9$ = $R^{10}$ = H, Z = $CH_2$, m = 2, n = 1,

| $R^3$ | $R^3$ | $R^3$ | $R^3$ | $R^3$ |
|---|---|---|---|---|
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

TABLE 12-continued

Compounds of Formula II wherein J = J – 14, $R^1$ = F, $R^4$ = $R^5$ = H, $Q^1$ = S, $R^9$ = $R^{10}$ = H, Z = $CH_2$, m = 2, n = 1, X = O,

| $R^3$ | $R^3$ | $R^3$ | $R^3$ | $R^3$ |
|---|---|---|---|---|
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

TABLE 13

Compounds of Formula I wherein J = J – 15, $R^1$ = F, $R^2$ = Cl, $R^4$ = $R^5$ = H, $R^9$ = $R^{10}$ = H, Z = $CH_2$, m = 2, n = 1, $R^{23}$ = Cl,

| $R^3$ | $R^3$ | $R^3$ | $R^3$ | $R^3$ |
|---|---|---|---|---|
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

Compounds of Formula II wherein J = J – 15, $R^1$ = F, $R^4$ = $R^5$ = H, $R^9$ = $R^{10}$ = H, Z = $CH_2$, m = 2, n = 1, $R^{23}$ = Cl,

| $R^3$ | $R^3$ | $R^3$ | $R^3$ | $R^3$ |
|---|---|---|---|---|
| X = Direct Bond, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |
| X = O, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

TABLE 14

Compounds of Formula I wherein J = J – 16, $R^1$ = F, $R^2$ = Cl, $R^4$ = $R^5$ = H, $R^{23}$ = Cl, $R^{24}$ = $CF_3$, $R^{25}$ = $CH_3$,

| $R^3$ | $R^3$ | $R^3$ | $R^3$ | $R^3$ |
|---|---|---|---|---|
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

Compounds of Formula II wherein J = J – 16, $R^1$ = F, $R^4$ = $R^5$ = H, $R^{23}$ = Cl, $R^{24}$ = $CF_3$, $R^{25}$ = $CH_3$,

| $R^3$ | $R^3$ | $R^3$ | $R^3$ | $R^3$ |
|---|---|---|---|---|
| X = Direct Bond, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |
| X = O, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

TABLE 15

Compounds of Formula I wherein J = J − 17, $R^1$ = F, $R^2$ = Cl, $R^4$ = $R^5$ = H, $R^9$ = $R^{10}$ = H, m = n = 1, $R^{26}$ = $CH_3$,

| $R^3$ | $R^3$ | $R^3$ | $R^3$ | $R^3$ |
|---|---|---|---|---|
| Z = $CH_2$, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |
| Z = CHF, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

Compounds of Formula II wherein J = J − 17, $R^1$ = F, $R^4$ = $R^5$ = H, $R^9$ = $R^{10}$ = H, m = n = 1, $R^{26}$ = $CH_3$,

| $R^3$ | $R^3$ | $R^3$ | $R^3$ | $R^3$ |
|---|---|---|---|---|
| X = Direct Bond, Z = $CH_2$, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |
| X = O, Z = $CH_2$, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |
| X = O, Z = CHF, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

TABLE 16

Compounds of Formula I wherein J = J − 18, $R^1$ = F, $R^2$ = Cl, $R^4$ = $R^5$ = H, $R^9$ = $R^{10}$ = H, m = 2, n = 1, $R^{26}$ = $CH_3$,

| $R^3$ | $R^3$ | $R^3$ | $R^3$ | $R^3$ |
|---|---|---|---|---|
| Z = $CH_2$, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |
| Z = CHF, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

Compounds of Formula II wherein J = J − 18, $R^1$ = F, $R^4$ = $R^5$ = H, $R^9$ = $R^{10}$ = H, m = n = 1, $R^{26}$ = $CH_3$,

| $R^3$ | $R^3$ | $R^3$ | $R^3$ | $R^3$ |
|---|---|---|---|---|
| X = O, Z = $CH_2$, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |
| X = O, Z = CHF, | | | | |
| H | $FCH_2CH_2CH_2$ | $CH_3OCH_2CH_2$ | $PhCH_2OC(=O)$ | $CH_3NHC(=O)$ |
| $CH_3$ | $CHF_2$ | $CH_3S(O)_2$ | $PhCH_2$ | octyl |
| ethyl | allyl | $CH_3C(=O)$ | propargyl | $(CH_3)_3COC(=O)$ |

TABLE 17

Compounds of Formula I where in J = J - 1, $R^3$ = ethyl, $R^4 = R^5$ = H, $R^9 = R^{10}$ = H, m = 2, n = 1, Z = $CH_2$,

| $R^1$ | $R^2$ | $R^1$ | $R^2$ | $R^1$ | $R^2$ | $R^1$ | $R^2$ | $R^1$ | $R^2$ |
|---|---|---|---|---|---|---|---|---|---|
| H | Cl | Cl | F | Cl | Cl | F | Br | F | $NO_2$ |
| H | F | Br | Cl | Br | F | F | $CF_3$ | F | CN |

Compounds of Formula II wherein J = J - 1, $R^3$ = ethyl, $R^4 = R^5$ = H, $R^9 = R^{10}$ = H, m = 2, n = 1, Z = $CH_2$,

| $R^1$ | X | $R^1$ | X | $R^1$ | X | $R^1$ | X | $R^1$ | X |
|---|---|---|---|---|---|---|---|---|---|
| H | O | Cl | O | Cl | S | F | O | F | direct bond |
| H | S | Br | O | Br | S | F | S | F | $NCH_3$ |

TABLE 18

Compounds of Formula I wherein J = J - 1, $R^1$ = F, $R^2$ = Cl, $R^3$ = ethyl, $R^9 = R^{10}$ = H, m = 2, n = 1, Z = $CH_2$,

| $R^4$ | $R^5$ | $R^4$ | $R^5$ | $R^4$ | $R^5$ | $R^4$ | $R^5$ | $R^4$ | $R^5$ |
|---|---|---|---|---|---|---|---|---|---|
| Cl | H | Br | H | $CH_3$ | $CH_3$ | ethyl | H | H | C(=O)$CH_3$ |
| F | H | $CH_3$ | H | H | $CF_3$ | H | $S(O)_2CH_3$ | spiro-cyclopropyl | |

Compounds of Formula II wherein J = J - 1, $R^1$ = F, $R^3$ = ethyl, $R^9 = R^{10}$ = H, m = 2, n = 1, Z = $CH_2$, X = O,

| $R^4$ | $R^5$ | $R^4$ | $R^5$ | $R^4$ | $R^5$ | $R^4$ | $R^5$ | $R^4$ | $R^5$ |
|---|---|---|---|---|---|---|---|---|---|
| Cl | H | Br | H | $CH_3$ | $CH_3$ | ethyl | H | H | C(=O)$CH_3$ |
| F | H | $CH_3$ | H | H | $CF_3$ | H | $S(O)_2CH_3$ | spiro-cyclopropyl | |

TABLE 19

$R^3$ = ethyl, $R^1$ = F, $R^4 = R^5$ = H,

J = [cyclopropyl-fused ring structure with N, N—, and two C=O groups]

| Formula | $R^2$ | Formula | X |
|---|---|---|---|
| I | Cl | II | Direct bond |
| I | F | II | $NCH_3$ |
| I | $NO_2$ | II | NH |
| I | $CF_3$ | II | $NCH_2CH_3$ |

Formulation/Utility

Compounds of this invention will generally be used in formulation with an agriculturally suitable carrier comprising at least one of a liquid diluent, a solid diluent or a surfactant wherein the formulation is consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, New Jersey. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillinite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and U.S. Pat. No. DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Tables A–F.

| Example A | |
|---|---|
| High Strength Concentrate | |
| Compound 8 | 98.5% |
| silica aerogel | 0.5% |
| synthetic amorphous fine silica | 1.0% |

| Example B | |
|---|---|
| Wettable Powder | |
| Compound 18 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

| Example C | |
|---|---|
| Granule | |
| Compound 8 | 10.0% |
| attapulgite granules (low volatile matter, 0.71/0.30 mm; U.S.S. No. 25-50 sieves) | 90.0% |

| Example D | |
|---|---|
| Extruded Pellet | |
| Compound 18 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Tests results indicate that the compounds of the present invention are highly active preemergent and/or postemergent herbicides and/or plant growth regulants. Many of them have utility for broad-spectrum pre- and/or postemergence weed control in areas where complete control of all vegetation is desired such as around fuel storage tanks, industrial storage areas, parking lots, drive-in theaters, around billboards and highway and railroad structures. Some of the compounds are useful for the control of selected grass and broadleaf weeds with tolerance to important agronomic crops which include but are not limited to barley, cotton, wheat, rape, sugarbeets, corn, soybeans, rice, and plantation crops including coffee, cocoa, oil palm, rubber, sugarcane, citrus, grapes, fruit trees, nut trees, banana, plantain, pineapple, conifers, e.g., loblolly pine, and turf species, e.g., Kentucky bluegrass, St. Augustine grass, Kentucky fescue and bermudagrass. Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. A mixture of one or more of the following herbicides with a compound of this invention may be particularly useful for weed control: acetochlor, acifluorfen and its sodium salt, acrolein (2-propenal), alachlor, ametryn, amidosulfuron, amitrole, ammonium sulfamate, anilofos, asulam, atrazine, azimsulfuron, benazolin, benazolin-ethyl, benfluralin, benfuresate, bensulfuron-methyl, bensulide, bentazone, bifenox, bromacil, bromoxynil, bromoxynil octanoate, butachlor, butralin, butylate, chlomethoxyfen, chloramben, chlorbromuron, chloridazon, chlorimuron-ethyl, chlornitrofen, chlorotoluron, chlorpropham, chlorsulfuron, chlorthal-dimethyl, cinmethylin, cinosulfuron, clethodim, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its dimethylammonium, potassium and sodium salts, dichlobenil, dichlorprop, diclofop-methyl, difenzoquat metilsulfate, diflufenican, dimepiperate, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethyl α,2-dichloro-5-[4-(difluoromethyl)-4,5-dihydro-3-methyl-5-oxo-1H-1,2,4-triazol-1-yl]-4-fluorobenzenepropanoate (F8426), fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, fluridone, flurochloridone, fluroxypyr, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methyl [[2-chloro-4-fluoro-5-[(tetrahydro-3-oxo-1H,3H-[1,3,4]thiadiazolo[3,4-α]pyridazin-1-ylidene)amino]phenyl]thioacetate (KIH 9201), methylarsonic acid and its calcium, monoammonium, monosodium and disodium salts, methyl [[[1-[5-[2-chloro-4-(trifluoromethyl)phenoxy]-2-nitrophenyl]-2-methoxethylidene]amino]oxy]acetate (AKH-7088), methyl 5-[[[[(4,6-dimethyl-2-pyrimidiny) amino]carbonyl]amino]sulfonyl]-1-(2-pyridinyl)-1H-pyrazole-4-carboxylate (NC-330), metobenzuron, metolachlor, metoxuron, metribuzin, metsulfuron-methyl, molinate, monolinuron, napropamide, naptalam, neburon, nicosulfuron, norflurazon, oryzalin, oxadiazon, oxyfluorfen, paraquat dichloride, pebulate, pendimethalin, perfluidone, phenmedipham, picloram, picloram-potassium, pretilachlor, primisulfuron-methyl, prometon, prometryn, propachlor, propanil, propazine, propham, propyza mnide, prosulfuron, pyrazolynate, pyrazosulfuron-ethyl, quinclorac, quizalofop-ethyl, quizalofop-P-ethyl, quizalofop-P-tefuryl, rimsulf uron, sethoxydim, siduron, simazine, sulcotrione (ICIA0051), sulfentrazone, sulfometuron-methyl, TCA, TCA-sodium, tebuthiuron, terbacil, terbuthylazine, terbutryn, thenylchlor, thifensulfuron-methyl, thiobencarb, tralkoxydim, tri-allate, triasulfuron, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds.

Preferred are mixtures of a compound of Formula I with a compound selected from the group diuron, fluazifop-butyl, fluazifop-P-butyl, glufosinate, glufosinate-ammonium, glyphosate, glyphosate-isopropylammonium, glyphosate-sesquisodium, glyphosate-trimesium, hexazinone, metribuzin, norflurazon, paraquat, quizalofop-ethyl, and quizalofop-P-ethyl. Specifically preferred are mixtures of a compound selected from the group 3-(7-chloro-1-ethyl-5-fluoro-1,3-dihydro-2,1-benzisothiazol-4-yl)-1-methyl-6-(trifluoromethyl)-2,4(1H,3H)-pyrimidinedione S,S-dioxide and 3-[(7-chloro-1-ethyl-5-fluoro- 1,3-dihydro-2,1-benzisothiazol-4-yl)imino]tetrahydro- 1H,3H-[1,3,4]thiadiazolo[3,4-α]pyridazin-1-one S,S-dioxide with a compound selected from the group diuron, fluazifop-butyl, fluazifop-P-butyl, glufosinate, glufosinate-ammonium, glyphosate, glyphosate-isopropyla rnmonium, glyphosate-sesquisodium, glyphosate-trimesium, hexazinone, metribuzin, norflurazon, paraquat, quizalofop-ethyl, and quizalofop-P-ethyl.

A herbicidally effective amount of the compounds of this invention is determined by a number of factors. These factors include: formulation selected, method of application, amount and type of vegetation present, growing conditions, etc. In general, a herbicidally effective amount of a compound(s) of this invention is applied at rates from about 0.001 to 20 kg/ha with a preferred rate range of 0.004 to 1.0 kg/ha. One skilled in the art can easily determine application rates necessary for the desired level of weed control.

The following Tests demonstrate the control efficacy of the compounds of this invention against specific weeds. The weed control afforded by the compounds is not limited, however, to these species. See Index Tables A–F for compound descriptions.

INDEX TABLE A

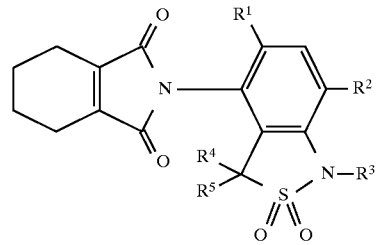

| Cmpd No. | $R^1$ | $R^2$ | $R^3$ | $R^4$ | $R^5$ | m.p. (°C.) |
|---|---|---|---|---|---|---|
| 1 (Ex. 1) | F | H | $CH_2CH_3$ | H | H | 189–190 |
| 2 (Ex. 2) | F | Cl | $CH_2CH_3$ | H | H | 190–192 |
| 3 (Ex. 13) | F | Cl | $CH_2$-(4-$CH_3$O—Ph) | H | H | 171–174 |
| 4 (Ex. 13) | F | Cl | H | H | H | 75–79 |
| 5 (Ex. 14) | F | Cl | C(=O)$CH_3$ | H | H | 205–208 |
| 6[a] | F | Cl | $CH_2$C≡CH | H | H | solid* |

*See Index Table F for $^1$H NMR data.
[a]Compound contains 50% by weight of 2-[1,3-bis(2-propynyl)-7-chloro-5-fluoro-1,3-dihydro-2,1-benzisothiazol-4-yl]-4,5,6,7-tetrahydro-1H-isoindole-1,3(2H)-dione S,S-dioxide.

INDEX TABLE B

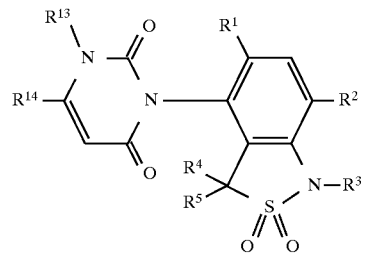

| Cmpd No. | $R^1$ | $R^2$ | $R^3$ | $R^4$ | $R^5$ | $R^{13}$ | $R^{14}$ | m.p. (°C.) |
|---|---|---|---|---|---|---|---|---|
| 7 (Ex. 4) | F | Cl | $CH_2CH_3$ | H | H | H | $CF_3$ | >230 |
| 8 (Ex. 5) | F | Cl | $CH_2CH_3$ | H | H | $CH_3$ | $CF_3$ | 147–149 |
| 9 (Ex. 6) | F | Cl | $CH_2CH_3$ | H | H | $CH_2CH_3$ | $CF_3$ | 177–178 |
| 10 (Ex. 15) | F | Cl | $CH_2$-(4-$CH_3$O—Ph) | H | H | H | $CF_3$ | >230 |
| 11 (Ex. 16) | F | Cl | $CH_2$-(4-$CH_3$O—Ph) | H | H | $CH_3$ | $CF_3$ | 180–182 |
| 12 (Ex. 17) | F | Cl | H | H | H | $CH_3$ | $CF_3$ | >230 |
| 13 (Ex. 18) | F | Cl | C(=O)$CH_3$ | H | H | $CH_3$ | $CF_3$ | 213–215 |

INDEX TABLE C

| Cmpd No. | R¹ | R² | R³ | R⁴ | R⁵ | Z¹ | m.p. (°C.) |
|---|---|---|---|---|---|---|---|
| 14 (Ex. 8) | F | Cl | $CH_2CH_3$ | H | H | $CH_2$ | 168–169 |
| 15 (Ex. 9) | F | Cl | $CH_2CH_3$ | H | H | O | 200–202 |

INDEX TABLE D

| Cmpd No. | R¹ | R² | R³ | R⁴ | R⁵ | J | m.p. (°C.) |
|---|---|---|---|---|---|---|---|
| 16 (Ex. 10) | F | Cl | $CH_2CH_3$ | H | H | (unsaturated bicyclic triazinedione) | oil* |
| 17 (Ex. 11) | F | Cl | $CH_2CH_3$ | H | H | (saturated bicyclic triazinedione) | 87–90 |
| 18 (Ex. 7) | F | Cl | $CH_2CH_3$ | H | H | (bicyclic thione) | 143–146 |
| 19 (Ex. 12) | F | Cl | $CH_2CH_3$ | H | H | (F₂HC/H₃C-substituted triazolinone) | semisolid* |

*See Index Table F for ¹H NMR data.

INDEX TABLE E

[Structure: cyclohexene-fused imide N-linked to phenyl ring bearing R¹, substituted with X-CR⁴R⁵-N(R³)-SO₂ group]

| Cmpd No. | R¹ | R³ | R⁴ | R⁵ | X | m.p. (°C.) |
|---|---|---|---|---|---|---|
| 20 (Ex. 19) | F | CH₂Ph | H | H | O | 150–152 |
| 21 (Ex. 3) | F | CH₂CH₃ | H | H | direct bond | oil* |

*See Index Table F for ¹H NMR data.

INDEX TABLE F

| Cmpd No. | ¹H NMR data (in CDCl₃ solution unless otherwise indicated)ᵃ |
|---|---|
| 6 | δ 7.26 (d,1H), 4.58 (s,2H), 4.48 (m,2H), 2.42 (br s,4H), 2.21 (t,1H), 1.82 (br s,2H). |
| 16 | δ 7.30 (d,1H,J = 9.6 Hz), 5.99 (s,2H), 4.31 (s,2H), 4.21 (s,4H), 3.93 (dd,2H), 1.28 (t,3H). |
| 19 | δ 7.26 (d,1H), 7.04 t,1H), 4.28 (s,2H), 3.96 (q,2H), 2.44 (s,3H), 1.26 (t,3H). |
| 21 | δ 7.08 (d,1H), 6.62 (d,2H), 4.32 (s,2H), 3.64 (q,2H), 2.42 (m,4H), 1.82 (m,4H), 1.38 (t,3H). |

INDEX TABLE F-continued

| Cmpd No. | ¹H NMR data (in CDCl₃ solution unless otherwise indicated)ᵃ |
|---|---|

ᵃ¹H NMR data are in ppm downfield from tetramethylsilane. Couplings are designated by (s)-singlet, (d)-doublet, (t)-triplet, (q)-quartlet, (m)-multiplet, (dd)-doublet of doublets, (br s)-broad singlet.

Seeds of barley (Hordeum vulgare), barnyardgrass (Echinochloa crus-galli), bedstraw (Galium aparine), blackgrass (Alopecurus myosuroides), chickweed (Stellaria media), cocklebur (Xanthium pensylvanicum), corn (Zea mays), cotton (Gossypium hirsutum), crabgrass (Digitaria sanguinalis), downy brome (Bromus tectorum), giant foxtail (Setaria faberii), lambsquarters (Chenopodium album), morningglory (Ipomoea hederacea), rape (Brassica napus), rice (Oryza sativa), sorghum (Sorghum bicolor), soybean (Glycine max), sugar beet (Beta vulgaris), velvetleaf (Abutilon theophrasti), wheat (Triticum aestivum), wild buckwheat (Polygonum convolvulus), wild oat (Avena fatua) and purple nutsedge (Cyperus rotundus) tubers were planted and treated preemergence with test chemicals formulated in a non-phytotoxic solvent mixture which includes a surfactant.

At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

| TABLE A | COMPOUND | TABLE A | COMPOUND |
|---|---|---|---|
| Rate 2000 g/ha POSTEMERGENCE | 7 | Rate 2000 g/ha PREEMERGENCE | 7 |
| Barley | 0 | Barley | 0 |
| Barnyardgrass | 0 | Barnyardgrass | 0 |
| Bedstraw | 2 | Bedstraw | 0 |
| Blackgrass | 1 | Blackgrass | 0 |
| Chickweed | 0 | Chickweed | 0 |
| Cocklebur | 2 | Cocklebur | 0 |
| Corn | 1 | Corn | 0 |
| Cotton | 2 | Cotton | 0 |
| Crabgrass | 1 | Crabgrass | 0 |
| Downy brome | 0 | Downy brome | 0 |
| Giant foxtail | 1 | Giant foxtail | 0 |
| Lambsquarter | 1 | Lambsquarter | 0 |
| Morningglory | 2 | Morningglory | 3 |
| Nutsedge | 0 | Nutsedge | 0 |
| Rape | 2 | Rape | 0 |
| Rice | 0 | Rice | 0 |
| Sorghum | 0 | Sorghum | 0 |
| Soybean | 2 | Soybean | 2 |
| Sugar beet | 1 | Sugar beet | 0 |
| Velvetleaf | 1 | Velvetleaf | 0 |
| Wheat | 0 | Wheat | 0 |
| Wild buckwheat | 2 | Wild buckwheat | 0 |
| Wild oat | 0 | | |

| TABLE A | COMPOUND | | | TABLE A | COMPOUND | | | |
|---|---|---|---|---|---|---|---|---|
| Rate 1000 g/ha POSTEMERGENCE | 1 | 2 | 16 | 20 Rate 1000 g/ha PREEMERGENCE | 1 | 2 | 16 | 20 |
| Barley | 3 | 4 | 3 | 3 Barley | 0 | 0 | 0 | 0 |
| Barnyardgrass | 3 | 9 | 6 | 6 Barnyardgrass | 6 | 9 | 8 | 0 |
| Bedstraw | 7 | 10 | 6 | 6 Bedstraw | 8 | 10 | 10 | — |
| Blackgrass | 4 | 5 | 3 | 2 Blackgrass | 3 | 3 | 2 | 2 |
| Chickweed | 3 | 8 | 5 | 2 Chickweed | 3 | 9 | 2 | — |
| Cocklebur | 6 | 9 | 8 | 8 Cocklebur | 0 | 4 | 8 | 3 |
| Corn | 3 | 5 | 2 | 2 Corn | 2 | 3 | 3 | 2 |

-continued

| | | | | | | | | | |
|---|---|---|---|---|---|---|---|---|---|
| Cotton | 9 | 10 | 10 | 9 | Cotton | 0 | 10 | 10 | 0 |
| Crabgrass | 3 | 6 | 5 | 7 | Crabgrass | 4 | 9 | 8 | 3 |
| Downy brome | 3 | 2 | 2 | 2 | Downy brome | 2 | 3 | 0 | — |
| Giant foxtail | 3 | 6 | 7 | 4 | Giant foxtail | 2 | 8 | 9 | 4 |
| Lambsquarter | 8 | 9 | 9 | 8 | Lambsquarter | 9 | 10 | 10 | — |
| Morningglory | 9 | 9 | 9 | 8 | Morningglory | 1 | 10 | 8 | 4 |
| Nutsedge | 0 | 2 | 2 | 2 | Nutsedge | 0 | 5 | — | — |
| Rape | 7 | 10 | 10 | 7 | Rape | 6 | 10 | 10 | — |
| Rice | 5 | 6 | 7 | 5 | Rice | 0 | 4 | 3 | 0 |
| Sorghum | 3 | 8 | 6 | 2 | Sorghum | 0 | 2 | 7 | 0 |
| Soybean | 5 | 8 | 9 | 5 | Soybean | 0 | 7 | 8 | 0 |
| Sugar beet | 9 | 10 | 10 | 4 | Sugar beet | 8 | 10 | 10 | — |
| Velvetleaf | 8 | 10 | 10 | 6 | Velvetleaf | 8 | 10 | 10 | 2 |
| Wheat | 4 | 4 | 3 | 2 | Wheat | 0 | 2 | 3 | 0 |
| Wild buckwheat | 10 | 10 | 9 | 6 | Wild buckwheat | 0 | 10 | 9 | — |
| Wild oat | 3 | 4 | 2 | 2 | Wild oat | 2 | 4 | 2 | 0 |

| TABLE A | COMPOUND | | TABLE A | COMPOUND | |
|---|---|---|---|---|---|
| Rate 400 g/ha POSTEMERGENCE | 7 | 12 | Rate 400 g/ha PREEMERGENCE | 7 | 12 |
| Barley | 0 | 10 | Barley | 0 | 0 |
| Barnyardgrass | 1 | 10 | Barnyardgrass | 0 | 3 |
| Bedstraw | 1 | 10 | Bedstraw | 0 | 10 |
| Blackgrass | 0 | 6 | Blackgrass | 0 | 2 |
| Chickweed | 0 | 10 | Chickweed | 0 | 2 |
| Cocklebur | 1 | 10 | Cocklebur | 0 | 10 |
| Corn | 0 | 10 | Corn | 0 | 0 |
| Cotton | — | 10 | Cotton | 0 | 10 |
| Crabgrass | 0 | 8 | Crabgrass | 0 | 4 |
| Downy brome | 0 | 8 | Downy brome | 0 | 3 |
| Giant foxtail | 0 | 9 | Giant foxtail | 0 | 5 |
| Lambsquarter | 0 | 10 | Lambsquarter | 0 | 9 |
| Morningglory | — | 10 | Morningglory | 1 | 10 |
| Nutsedge | 0 | 5 | Nutsedge | 0 | 7 |
| Rape | 0 | 10 | Rape | 0 | 9 |
| Rice | 0 | 10 | Rice | 0 | 5 |
| Sorghum | 0 | 10 | Sorghum | 0 | 0 |
| Soybean | 1 | 10 | Soybean | 0 | 9 |
| Sugar beet | 1 | 10 | Sugar beet | 0 | 10 |
| Velvetleaf | 1 | 10 | Velvetleaf | 0 | 10 |
| Wheat | 0 | 10 | Wheat | 0 | 0 |
| Wild buckwheat | 1 | 10 | Wild buckwheat | 0 | 6 |
| Wild oat | 0 | 10 | Wild oat | 0 | 0 |

| TABLE A | COMPOUND | | | | | | | | | | | | | | | | |
|---|---|---|---|---|---|---|---|---|---|---|---|---|---|---|---|---|---|
| Rate 200 g/ha POSTEMERGENCE | 1 | 2 | 3 | 4 | 5 | 6 | 8 | 9 | 10 | 11 | 13 | 14 | 15 | 16 | 17 | 18 | 20 | 21 |
| Barley | 3 | 3 | 5 | 2 | 3 | 5 | 8 | 6 | 0 | 4 | 6 | 2 | 1 | 3 | 5 | 9 | 3 | 2 |
| Barnyardgrass | 2 | 7 | 4 | 10 | 10 | 7 | 10 | 10 | 0 | 6 | 10 | 3 | 7 | 2 | 9 | 9 | 6 | 5 |
| Bedstraw | 5 | 10 | 4 | 8 | 9 | 9 | 10 | 10 | 0 | 10 | 10 | 5 | 6 | 5 | 10 | 10 | 5 | 6 |
| Blackgrass | 3 | 3 | 2 | 2 | 6 | 3 | 7 | 9 | 0 | 3 | 2 | 3 | 2 | 2 | 3 | 6 | 1 | 1 |
| Chickweed | 3 | 4 | 2 | 6 | 9 | 4 | 10 | 3 | 0 | 7 | 10 | 3 | 6 | 3 | 3 | 8 | 1 | 3 |
| Cocklebur | 6 | 9 | 10 | 10 | 10 | 10 | 10 | 3 | 0 | 10 | 10 | 7 | 6 | 7 | 8 | 10 | 7 | 7 |
| Corn | 2 | 3 | 3 | 6 | 2 | 3 | 9 | 9 | 0 | 2 | 9 | 1 | 4 | 1 | 3 | 5 | 2 | 2 |
| Cotton | 9 | 10 | — | 10 | 10 | 10 | 10 | 9 | 0 | 10 | 10 | 10 | 10 | 9 | 10 | 10 | 10 | 9 |
| Crabgrass | 2 | 4 | 5 | 6 | 4 | 4 | 9 | 2 | 0 | 2 | 6 | 2 | 2 | 2 | 5 | 9 | 4 | 5 |
| Downy brome | 2 | 3 | 2 | 2 | 2 | 1 | 7 | 5 | 0 | 2 | 2 | 1 | 0 | 1 | 3 | 5 | 2 | 1 |
| Giant foxtail | 2 | 4 | 6 | 5 | 5 | 4 | 9 | 6 | 0 | 2 | 6 | 2 | 3 | 2 | 6 | 9 | 3 | 3 |
| Lambsquarter | 8 | 9 | 10 | 10 | 9 | 10 | 10 | 9 | 0 | 10 | 10 | 8 | 8 | 8 | 9 | 10 | 9 | 8 |
| Morningglory | 8 | 9 | 10 | 10 | 10 | 10 | 10 | 8 | 0 | 8 | 10 | 10 | 9 | 9 | 10 | 10 | 9 | 9 |
| Nutsedge | 0 | 2 | 1 | 4 | 2 | 2 | 5 | — | 0 | 0 | 3 | 2 | — | 1 | 8 | — | 1 | 3 |
| Rape | 3 | 10 | 10 | 10 | 10 | 10 | 10 | 9 | 0 | 10 | 10 | 5 | 8 | 7 | 10 | 10 | 6 | 6 |
| Rice | 3 | 6 | 4 | 5 | 6 | 4 | 10 | 3 | 0 | 3 | 10 | 4 | 4 | 3 | 5 | 7 | 3 | 5 |
| Sorghum | 3 | 3 | 4 | 4 | 6 | 4 | 10 | 9 | 0 | 5 | 9 | 2 | 3 | 3 | 6 | 8 | 2 | 4 |
| Soybean | 3 | 8 | 5 | 5 | 5 | 5 | 10 | 9 | 0 | 8 | 10 | 8 | 9 | 8 | 9 | 10 | 3 | 7 |
| Sugar beet | 8 | 10 | 10 | 10 | 10 | 10 | 10 | 10 | 0 | 10 | 10 | 9 | 10 | 9 | 10 | 10 | 5 | 10 |
| Velvetleaf | 6 | 10 | 10 | 10 | 10 | 10 | 10 | 10 | 0 | 10 | 10 | 10 | 10 | 10 | 10 | 10 | 7 | 9 |
| Wheat | 3 | 4 | 3 | 3 | 4 | 3 | 10 | 9 | 0 | 3 | 6 | 4 | 3 | 2 | 2 | 9 | 2 | 1 |
| Wild buckwheat | 8 | 10 | 10 | 10 | 10 | 10 | 10 | 10 | 0 | 10 | 10 | 7 | 10 | 8 | 10 | 10 | 3 | 8 |
| Wild oat | 2 | 3 | 2 | 2 | 3 | 2 | 9 | 9 | 0 | 3 | 3 | 4 | 4 | 1 | 2 | 7 | 2 | 1 |

| TABLE A | COMPOUND | | | | | | | | | | | | | | | | |
|---|---|---|---|---|---|---|---|---|---|---|---|---|---|---|---|---|---|
| Rate 200 g/ha PREEMERGENCE | 1 | 2 | 3 | 4 | 5 | 6 | 8 | 9 | 10 | 11 | 13 | 14 | 15 | 16 | 17 | 18 | 20 | 21 |
| Barley | 0 | 0 | 0 | 0 | 0 | 0 | 6 | 2 | 0 | 0 | 0 | 0 | 0 | 2 | 0 | 3 | 0 | 0 |
| Barnyardgrass | 0 | 9 | 0 | 0 | 2 | 4 | 10 | 9 | 0 | 2 | 0 | 3 | 2 | 3 | 7 | 9 | 0 | 5 |
| Bedstraw | 2 | 10 | 8 | 0 | 3 | 2 | 10 | 10 | 0 | 10 | 10 | 7 | 3 | 2 | 10 | 6 | 0 | 9 |

-continued

| | | | | | | | | | | | | | | | | | | |
|---|---|---|---|---|---|---|---|---|---|---|---|---|---|---|---|---|---|---|
| Blackgrass | 2 | 3 | 1 | 0 | 0 | 0 | 9 | 0 | 0 | 0 | 0 | 3 | 1 | 1 | 0 | 5 | 0 | 2 |
| Chickweed | 0 | 7 | 0 | 0 | 0 | 0 | 10 | 8 | 0 | 0 | 0 | 3 | 4 | 0 | 0 | 3 | 0 | 0 |
| Cocklebur | 0 | 3 | 7 | 4 | 2 | 7 | 10 | 1 | 0 | 3 | 10 | 3 | 3 | 6 | 4 | 6 | 2 | 0 |
| Corn | 0 | 0 | 0 | 0 | 0 | 2 | 7 | 1 | 0 | 0 | 0 | 2 | 3 | 0 | 3 | 2 | 0 | 0 |
| Cotton | 0 | 0 | 0 | 0 | 0 | 0 | 10 | 7 | 0 | 0 | 9 | 6 | 6 | 7 | 10 | 3 | 0 | 3 |
| Crabgrass | 0 | 8 | 3 | 0 | 0 | 2 | 10 | 10 | 0 | 9 | 6 | 8 | 2 | 2 | 7 | 6 | 2 | 2 |
| Downy brome | 3 | 2 | 1 | 0 | 0 | 0 | 10 | 0 | 0 | 2 | 0 | 0 | 0 | 0 | 2 | 4 | 0 | 1 |
| Giant foxtail | 0 | 6 | 0 | 0 | 0 | 3 | 10 | 10 | 0 | 9 | 0 | 6 | 6 | 4 | 9 | 9 | 0 | 0 |
| Lambsquarter | 5 | 10 | 10 | 10 | 10 | 10 | 10 | 10 | 0 | 10 | 9 | 10 | 10 | 10 | 10 | 10 | — | 10 |
| Morningglory | 0 | 10 | 0 | 0 | 6 | 9 | 10 | 1 | 0 | 10 | 10 | 3 | 4 | 8 | 10 | 7 | 0 | 0 |
| Nutsedge | 0 | 0 | — | 0 | 0 | — | 6 | 0 | — | 0 | 0 | — | — | 0 | 1 | 0 | 0 | 0 |
| Rape | 3 | 9 | 0 | 0 | 7 | 0 | 10 | 9 | 0 | 2 | 8 | 4 | 7 | 9 | 10 | 7 | 0 | 8 |
| Rice | 0 | 0 | 0 | 0 | 0 | 0 | 9 | 0 | 0 | 0 | 3 | 1 | 3 | 1 | 4 | 2 | 0 | 0 |
| Sorghum | 0 | 0 | 0 | 0 | 0 | 0 | 10 | 8 | 0 | 0 | 0 | 2 | 1 | 0 | 7 | 2 | 0 | 0 |
| Soybean | 0 | 5 | 2 | 0 | 0 | 0 | 10 | 2 | 0 | 0 | 10 | 1 | 3 | 7 | 7 | 7 | 0 | 0 |
| Sugar beet | 0 | 10 | 8 | 2 | 7 | 8 | 10 | 10 | 0 | 10 | 10 | 10 | 10 | 10 | 7 | 10 | 2 | 10 |
| Velvetleaf | 2 | 10 | 7 | 3 | 8 | 6 | 10 | 10 | 0 | 10 | 10 | 8 | 10 | 10 | 10 | 10 | 0 | 0 |
| Wheat | 0 | 2 | 0 | 0 | 0 | 0 | 9 | 5 | 0 | 1 | 2 | 3 | 0 | 0 | 0 | 6 | 0 | 0 |
| Wild buckwheat | 0 | 9 | 0 | 0 | 2 | 0 | 10 | 9 | 0 | 0 | 3 | 0 | 3 | 0 | 10 | 5 | — | 2 |
| Wild oat | 2 | 2 | 0 | 0 | 0 | 0 | 8 | 1 | 0 | 1 | 3 | 3 | 0 | 2 | 3 | 6 | 0 | 0 |

| TABLE A | COMPOUND | TABLE A | COMPOUND |
|---|---|---|---|
| Rate 100 g/ha POSTEMERGENCE | 12 | Rate 100 g/ha PREEMERGENCE | 12 |
| Barley | 8 | Barley | 0 |
| Barnyardgrass | 10 | Barnyardgrass | 0 |
| Bedstraw | 10 | Bedstraw | 6 |
| Blackgrass | 3 | Blackgrass | 0 |
| Chickweed | 10 | Chickweed | 0 |
| Cocklebur | 10 | Cocklebur | 6 |
| Corn | 8 | Corn | 0 |
| Cotton | 10 | Cotton | 0 |
| Crabgrass | 7 | Crabgrass | 0 |
| Downy brome | 5 | Downy brome | 0 |
| Giant foxtail | 6 | Giant foxtail | 0 |
| Lambsquarter | 10 | Lambsquarter | 6 |
| Morningglory | 10 | Morningglory | 10 |
| Nutsedge | 3 | Nutsedge | 3 |
| Rape | 10 | Rape | 6 |
| Rice | 10 | Rice | 2 |
| Sorghum | 10 | Sorghum | 0 |
| Soybean | 8 | Soybean | 8 |
| Sugar beet | 10 | Sugar beet | 8 |
| Velvetleaf | 10 | Velvetleaf | 3 |
| Wheat | 10 | Wheat | 0 |
| Wild buckwheat | 10 | Wild buckwheat | 0 |
| Wild oat | 9 | Wild oat | 0 |

| TABLE A | COMPOUND | | | | | | | | | | | | | | |
|---|---|---|---|---|---|---|---|---|---|---|---|---|---|---|---|
| Rate 50 g/ha POSTEMERGENCE | 3 | 4 | 5 | 6 | 8 | 9 | 10 | 11 | 13 | 14 | 15 | 17 | 18 | 19 | 21 |
| Barley | 3 | 2 | 3 | 4 | 3 | 4 | 0 | 3 | 7 | 0 | 0 | 3 | 5 | 3 | 2 |
| Barnyardgrass | 3 | 6 | 10 | 6 | 10 | 9 | 0 | 2 | 10 | 1 | 2 | 6 | 9 | 4 | 3 |
| Bedstraw | 4 | 7 | 9 | 9 | 10 | 9 | 0 | 10 | 10 | 3 | 6 | 9 | 8 | 6 | 3 |
| Blackgrass | 2 | 1 | 3 | 2 | 7 | 8 | 0 | 3 | 2 | 2 | 1 | 0 | 6 | 3 | 1 |
| Chickweed | 2 | 4 | 6 | 2 | 10 | 3 | 0 | 7 | 10 | 2 | 1 | 2 | 8 | 8 | 2 |
| Cocklebur | 10 | 9 | 10 | 10 | 10 | 2 | 0 | 10 | 10 | 7 | 3 | 7 | 10 | 7 | 5 |
| Corn | 3 | 3 | 2 | 3 | 9 | 5 | 0 | 2 | 9 | 1 | 2 | 3 | 2 | 3 | 2 |
| Cotton | 10 | 10 | 10 | 10 | 10 | 9 | 0 | 10 | 10 | 10 | 10 | 10 | 10 | 10 | 9 |
| Crabgrass | 3 | 3 | 4 | 4 | 6 | 3 | 0 | 2 | 6 | 2 | 2 | 3 | 4 | 3 | 4 |
| Downy brome | 1 | 1 | 2 | 1 | 6 | 4 | 0 | 1 | 3 | 1 | 1 | 2 | 5 | 3 | 1 |
| Giant foxtail | 4 | 3 | 6 | 3 | 6 | 5 | 0 | 2 | 6 | 2 | 2 | 6 | 8 | 3 | 3 |
| Lambsquarter | 9 | 8 | 9 | 9 | 10 | 8 | 0 | 10 | 10 | 8 | 9 | 9 | 9 | 10 | 6 |
| Morningglory | 9 | 10 | 10 | 10 | 10 | 5 | 0 | 10 | 10 | 9 | 7 | 10 | 10 | 9 | 4 |
| Nutsedge | 1 | 1 | — | 2 | 3 | — | 0 | 0 | 3 | — | 1 | 7 | 2 | 1 | 1 |
| Rape | 9 | 10 | 10 | 10 | 10 | 9 | 0 | 10 | 10 | 3 | 5 | 9 | 9 | 3 | 3 |
| Rice | 3 | 3 | 4 | 3 | 9 | 2 | 0 | 3 | 10 | 3 | 3 | 5 | 4 | 3 | 4 |
| Sorghum | 3 | 3 | 6 | 4 | 6 | 4 | 0 | 2 | 10 | 2 | 2 | 4 | 7 | 5 | 4 |
| Soybean | 2 | 3 | 4 | 2 | 10 | 9 | 0 | 8 | 9 | 8 | 7 | 9 | 7 | 3 | 5 |
| Sugar beet | 10 | 10 | 10 | 10 | 10 | 6 | 0 | 10 | 10 | 7 | 9 | 10 | 10 | 10 | 9 |
| Velvetleaf | 10 | 10 | 10 | 10 | 10 | 9 | 0 | 10 | 10 | 10 | 6 | 10 | 10 | 9 | 6 |
| Wheat | 3 | 3 | 4 | 2 | 10 | 7 | 0 | 2 | 9 | 1 | 2 | 2 | 7 | 3 | 1 |
| Wild buckwheat | 10 | 10 | 10 | 10 | 10 | 9 | 0 | 10 | 10 | 7 | 9 | 9 | 10 | 10 | 6 |
| Wild oat | 1 | 2 | 3 | 2 | 5 | 9 | 0 | 2 | 6 | 3 | 3 | 1 | 6 | 2 | 1 |

-continued

| TABLE A | COMPOUND | | | | | | | | | | | | | | |
|---|---|---|---|---|---|---|---|---|---|---|---|---|---|---|---|
| Rate 50 g/ha PREEMERGENCE | 3 | 4 | 5 | 6 | 8 | 9 | 10 | 11 | 13 | 14 | 15 | 17 | 18 | 19 | 21 |
| Barley | 0 | 0 | 0 | 0 | 3 | 0 | 0 | 0 | 0 | 0 | 0 | 0 | 3 | 0 | 0 |
| Barnyardgrass | 0 | 0 | 0 | 0 | 10 | 1 | 0 | 0 | 0 | 0 | 0 | 4 | 6 | 3 | 1 |
| Bedstraw | 0 | 0 | 2 | 0 | 10 | 9 | 0 | 10 | 10 | 0 | 0 | 10 | 3 | 0 | 0 |
| Blackgrass | 0 | 0 | 0 | 0 | 3 | 0 | 0 | 0 | 0 | 2 | 0 | 0 | 0 | 0 | 0 |
| Chickweed | 0 | 0 | 0 | 0 | 10 | 1 | 0 | 0 | 0 | 0 | 0 | 0 | 0 | 0 | 0 |
| Cocklebur | 3 | 0 | 0 | 0 | 9 | 0 | 0 | 2 | 0 | 2 | 0 | 4 | 2 | 0 | 0 |
| Corn | 0 | 0 | 0 | 0 | 5 | 0 | 0 | 0 | 0 | 0 | 0 | 2 | 0 | 3 | 0 |
| Cotton | 0 | 0 | 0 | 0 | 10 | 2 | 0 | 0 | 1 | 0 | 3 | 9 | 0 | 10 | 0 |
| Crabgrass | 0 | 0 | 0 | 0 | 8 | 9 | 0 | 3 | 0 | 0 | 0 | 2 | 0 | 0 | 0 |
| Downy brome | 0 | 0 | 0 | 0 | 7 | 0 | 0 | 0 | 0 | 2 | 0 | 0 | 3 | 1 | 2 |
| Giant foxtail | 0 | 0 | 0 | 0 | 10 | 8 | 0 | 4 | 0 | 0 | 0 | 7 | 2 | 3 | 0 |
| Lambsquarter | 3 | 5 | 9 | 8 | 10 | 9 | 0 | 10 | 7 | 10 | 9 | 8 | 9 | 7 | 9 |
| Morningglory | 0 | 0 | 3 | 0 | 10 | 0 | 0 | 10 | 10 | 0 | 0 | 3 | 2 | 0 | 0 |
| Nutsedge | — | — | 0 | 0 | 1 | 0 | — | — | 0 | — | — | 0 | 0 | 0 | 0 |
| Rape | 0 | 0 | 0 | 0 | 10 | 4 | 0 | — | 2 | 0 | 0 | 10 | 1 | 0 | 0 |
| Rice | 0 | 0 | 0 | 0 | 5 | 0 | 0 | 0 | 0 | 0 | 0 | 1 | 0 | 0 | 0 |
| Sorghum | 0 | 0 | 0 | 0 | 4 | 0 | 0 | 0 | 0 | 0 | 0 | 3 | 0 | 0 | 0 |
| Soybean | 0 | 0 | 0 | 0 | 9 | 0 | 0 | 0 | 0 | 0 | 0 | 7 | 0 | 3 | 0 |
| Sugar beet | 0 | 2 | 3 | 7 | 10 | 5 | 0 | 8 | 7 | 7 | 9 | 9 | 9 | 9 | 9 |
| Velvetleaf | 0 | 0 | 2 | 3 | 10 | 1 | 0 | 10 | 2 | 6 | 2 | 10 | 6 | 5 | 0 |
| Wheat | 0 | 0 | 0 | 0 | 5 | 2 | 0 | 1 | 0 | 0 | 0 | 0 | 2 | 1 | 0 |
| Wild buckwheat | 0 | 0 | 0 | 0 | 10 | 4 | 0 | 0 | 0 | 0 | 0 | 8 | 0 | 0 | 0 |
| Wild oat | 0 | 0 | 0 | 0 | 3 | 2 | 0 | 0 | 0 | 0 | 0 | 0 | 3 | 1 | 0 |

| TABLE A | COMPOUND | TABLE A | COMPOUND |
|---|---|---|---|
| Rate 10 g/ha POSTEMERGENCE | 19 | Rate 10 g/ha PREEMERGENCE | 19 |
| Barley | 2 | Barley | 0 |
| Barnyardgrass | 3 | Barnyardgrass | 3 |
| Bedstraw | 3 | Bedstraw | 0 |
| Blackgrass | 1 | Blackgrass | 0 |
| Chickweed | 3 | Chickweed | 0 |
| Cocklebur | 4 | Cocklebur | 0 |
| Corn | 2 | Corn | 0 |
| Cotton | — | Cotton | 5 |
| Crabgrass | 3 | Crabgrass | 0 |
| Downy brome | 1 | Downy brome | 0 |
| Giant foxtail | 2 | Giant foxtail | 0 |
| Lambsquarter | 6 | Lambsquarter | 4 |
| Morningglory | 6 | Morningglory | 0 |
| Nutsedge | 1 | Nutsedge | 0 |
| Rape | 1 | Rape | 0 |
| Rice | 2 | Rice | 2 |
| Sorghum | 3 | Sorghum | 0 |
| Soybean | 3 | Soybean | 3 |
| Sugar beet | 10 | Sugar beet | 1 |
| Velvetleaf | 8 | Velvetleaf | 3 |
| Wheat | 3 | Wheat | 0 |
| Wild buckwheat | 10 | Wild buckwheat | 0 |
| Wild oat | 1 | Wild oat | 0 |

Test B

The compounds evaluated in this test were formulated in a non-phytotoxic solvent mixture which includes a surfactant and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgare*), bedstraw (*Galium aparine*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), giant foxtail (*Setaria faberii*), johnsongrass (*Sorghum halpense*), lambsquarters (*Chenopodium album*), morningglory (*Ipomoea hederacea*), pigweed (*Amaranthus retroflexus*), rape (*Brassica napus*), ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avenafatua*). All plant species were planted one day before application of the compound for the preemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*), barnyardgrass (*Echinochloa crus-galli*) and late watergrass (*Echinochloa oryzicola*) grown to the 2 leaf stage for testing.

All plant species were grown using normal greenhouse practices. Visual evaluations of injury expressed on treated plants, when compared to untreated controls, were recorded approximately fourteen to twenty one days after application of the test compound. Plant response this ratings, summarized in Table B, were recorded on a 0 to 100 scale where 0 is no effect and 100 is complete control. A dash (-) response means no test result.

TABLE B

| | COMPOUND | | COMPOUND | | |
|---|---|---|---|---|---|
| Rate 500 g/ha | 2 | Rate 250 g/ha | 2 | 9 | 14 |
| POST-EMERGENCE | | POST-EMERGENCE | | | |
| Barley Igri | — | Barley Igri | 35 | 65 | 30 |
| Barnyardgr. (Flood) | 70 | Barnyardgr. (Flood) | 35 | 95 | 25 |
| Barnyardgrass | — | Barnyardgrass | 45 | 100 | 40 |
| Bedstraw | — | Bedstraw | 85 | 100 | 35 |
| Blackgrass | — | Blackgrass | 10 | 90 | 40 |
| Chickweed | — | Chickweed | 30 | 70 | 70 |
| Cocklebur | — | Cocklebur | 90 | 75 | 80 |
| Corn | — | Corn | 25 | 90 | 40 |
| Cotton | — | Cotton | 100 | 100 | 100 |
| Crabgrass | — | Crabgrass | 25 | 70 | 55 |
| Downy Brome | — | Downy Brome | 0 | 35 | 40 |
| Duck salad | 25 | Duck salad | 20 | 0 | 95 |
| Giant foxtail | — | Giant foxtail | 40 | 90 | 50 |
| Italn. Rygrass | — | Italn. Rygrass | 0 | 30 | 35 |
| Johnsongrass | — | Johnsongrass | 50 | 90 | 75 |
| Lambsquarter | — | Lambsquarter | 100 | 100 | 95 |
| Morningglory | — | Morningglory | 100 | 90 | 100 |
| Rape | — | Rape | 100 | 100 | 90 |
| Redroot Pigweed | — | Redroot Pigweed | — | 100 | 90 |
| Rice Japonica | 60 | Rice Japonica | 45 | 75 | 70 |
| Soybean | — | Soybean | — | 60 | 60 |
| Speedwell | — | Speedwell | 100 | — | 100 |
| Sugar beet | — | Sugar beet | 100 | 100 | 100 |
| Umbrella sedge | 65 | Umbrella sedge | 45 | 60 | 100 |
| Velvetleaf | — | Velvetleaf | 100 | 100 | 100 |
| Watergrass | 75 | Watergrass | 35 | 80 | 30 |
| Wheat | — | Wheat | 30 | 60 | 30 |
| Wild buckwheat | — | Wild buckwheat | 65 | 100 | 100 |
| Wild oat | — | Wild oat | 35 | 90 | 40 |

| | COMPOUND | | | | COMPOUND | | | |
|---|---|---|---|---|---|---|---|---|
| Rate 250 g/ha | 2 | 9 | 14 | Rate 125 g/ha | 2 | 9 | 14 | 17 |
| PREEMERGENCE | | | | POST-EMERGENCE | | | | |
| Barley Igri | 10 | 10 | 0 | Barley Igri | 35 | 35 | 30 | 25 |
| Barnyardgrass | 40 | 100 | 90 | Barnyardgr. (Flood) | 10 | 65 | 0 | 75 |
| Bedstraw | 20 | 100 | 85 | Barnyardgrass | 35 | 100 | 35 | 75 |
| Blackgrass | 0 | 65 | 45 | Bedstraw | 60 | 100 | 35 | 100 |
| Chickweed | 10 | 30 | 10 | Blackgrass | 10 | 80 | 35 | 30 |
| Cocklebur | 0 | 10 | 85 | Chickweed | 30 | 50 | 70 | 60 |
| Corn | 10 | 40 | 25 | Cocklebur | 90 | 50 | 80 | 95 |
| Cotton | 40 | 80 | 95 | Corn | 15 | 90 | 30 | 30 |
| Crabgrass | 75 | 95 | 85 | Cotton | 100 | 100 | 100 | 100 |
| Downy Brome | 0 | 0 | 0 | Crabgrass | 20 | 60 | 45 | 30 |
| Giant foxtail | 85 | 100 | 90 | Downy Brome | 0 | 25 | 20 | 20 |
| Italn. Rygrass | 0 | 90 | 75 | Duck salad | 0 | 0 | 80 | 95 |
| Johnsongrass | 90 | 100 | 45 | Giant foxtail | 40 | 85 | 30 | 50 |
| Lambsquarter | 95 | 100 | 100 | Italn. Rygrass | 0 | 20 | 20 | 30 |
| Morningglory | 100 | 60 | 25 | Johnsongrass | 40 | 90 | 40 | 75 |
| Rape | 30 | 95 | 85 | Lambsquarter | 85 | 100 | 65 | 100 |
| Redroot Pigweed | 100 | 100 | 90 | Morningglory | 100 | 80 | 90 | 100 |
| Soybean | 10 | 50 | 30 | Rape | 100 | 100 | 90 | 100 |
| Speedwell | — | 100 | 100 | Redroot Pigweed | 100 | 100 | 90 | 90 |
| Sugar beet | 95 | 100 | 100 | Rice Japonica | 30 | 45 | 45 | 75 |
| Velvetleaf | 100 | 100 | 100 | Soybean | 100 | 40 | 50 | 85 |
| Wheat | 0 | 35 | 10 | Speedwell | 100 | — | 100 | 100 |
| Wild buckwheat | 0 | 100 | 85 | Sugar beet | 100 | 100 | 100 | 100 |
| Wild oat | 35 | 95 | 30 | Umbrella sedge | 15 | 0 | 95 | 85 |
| | | | | Velvetleaf | 100 | 100 | 100 | 100 |
| | | | | Watergrass | 10 | 35 | 25 | 70 |
| | | | | Wheat | 25 | 45 | 20 | 30 |
| | | | | Wild buckwheat | 65 | 100 | 80 | 100 |
| | | | | Wild oat | 35 | 90 | 35 | 35 |

| | COMPOUND | | | |
|---|---|---|---|---|
| Rate 125 g/ha | 2 | 9 | 14 | 17 |

TABLE B-continued

| PREEMERGENCE | | | | |
|---|---|---|---|---|
| Barley Igri | 0 | 10 | 020 | |
| Barnyardgrass | 20 | 85 | 10 | 70 |
| Bedstraw | 0 | 100 | 0 | 100 |
| Blackgrass | 0 | 50 | 45 | 0 |
| Chickweed | 10 | 10 | 0 | 0 |
| Cocklebur | 0 | 0 | 35 | 70 |
| Corn | 0 | 25 | 0 | 20 |
| Cotton | 0 | 70 | 50 | 100 |
| Crabgrass | 20 | 75 | 20 | 65 |
| Downy Brome | 0 | 0 | 0 | 10 |
| Giant foxtail | 50 | 100 | 20 | 55 |
| Italn. Rygrass | 0 | 20 | 0 | 0 |
| Johnsongrass | 30 | 50 | 30 | 50 |
| Lambsquarter | 95 | 100 | 95 | 100 |
| Morningglory | 0 | 50 | 20 | 80 |
| Rape | 0 | 75 | 10 | 100 |
| Redroot Pigweed | 100 | 100 | 10 | 100 |
| Soybean | 0 | 30 | 10 | 50 |
| Speedwell | — | 100 | 0 | 100 |
| sugar beet | 30 | 100 | 0 | 100 |
| Velvetleaf | 100 | 100 | 10 | 100 |
| Wheat | 0 | 20 | 0 | 0 |
| Wild buckwheat | 0 | 90 | 35 | 100 |
| Wild oat | 25 | 85 | 0 | 20 |

| | COMPOUND | | | | | | | |
|---|---|---|---|---|---|---|---|---|
| Rate 62 g/ha | 2 | 3 | 4 | 6 | 8 | 9 | 14 | 17 |
| POSTEMERGENCE | | | | | | | | |
| Barley Igri | 35 | 35 | 30 | 30 | 35 | 30 | 30 | 25 |
| Barnyardgr. (Flood) | 10 | 30 | 25 | 25 | 100 | 10 | 0 | 60 |
| Barnyardgrass | 35 | 25 | 70 | 30 | 100 | 95 | 30 | 60 |
| Bedstraw | 60 | 70 | 100 | 100 | 100 | 95 | 0 | 100 |
| Blackgrass | 10 | 20 | 25 | 45 | 55 | 80 | 30 | 25 |
| Chickweed | 30 | 40 | 75 | 70 | 100 | 50 | 55 | 60 |
| Cocklebur | 90 | 90 | 100 | 100 | 100 | 40 | 70 | 90 |
| Corn | 10 | 40 | 35 | 50 | 90 | 70 | 25 | 30 |
| Cotton | 100 | 100 | 100 | 100 | 100 | 100 | 100 | 100 |
| Crabgrass | 15 | 50 | 40 | 40 | 70 | 50 | 35 | 30 |
| Downy Brome | 0 | 15 | 20 | 30 | 10 | 10 | 20 | 0 |
| Duck salad | 0 | 0 | 0 | 0 | 0 | 0 | 0 | 80 |
| Giant foxtail | 35 | 60 | 50 | 60 | 90 | 70 | 20 | 30 |
| Italn. Rygrass | 0 | 0 | 15 | 20 | 75 | 0 | 10 | 25 |
| Johnsongrass | 30 | 40 | 70 | 70 | 100 | 90 | 30 | 60 |
| Lambsquarter | 85 | 95 | 85 | 100 | 100 | 95 | 65 | 100 |
| Morningglory | 100 | 100 | 100 | 100 | 100 | 60 | 90 | 95 |
| Rape | 60 | 100 | 100 | — | 100 | 100 | 90 | 100 |
| Redroot Pigweed | 95 | 100 | 100 | 100 | 100 | 100 | 75 | 70 |
| Rice Japonica | 20 | 30 | 25 | 25 | 80 | 35 | 0 | 45 |
| Soybean | 70 | 50 | 50 | 50 | — | 40 | — | 80 |
| Speedwell | 100 | 90 | 95 | 100 | 100 | — | 80 | 100 |
| sugar beet | 100 | 100 | 100 | 100 | 100 | 100 | 60 | 100 |
| Umbrella sedge | 10 | 0 | 0 | 0 | 0 | 0 | 80 | 75 |
| Velvetleaf | 100 | 100 | 100 | 100 | 100 | 100 | 100 | 100 |
| Watergrass | 0 | 20 | 15 | 15 | 100 | 35 | 0 | 65 |
| Wheat | 25 | 35 | 10 | 15 | 40 | 40 | 10 | 0 |
| Wild buckwheat | 65 | 100 | 100 | 95 | 100 | 100 | 35 | 100 |
| Wild oat | 35 | 25 | 20 | 25 | 30 | 65 | 20 | 30 |
| Rate 62 g/ha | | | | | | | | |
| PREEMERGENCE | | | | | | | | |
| Barley Igri | 0 | 0 | 0 | 0 | 0 | 10 | 0 | 10 |
| Barnyardgrass | 10 | 20 | 0 | 30 | 100 | 35 | 0 | 20 |
| Bedstraw | 0 | 25 | 10 | 0 | 100 | 85 | 0 | 95 |
| Blackgrass | 0 | 0 | 0 | 10 | 20 | 10 | 20 | 0 |
| Chickweed | 10 | 20 | 10 | 100 | 10 | 0 | 0 | |
| Cocklebur | 0 | 0 | 0 | 55 | 50 | 0 | 20 | 50 |
| Corn | 0 | 0 | 0 | 0 | 40 | 0 | 0 | 0 |
| Cotton | 0 | 0 | 0 | 0 | 100 | 50 | 20 | 100 |
| Crabgrass | 0 | 0 | 0 | 0 | 95 | 35 | 15 | 40 |
| Downy Brome | 0 | 0 | 0 | 0 | 10 | 0 | 0 | 0 |
| Giant foxtail | 20 | 0 | 0 | 0 | 100 | 90 | — | 30 |
| Italn. Rygrass | 0 | 0 | 0 | 0 | 50 | 10 | 0 | 0 |
| Johnsongrass | 10 | 0 | 0 | 20 | 95 | 30 | 0 | 30 |
| Lambsquarter | 40 | 90 | 85 | 95 | 100 | 100 | 0 | 100 |
| Morningglory | 0 | 15 | 10 | 35 | 100 | 50 | 10 | 70 |
| Rape | 0 | 0 | 0 | 0 | 100 | 65 | 0 | 80 |
| Redroot Pigweed | 100 | 0 | 0 | 10 | 100 | 100 | — | 80 |

TABLE B-continued

| | | | | | | | | |
|---|---|---|---|---|---|---|---|---|
| Soybean | 0 | 10 | 10 | 0 | 100 | 20 | 0 | 35 |
| Speedwell | — | 10 | 50 | 25 | 100 | 100 | 0 | 85 |
| Sugar beet | 10 | 0 | 10 | 25 | 100 | 100 | 0 | 100 |
| Velvetleaf | 100 | 60 | 10 | 85 | 100 | 30 | 0 | 100 |
| Wheat | 0 | 0 | 0 | 0 | 10 | 10 | 0 | 0 |
| Wild buckwheat | 0 | 25 | 10 | 0 | 100 | 60 | 0 | 95 |
| Wild oat | 10 | 0 | 0 | 0 | 50 | 20 | 0 | 0 |
| Rate 31 g/ha | | | | | | | | |
| POSTEMERGENCE | | | | | | | | |
| Barley Igri | 30 | 35 | — | 30 | 35 | 20 | 20 | 20 |
| Barnyardgr. (Flood) | — | 30 | 20 | 25 | 75 | 0 | 0 | 20 |
| Barnyardgrass | 30 | 20 | 60 | 25 | 100 | 95 | — | 30 |
| Bedstraw | 50 | 70 | 90 | 100 | 100 | 90 | 0 | 65 |
| Blackgrass | 10 | 20 | 25 | 40 | 40 | 60 | 20 | 20 |
| Chickweed | 30 | 40 | 70 | 65 | 100 | 50 | 50 | 50 |
| Cocklebur | 35 | 90 | 100 | 100 | 100 | 40 | 70 | 70 |
| Corn | 10 | 30 | 30 | 30 | 90 | 55 | — | 20 |
| Cotton | 100 | 100 | 100 | 100 | 100 | 100 | 90 | 100 |
| Crabgrass | 10 | 40 | 30 | 40 | 50 | 35 | 35 | 20 |
| Downy Brome | 0 | 15 | 20 | 30 | 0 | 0 | 0 | 0 |
| Duck salad | — | 0 | 0 | 0 | 0 | 0 | 0 | 45 |
| Giant foxtail | 30 | 35 | 40 | 50 | 85 | 40 | 20 | 30 |
| Italn. Rygrass | 0 | 0 | 15 | 20 | 45 | 0 | 10 | 0 |
| Johnsongrass | 20 | 30 | 40 | — | 90 | 80 | — | 30 |
| Lambsquarter | 80 | 95 | 75 | 100 | 100 | 90 | 65 | 76 |
| Morningglory | 80 | 100 | 100 | 100 | 100 | 60 | 60 | 90 |
| Rape | 60 | 90 | 95 | — | 100 | 95 | 75 | 100 |
| Redroot Pigweed | 95 | 90 | 90 | 90 | 100 | 100 | 70 | 70 |
| Rice Japonica | — | 25 | 25 | 25 | 70 | 15 | 0 | 35 |
| Soybean | 70 | 50 | 40 | 50 | 100 | 40 | 50 | 70 |
| Speedwell | 100 | 70 | — | 95 | 100 | — | 80 | 85 |
| Sugar beet | 80 | 100 | 100 | 100 | 100 | 95 | 40 | 100 |
| Umbrella sedge | — | 0 | 0 | 0 | 0 | 0 | 35 | 45 |
| Velvetleaf | 100 | 100 | 100 | 100 | 100 | 100 | 90 | 100 |
| Watergrass | — | 20 | 15 | 10 | 60 | 20 | 0 | 20 |
| Wheat | 25 | 30 | 10 | 15 | 40 | 35 | 0 | 0 |
| Wild buckwheat | 65 | 95 | 100 | 95 | 100 | 100 | 35 | 95 |
| Wild oat | 35 | 25 | 20 | 25 | 30 | 40 | 20 | 25 |
| Rate 31 g/ha | | | | | | | | |
| PREEMERGENCE | | | | | | | | |
| Barley Igri | 0 | 0 | 0 | 0 | 0 | 0 | 0 | 0 |
| Barnyardgrass | 0 | 20 | 0 | 20 | 95 | 10 | 0 | 10 |
| Bedstraw | 0 | 0 | 10 | 0 | 100 | 40 | 0 | 30 |
| Blackgrass | 0 | 0 | 0 | 0 | 10 | 0 | 0 | 0 |
| Chickweed | — | 0 | 20 | 10 | 85 | 0 | 0 | 0 |
| Cocklebur | 0 | 0 | 0 | 20 | 30 | 0 | 10 | 40 |
| Corn | 0 | 0 | 0 | 0 | 30 | 0 | 0 | 0 |
| Cotton | 0 | 0 | 0 | 0 | 100 | 10 | 0 | 100 |
| Crabgrass | 0 | 0 | 0 | 0 | 75 | 0 | 0 | 10 |
| Downy Brome | 0 | 0 | 0 | 0 | 0 | 0 | 0 | 0 |
| Giant foxtail | 0 | 0 | 0 | 0 | 100 | 15 | 0 | 0 |
| Italn. Rygrass | 0 | 0 | 0 | 6 | 35 | 0 | 0 | 0 |
| Johnsongrass | 0 | 0 | 0 | 10 | 35 | 10 | 0 | 0 |
| Lambsquarter | 20 | 85 | 85 | 95 | 100 | 100 | 0 | 70 |
| Morningglory | 0 | 0 | 10 | 30 | 30 | 10 | 0 | 35 |
| Rape | 0 | 0 | 0 | 0 | 75 | 0 | 0 | 40 |
| Redroot Pigweed | 90 | 0 | 0 | 10 | 100 | 100 | 0 | 70 |
| Soybean | 0 | 10 | 0 | 0 | 50 | 20 | 0 | 20 |
| Speedwell | — | 0 | 50 | 25 | 100 | 10 | 0 | 10 |
| Sugar beet | 0 | 0 | 0 | 0 | 85 | 50 | 0 | 90 |
| Velvetleaf | 0 | 0 | 10 | 30 | 100 | 0 | 0 | 100 |
| Wheat | 0 | 0 | 0 | 0 | 0 | 0 | 0 | 0 |
| Wild buckwheat | 0 | 0 | 0 | 0 | 100 | 0 | 0 | 90 |
| Wild oat | 0 | 0 | 0 | 0 | 30 | 20 | 0 | 0 |

| | COMPOUND | | | | |
|---|---|---|---|---|---|
| Rate 16 g/ha | 3 | 4 | 6 | 8 | 17 |
| POST-EMERGENCE | | | | | |
| Barley Igri | 30 | 30 | 30 | 30 | 10 |
| Barnyardgr. (Flood) | 25 | 20 | 25 | 35 | 20 |
| Barnyardgrass | 20 | 50 | 25 | 95 | 10 |
| Bedstraw | 70 | 85 | — | 100 | 65 |
| Blackgrass | 20 | 25 | 40 | 40 | 0 |
| Chickweed | 40 | 60 | 45 | 95 | 45 |
| Cocklebur | 90 | 100 | 90 | 75 | 50 |

TABLE B-continued

| | | | | | |
|---|---|---|---|---|---|
| Corn | 20 | 20 | 25 | 50 | 10 |
| Cotton | 100 | 100 | 100 | 100 | 100 |
| Crabgrass | 25 | 30 | 20 | 35 | 15 |
| Downy Brome | 15 | 15 | 20 | 0 | 0 |
| Duck salad | 0 | 0 | 0 | 0 | 30 |
| Giant foxtail | 25 | 30 | 50 | 45 | 25 |
| Italn. Rygrass | 0 | 0 | 0 | 35 | 0 |
| Johnsongrass | 20 | 40 | 55 | 85 | 25 |
| Lambsquarter | 40 | 65 | 90 | 100 | 60 |
| Morningglory | 100 | 100 | 100 | 100 | 70 |
| Rape | 80 | 90 | 100 | 100 | 95 |
| Redroot Pigweed | 90 | 90 | — | 95 | 70 |
| Rice Japonica | 20 | 20 | 15 | 45 | 30 |
| Soybean | 40 | 35 | 40 | 100 | 50 |
| Speedwell | 70 | 85 | 95 | 100 | — |
| Sugar beet | 100 | 95 | 100 | 100 | 100 |
| Umbrella sedge | 0 | 0 | 0 | 0 | 20 |
| Velvetleaf | 100 | 100 | 100 | 100 | 100 |
| Watergrass | 20 | 15 | 10 | 40 | 20 |
| Wheat | 20 | 0 | 10 | 35 | 0 |
| Wild buckwheat | 90 | 100 | 95 | 100 | 95 |
| Wild oat | 25 | 20 | 25 | 20 | 10 |
| Rate 16 g/ha | | | | | |
| PREEMERGENCE | | | | | |
| Barley Igri | 0 | 0 | 0 | 0 | 0 |
| Barnyardgrass | 20 | 0 | 10 | 50 | 0 |
| Bedstraw | 0 | 0 | 0 | 20 | 30 |
| Blackgrass | 0 | 0 | 0 | 10 | 0 |
| Chickweed | 0 | 0 | 10 | 50 | 0 |
| Cocklebur | 0 | 0 | 0 | 20 | 20 |
| Corn | 0 | 0 | 0 | 25 | 0 |
| Cotton | 0 | 0 | 0 | 90 | 100 |
| Crabgrass | 0 | 0 | 0 | 60 | 0 |
| Downy Brome | 0 | 0 | 0 | 0 | 0 |
| Giant foxtail | 0 | 0 | 0 | 90 | 0 |
| Italn. Rygrass | 0 | 0 | 0 | 0 | 0 |
| Johnsongrass | 0 | 0 | — | 30 | 0 |
| Lambsquarter | 10 | 0 | 95 | 100 | 15 |
| Morningglory | 0 | 0 | 20 | 30 | 35 |
| Rape | 0 | 0 | 0 | 20 | 0 |
| Redroot pigweed | 0 | 0 | 0 | 100 | 35 |
| Soybean | 0 | 0 | 0 | 30 | 20 |
| Speedwell | 0 | 0 | 25 | 100 | 0 |
| Sugar beet | 0 | 0 | 0 | 35 | 45 |
| Velvetleaf | 0 | 0 | 20 | 100 | 70 |
| Wheat | 0 | 0 | 0 | 0 | 0 |
| Wild buckwheat | 0 | 0 | 0 | 85 | 85 |
| Wild oat | 0 | 0 | 0 | 10 | 0 |

| | COMPOUND | | | | | COMPOUND | | | |
|---|---|---|---|---|---|---|---|---|---|
| Rate 8 g/ha | 3 | 4 | 6 | 8 | Rate 8 g/ha | 3 | 4 | 6 | 8 |
| POST-EMERGENCE | | | | | PREEMERGENCE | | | | |
| Barley Igri | 30 | 20 | 30 | 30 | Barley Igri | 0 | 0 | 0 | 0 |
| Barnyardgr. (Flood) | 15 | 15 | 20 | 0 | Barnyardgrass | 0 | 0 | 10 | 40 |
| Barnyardgrass | 20 | 40 | 20 | 45 | Bedstraw | 0 | 0 | 0 | 15 |
| Bedstraw | 55 | 85 | 100 | 70 | Blackgrass | 0 | 0 | 0 | 0 |
| Blackgrass | 20 | 25 | 35 | 20 | Chickweed | 0 | 0 | 10 | 30 |
| Chickweed | 40 | 60 | 30 | 70 | Cocklebur | 0 | 0 | 0 | 15 |
| Cocklebur | 80 | 90 | 90 | 65 | Corn | 0 | 0 | 0 | 0 |
| Corn | 15 | 15 | 20 | 30 | Cotton | 0 | 0 | 0 | 30 |
| Cotton | 100 | 100 | 100 | 100 | Crabgrass | 0 | 0 | 0 | 35 |
| Crabgrass | 25 | 20 | 20 | 20 | Downy Brome | 0 | 0 | 0 | 0 |
| Downy Brome | 10 | 0 | 10 | 0 | Giant foxtail | 0 | 0 | 0 | 35 |
| Duck salad | 0 | 0 | 0 | 0 | Italn. Rygrass | 0 | 0 | 0 | 0 |
| Giant foxtail | 25 | 25 | 35 | 30 | Johnsongrass | 0 | 0 | 0 | 10 |
| Italn. Rygrass | 0 | 0 | 0 | 10 | Lambsquarter | 0 | 0 | 20 | 100 |
| Johnsongrass | 20 | — | 55 | 35 | Morningglory | 0 | 0 | 10 | 20 |
| Lambsquarter | 40 | 50 | 75 | 95 | Rape | 0 | 0 | 0 | 0 |
| Morningglory | 100 | 100 | 100 | 90 | Redroot Pigweed | 0 | 0 | 0 | 90 |
| Rape | 80 | 30 | 100 | 75 | Soybean | 0 | 0 | 0 | 0 |
| Redroot Pigweed | 90 | 80 | 90 | 95 | Speedwell | 0 | — | 10 | 100 |
| Rice Japonica | 20 | 15 | 0 | 30 | Sugar beet | 0 | 0 | 0 | — |
| Soybean | 40 | 35 | 40 | 85 | Velvetleaf | 0 | 0 | 0 | 100 |
| Speedwell | 70 | 85 | 90 | 100 | Wheat | 0 | 0 | 0 | 0 |
| Sugar beet | 100 | — | 100 | 100 | Wild buckwheat | 0 | 0 | 0 | 30 |
| Umbrella sedge | 0 | 0 | 0 | 0 | Wild oat | 0 | 0 | 0 | 0 |

TABLE B-continued

| | | | | |
|---|---|---|---|---|
| Velvetleaf | 100 | 100 | 100 | 100 |
| Watergrass | 20 | 15 | 10 | 0 |
| Wheat | 10 | 0 | 10 | 30 |
| Wild buckwheat | 85 | 85 | 90 | 100 |
| Wild oat | 20 | 20 | 20 | 20 |

Test C

Seeds of barnyardgrass (*Echinochloa crus-galli*), bindweed (*Convolvulus arvensis*), black nightshade (*Solanum ptycanthum dunal*), cassia (*Cassia obtusifolia*), cocklebur (*Xanthium pensylvanicum*), common ragweed (*Ambrosia artemisiifolia*), corn (*Zea mays*), cotton (*Gossypium hirsutum*), crabgrass (Digitaria spp.), fall panicum (*Panicum dichotomiflorum*), giant foxtail (*Setaria faberii*), green foxtail (*Setaria viridis*), jimsonweed (*Datura stramonium*), johnsongrass (*Sorghum halepense*), lambsquarter (*Chenopodium album*), morningglory (Ipomoea spp.), prickly sida (*Sida spinosa*), shattercane (*Sorghum vulgare*), signalgrass (*Brachiaria platyphylla*), smartweed (*Polygonum pensylvanicum*), soybean (*Glycine max*), sunflower (*Helianthus annuus*), velvetleaf (*Abutilon theophrasti*), wild proso (*Panicum miliaceum*), woolly cupgrass (*Eriochloa villosa*), yellow foxtail (*Setaria lutescens*) and purple nutsedge (*Cyperus rotundus*) tubers were planted into a matapeake sandy loam soil. These crops and weeds were grown in the greenhouse until the plants ranged in height from two to eighteen cm (one to four leaf stage), then treated postemergence with the test chemicals formulated in a non-phytotoxic solvent mixture which includes a surfactant. Pots receiving preemergence treatments were planted immediately prior to test chemical application. Pots treated in this fashion were placed in the greenhouse and maintained according to routine greenhouse procedures.

Treated plants and untreated controls were maintained in the greenhouse approximately 14–21 days after application of the test compound. Visual evaluations of plant injury responses were then recorded. Plant response ratings, summarized in Table C, are reported on a 0 to 100 scale where 0 is no effect and 100 is complete control.

| TABLE C | COMPOUND 4 | TABLE C | COMPOUND 4 |
|---|---|---|---|
| Rate 70 g/ha POSTEMERGENCE | | Rate 35 g/ha POSTEMERGENCE | |
| Barnyardgrass | 95 | Barnyardgrass | 65 |
| Bindweed | 100 | Bindweed | 75 |
| Blk Nightshade | 100 | Blk Nightshade | 85 |
| Cassia | 25 | Cassia | 20 |
| Cocklebur | 70 | Cocklebur | 50 |
| Corn | 35 | Corn | 25 |
| Corn IR | 35 | Corn IR | 30 |
| Corn IT | 35 | Corn IT | 30 |
| Cotton | 100 | Cotton | 100 |
| Crabgrass | 20 | Crabgrass | 0 |
| Fall Panicum | 20 | Fall Panicum | 15 |
| Giant Foxtail | 20 | Giant Foxtail | 15 |
| Green Foxtail | 25 | Green Foxtail | 15 |
| Jimsonweed | 70 | Jimsonweed | 55 |
| Johnson Grass | 25 | Johnson Grass | 15 |
| Lambsquarter | 35 | Lambsquarter | 20 |
| Morningglory | 100 | Morningglory | 100 |
| Nutsedge | 15 | Nutsedge | 0 |
| Prickly Sida | 100 | Prickly Sida | 35 |
| Ragweed | 100 | Ragweed | 85 |
| Shattercane | 45 | Shattercane | 35 |
| Signalgrass | 15 | Signalgrass | 15 |
| Smartweed | 30 | Smartweed | 25 |
| Soybean | 45 | Soybean | 40 |
| Soybean 4—4 | 55 | Soybean 4—4 | 45 |
| Soybean W20 | 45 | Soybean W20 | 35 |
| Sunflower | 90 | Sunflower | 85 |
| Velvetleaf | 100 | Velvetleaf | 100 |
| Wild Proso | 30 | Wild Proso | 20 |
| Woolly cupgrass | 30 | Woolly cupgrass | 25 |
| Yellow Foxtail | 20 | Yellow Foxtail | 15 |
| Rate 17 g/ha POSTEMERGENCE | 4 | Rate 8 g/ha POSTEMERGENCE | 4  14 |
| Barnyardgrass | 25 | Barnyardgrass | 10  15 |
| Bindweed | 45 | Bindweed | 25  — |
| Blk Nightshade | 65 | Blk Nightshade | 25  — |
| Cassia | 15 | Cassia | 15  — |
| Cocklebur | 35 | Cocklebur | 30  — |
| Corn | 20 | Corn | 15  20 |
| Corn IR | 20 | Corn IR | 20  30 |
| Corn IT | 20 | Corn IT | 15  20 |
| Cotton | 75 | Cotton | 70  100 |
| Crabgrass | 0 | Crabgrass | 0  25 |
| Fall Panicum | 10 | Fall Panicum | 0  15 |
| Giant Foxtail | 10 | Giant Foxtail | 10  20 |
| Green Foxtail | 15 | Green Foxtail | 10  25 |
| Jimsonweed | 30 | Jimsonweed | 25  — |
| Johnson Grass | 15 | Johnson Grass | 10  25 |
| Lambsquarter | 15 | Lambsquarter | 10  — |
| Morningglory | 100 | Morningglory | 75  — |
| Nutsedge | 0 | Nutsedge | 0  — |
| Prickly Sida | 30 | Prickly Sida | 25  — |
| Ragweed | 60 | Ragweed | 25  — |
| Shattercane | 30 | Shattercane | 25  25 |
| Signalgrass | 10 | Signalgrass | 0  — |
| Smartweed | 20 | Smartweed | 15  — |
| Soybean | 25 | Soybean | 20  45 |
| Soybean 4—4 | 35 | Soybean 4—4 | 35  50 |
| Soybean W20 | 30 | Soybean W20 | 25  65 |
| Sunflower | 65 | Sunflower | 40  30 |
| Velvetleaf | 90 | Velvetleaf | 20  — |
| Wild Proso | 15 | Wild Proso | 15  35 |
| Woolly cupgrass | 15 | Woolly cupgrass | 15  30 |
| Yellow Foxtail | 15 | Yellow Foxtail | 10  35 |
| Rate 4 g/ha POSTEMERGENCE | 4  14 | Rate 2 g/ha POSTEMERGENCE | 14 |
| Barnyardgrass | 10  10 | Barnyardgrass | 0 |
| Bindweed | 15  — | Bindweed | — |
| Blk Nightshade | 10  — | Blk Nightshade | — |
| Cassia | 10  — | Cassia | — |
| Cocklebur | 25  — | Cocklebur | — |
| Corn | 10  15 | Corn | 10 |
| Corn IR | 10  20 | Corn IR | 10 |
| Corn IT | 15  10 | Corn IT | 0 |
| Cotton | 10  85 | Cotton | 75 |
| Crabgrass | 0  10 | Crabgrass | 10 |
| Fall Panicum | 0  10 | Fall Panicum | 0 |
| Giant Foxtail | 0  15 | Giant Foxtail | 10 |
| Green Foxtail | 10  15 | Green Foxtail | 0 |
| Jimsonweed | 10  — | Jimsonweed | — |
| Johnson Grass | 0  20 | Johnson Grass | 0 |
| Lambsquarter | 0  — | Lambsquarter | — |
| Morningglory | 25  — | Morningglory | — |

-continued

| TABLE C | COMPOUND | TABLE C | COMPOUND |
|---|---|---|---|
| Nutsedge | 0 | — Nutsedge | — |
| Prickly Sida | 20 | — Prickly Sida | — |
| Ragweed | 15 | — Ragweed | — |
| Shattercane | 25 | 10 Shattercane | 0 |
| Signalgrass | 0 | — Signalgrass | — |
| Smartweed | 10 | — Smartweed | — |
| Soybean | 15 | 25 Soybean | 10 |
| Soybean 4–4 | 20 | 10 Soybean 4–4 | 10 |
| Soybean W20 | 15 | 35 Soybean W20 | 10 |
| Sunflower | 10 | 25 Sunflower | 15 |
| Velvetleaf | 10 | — Soybean | 10 |
| Wild Proso | 10 | 25 Soybean 4–4 | 10 |
| Woolly cupgrass | 10 | 15 Soybean W20 | 10 |
| Yellow Foxtail | 10 | 25 Sunflower | 15 |
| | | Velvetleaf | — |
| | | Wild Proso | 10 |
| | | Woolly cupgrass | 10 |
| | | Yellow Foxtail | 10 |

Test D

Compounds evaluated in this test were formulated in a non-phytotoxic solvent mixture which includes a surfactant and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include winter barley (*Hordeum vulgare* cv. 'Igri'), blackgrass (*Alopecurus myosuroides*), chickweed (*Stellaria media*), downy brome (*Bromus tectorum*), galium (*Galium aparine*), green foxtail (*Setaria viridis*), kochia (*Kochia scoparia*), lambsquarters (*Chenopodium album*), speedwell (*Veronica persica*), rape (*Brassica napus*), ryegrass (*Lolium multiflorum*), sugar beet (*Beta vulgaris* cv. 'US1'), spring wheat (*Triticum aestivum* cv. 'ERA'), windgrass (*Apera spica-venti*), winter wheat (*Triticum aestivum* cv. 'Talent'), wild buckwheat (*Polygonum convolvulus*), wild mustard (*Sinapis arvensis*), and wild oat (*Avena fatua*).

Treated plants and untreated controls were maintained in a greenhouse for approximately 21 to 28 days, after which all treated plants were compared to untreated controls and visually evaluated. Plant response ratings, summarized in Table D, are based upon a 0 to 100 scale where 0 is no effect and 100 is complete control. A dash response (-) means no test result.

TABLE D

| | COMPOUND | | COMPOUND |
|---|---|---|---|
| Rate 12 g/ha | 8 | Rate 8 g/ha | 8 |
| POSTEMERGENCE | | POSTEMERGENCE | |
| Blackgrass | 10 | Blackgrass | 10 |
| Chickweed | 75 | Chickweed | 55 |
| Downy brome | 10 | Downy brome | 10 |
| Galium | 100 | Galium | 100 |
| Green foxtail | 15 | Green foxtail | 40 |
| Kochia | 100 | Kochia | 100 |
| Lambsquarters | 95 | Lambsquarters | 80 |
| Rape | 100 | Rape | 100 |
| Ryegrass | 10 | Ryegrass | 10 |
| Speedwell | 100 | speedwell | 90 |
| Sugar beet | 100 | Sugar beet | 100 |
| Wheat (Spring) | 30 | Wheat (Spring) | 25 |
| Wheat (Winter) | 25 | Wheat (Winter) | 20 |
| Wild buckwheat | 100 | Wild buckwheat | 100 |
| Wild mustard | 100 | Wild mustard | 100 |
| Wild oat | 20 | Wild oat | 15 |
| Windgrass | 10 | Windgrass | 15 |
| Winter Barley | 20 | Winter Barley | 20 |
| Rate 4 g/ha | 8 | Rate 2 g/ha | 8 |
| POSTEMERGENCE | | POSTEMERGENCE | |
| Blackgrass | 10 | Blackgrass | 5 |
| Chickweed | 50 | Chickweed | 15 |
| Downy brome | 5 | Downy brome | o |
| Galium | 70 | Galium | 50 |
| Green foxtail | 50 | Green foxtail | 30 |
| Kochia | 95 | Kochia | 40 |
| Lambsquarters | 70 | Lambsquarters | 50 |
| Rape | 85 | Rape | — |
| Ryegrass | 5 | Ryegrass | 5 |
| Speedwell | 65 | Speedwell | 55 |
| Sugar beet | 90 | Sugar beet | — |
| Wheat (Spring) | 10 | Wheat (Spring) | 10 |
| Wheat (Winter) | 15 | Wheat (Winter) | 10 |
| Wild buckwheat | 85 | Wild buckwheat | 100 |
| Wild mustard | 100 | Wild mustard | 25 |
| Wild oat | 10 | Wild oat | 15 |
| Windgrass | 10 | Windgrass | 0 |
| Winter Barley | 15 | Winter Barley | 10 |

We claim:

1. A compound of Formula I, or an agriculturally-suitable salt thereof,

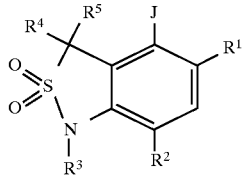

wherein $R^1$ is H; F; Cl; or Br;

$R^2$ is H; F; Cl; Br; $CF_3$; nitro; or cyano;

$R^3$ is H; $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_3$–$C_8$ alkoxyalkoxyalkyl; $C_3$–$C_8$ haloalkynyl; $C_3$–$C_8$ haloalkenyl; $C_1$–$C_8$ alkylsulfonyl; $C_1$–$C_8$ haloalkylsulfonyl; $C_3$–$C_8$ alkoxycarbonylalkyl; $S(O)_2NH(C_1$–$C_8$ alkyl); $C(O)R^6$; or benzyl optionally substituted on the phenyl ring with $R^7$;

$R^4$ is H; $C_1$–$C_3$ alkyl; or halogen;

$R^5$ is H; $C_1$–$C_6$ alkyl; $C_1$–$C_6$ haloalkyl; halogen; $S(O)_2(C_1$–$C_6$ alkyl); or $C(=O)R^8$; or $R^4$ and $R^5$ are taken together along with the carbon to which they are attached to form a spiro-cyclopropane ring;

$R^6$ is $C_1$–$C_6$ alkyl; $C_1$–$C_6$ haloalkyl; $C_1$–$C_6$ alkoxy; $NH(C_1C_6$ alkyl); phenyl optionally substituted with $R^7$; benzyl; or $C_2$–$C_8$ dialkylamino;

$R^7$ is $C_1$–$C_6$ alkyl; 1–2 halogen; $C_1$–$C_6$ alkoxy; or $CF_3$;

$R^8$ is H; $C_1$–$C_6$ alkyl; $C_1$–$C_6$ alkoxy; or $NH(C_1$–$C_6$ alkyl);

J is

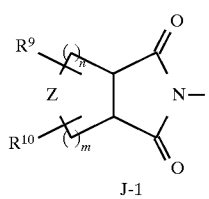 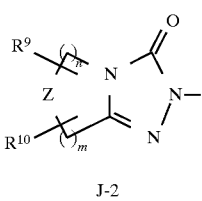

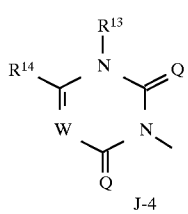

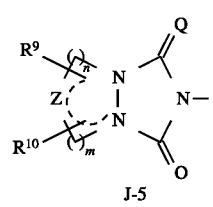 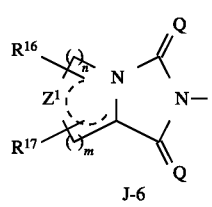

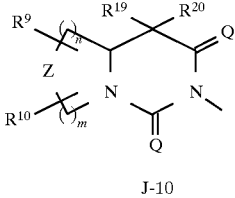 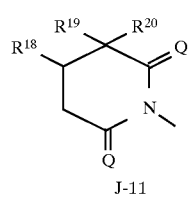

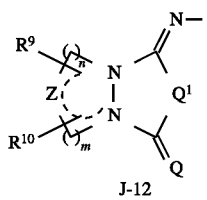

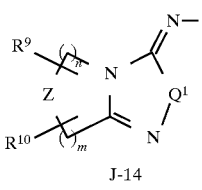 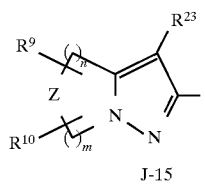

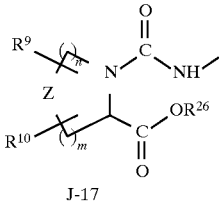

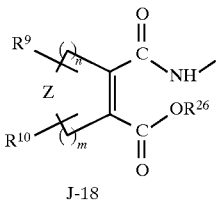

wherein the dashed line in J-5, J-6 and J-12 indicates that the left-handed ring contains only single bonds or one bond in the ring is a carbon—carbon double bond;

n and m are each independently 0; 1; 2; or 3; provided that m+n is 3;

Z is $CR^9R^{10}$ or $N(C_1$–$C_4$ alkyl);

each $R^9$ is independently H; $C_1$–$C_3$ alkyl; halogen; hydroxy; $C_1$–$C_6$ alkoxy; $C_1$–$C_6$ haloalkyl; $C_1$–$C_6$ haloalkoxy; $C_2$–$C_6$ alkylcarbonyloxy; or $C_2$–$C_6$ haloalkylcarbonyloxy;

each $R^{10}$ is independently H; $C_1$–$C_3$ alkyl; hydroxy; or halogen;

$R^{13}$ is H; $C_1$–$C_6$ alkyl; $C_1$–$C_6$ haloalkyl; $C_3$–$C_6$ alkenyl; $C_3$–$C_6$ haloalkenyl; $C_3$–$C_6$ alkynyl; $C_3$–$C_6$ haloalkynyl; HC(=O); $(C_1$–$C_4$ alkyl) C(=O); or $NH_2$;

$R^{14}$ is $C_1$–$C_6$ alkyl; $C_1$–$C_6$ alkylthio; $C_1$–$C_6$ haloalkyl; $CF_3$; or $N(CH_3)_2$;

W is N or $CR^{15}$;

$R^{15}$ is H; $C_1$–$C_6$ alkyl; halogen; or phenyl optionally substituted with $C_1$–$C_6$ alkyl, 1–2 halogen, $C_1$–$C_6$ alkoxy, or $CF_3$;

each Q is independently O or S;

$Q^1$ is O or S;

$Z^1$ is $CR^{16}R^{17}$ or $N(C_1$–$C_4$ alkyl);

each $R^{16}$ is independently H; halogen; hydroxy; $C_1$–$C_6$ alkoxy; $C_1$–$C_6$ haloalkyl; $C_1$–$C_6$ haloalkoxy; $C_2$–$C_6$ alkylcarbonyloxy; or $C_2$–$C_6$ haloalkylcarbonyloxy;

each $R^{17}$ is independently H; hydroxy; or halogen; or when $R^{16}$ and $R^{17}$ are bonded to adjacent atoms they can be taken together with the carbons to which they are attached to form

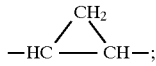

$R^{18}$ is $C_1$–$C_6$ alkyl; halogen; or $C_1$–$C_6$ haloalkyl;

$R^{19}$ and $R^{20}$ are each independently H; $C_1$–$C_6$ alkyl; or $C_1$–$C_6$ haloalkyl;

$R^{23}$ is halogen or cyano; and $R^{26}$ is $C_1$–$C_6$ alkyl; $C_1$–$C_6$ haloalkyl; or phenyl optionally substituted with $C_1$–$C_6$ alkyl, 1–2 halogen, 1–2 nitro, $C_1$–$C_6$ alkoxy, or $CF_3$.

2. A compound of claim 1 wherein:

$R^1$ is F or Cl;

$R^2$ is F; Cl; or Br;

$R^3$ is H; $C_1$–$C_6$ alkyl; $C_3$–$C_6$ cycloalkyl; $C_3$–$C_6$ alkynyl; $C_1$–$C_6$ haloalkyl; $C_2$–$C_6$ alkoxyalkyl; $C_3$–$C_6$ alkenyl; $C_3$–$C_6$ haloalkenyl; $C_1$–$C_6$ alkylsufonyl; $C_3$–$C_6$ alkoxycarbonylalkyl; $C(O)R^6$; or benzyl optionally substituted on the phenyl ring with $R^7$;

$R^4$ is H or halogen;

$R^5$ is H;

J is J-1; J-2; J-4; J-5; J-6; J-12; or J-15;

Z is $CR^9R^{10}$ or $N(C_1$–$C_4$ alkyl);

each $R^9$ is independently H; halogen; or $C_1$–$C_6$ haloalkoxy;

each $R^{10}$ is independently H or halogen;

each Q is O;

$Q^1$ is S;

$Z^1$ is $CR_{16}R^{17}$ or $N(C_1$–$C_4$ alkyl);

each $R^{16}$ is independently H; halogen; or haloalkoxy;

each $R^{17}$ is independently H or halogen; or when $R^{16}$ and $R^{17}$ are bonded to adjacent atoms they can be taken together with the carbons to which they are attached to form

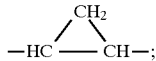

$R^{18}$ is t-butyl or $CH_2CH_2CH_2F$; and $R^{23}$ is Cl or cyano.

3. A compound of claim 2 wherein:

$R^2$ is F or Cl;

$R^3$ is $C_1$–$C_6$ alkyl; $C_3$–$C_6$ cycloalkyl; $C_3$–$C_6$ alkenyl; $C_3$–$C_6$ alkynyl; $C_3$–$C_6$ alkoxycarbonylalkyl; or benzyl optionally substituted on the phenyl ring with $R^7$;

J is J-1; J-2; J-4; J-5; J-6; or J-12;

Z is $CR^9R^{10}$;

each $R^9$ is independently H or halogen;

$R^{13}$ is $CH_3$;

$R^{14}$ is $CF_3$;

W is CH;

$Z^1$ is $CR^{16}R^{17}$;

each $R^{16}$ is independently H or halogen;

each $R^{17}$ is independently H or halogen; or when $R^{16}$ and $R^{17}$ are bonded to adjacent atoms they can be taken together with the carbons to which they are attached to from

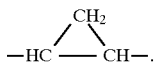

4. A compound of claim 3 wherein:

$R^2$ is Cl;

$R^3$ is $C_1$–$C_6$ alkyl; $C_3$–$C_6$ alkenyl; or $C_3$–$C_6$ alkynyl;

J is J-1; J-2; J-4; J-6; J-12;

Z is $CR^9R^{10}$;

$R^9$ is independently H or F;

$R^{10}$ is independently H or F;

$Z^1$ is $CR^{16}R^{17}$;

$R^{16}$ is independently H or F; and $R^{17}$ is independently H or F.

5. A compound of claim 1 of Formula I.

6. A compound of claim 2 which is selected from the group:

3-[7-chloro-5-fluoro-1,3-dihydro-1-[(4-methoxyphenyl) methyl]-2,1-benzisothiazol-4-yl]-1-methyl-6-tritluoromethyl)-2,4 (1H, 3H)-pyrimidinedione S,S-dioxide;

3-(7-chloro-5-fluoro-1,3-dihydro-2,1-benzisothiazol-4-yl)-1-methyl-6-(trifluoromethyl)-2,4(1H, 3H)-pyrimidinedione S,S-dioxide;

3-(7-chloro-1-ethyl-5-fluoro-1,3-dihydro-2,1 benzisothiazol-4-yl)-1-methyl-6-(trifluoromethyl)-2, 4(1H, 3H)-pyrimidinedione S,S-dioxide; and 3-[(7-chloro-1-ethyl-5-fluoro-1,3-dihydro-2,1-benzisothiazol-4-yl) imino]tetrahydro-1H, 3H [1,3,4] thiodiazol[3,4-a]pyridazin-1-one S,S-dioxide.

7. A herbicidal composition comprising an effective amount of a compound according to claim 1 and at least one of a surfactant, a solid diluent or a liquid diluent.

8. A herbicidal composition comprising an effective amount of a compound according to claim 2 and at least one of a surfactant, a solid diluent or a liquid diluent.

9. A method for controlling the growth of undesired vegetation comprising contacting the vegetation or its enviroment with a herbicidally effective amount of a composition of claim 7.

* * * * *